United States Patent
Ferrara

(10) Patent No.: US 11,524,053 B2
(45) Date of Patent: Dec. 13, 2022

(54) METHODS AND COMPOSITIONS FOR TREATMENT OF ANGIOGENIC DISORDERS USING ANTI-VEGF AGENTS

(71) Applicant: The Regents of the University of California, Oakland, CA (US)

(72) Inventor: Napoleone Ferrara, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/962,529

(22) PCT Filed: Jan. 25, 2019

(86) PCT No.: PCT/US2019/015160
§ 371 (c)(1),
(2) Date: Jul. 16, 2020

(87) PCT Pub. No.: WO2019/147944
PCT Pub. Date: Aug. 1, 2019

(65) Prior Publication Data
US 2020/0353041 A1    Nov. 12, 2020

Related U.S. Application Data

(60) Provisional application No. 62/622,382, filed on Jan. 26, 2018.

(51) Int. Cl.
*A61K 38/00* (2006.01)
*C07K 14/71* (2006.01)
*A61K 38/17* (2006.01)
*A61K 9/00* (2006.01)

(52) U.S. Cl.
CPC .......... *A61K 38/179* (2013.01); *A61K 9/0019* (2013.01); *A61K 9/0048* (2013.01)

(58) Field of Classification Search
CPC combination set(s) only.
See application file for complete search history.

(56) References Cited

U.S. PATENT DOCUMENTS

| | | |
|---|---|---|
| 5,595,760 A | 1/1997 | Cherif-Cheikh |
| 5,672,659 A | 9/1997 | Shalaby et al. |
| 5,712,380 A | 1/1998 | Kendall et al. |
| 5,861,484 A | 1/1999 | Kendall et al. |
| 5,952,199 A | 9/1999 | Davis-Smyth et al. |
| 5,959,760 A | 9/1999 | Yamada et al. |
| 6,270,993 B1 | 8/2001 | Shibuya et al. |
| 6,383,486 B1 * | 5/2002 | Davis-Smyth ............ A61P 9/00 424/158.1 |
| 6,833,349 B2 | 12/2004 | Xia et al. |
| 7,070,959 B1 | 7/2006 | Papadopoulos et al. |
| 7,071,159 B2 | 7/2006 | Kendall et al. |
| 7,087,411 B2 | 8/2006 | Daly et al. |
| 7,141,607 B1 | 11/2006 | Si et al. |
| 7,279,159 B2 | 10/2007 | Daly et al. |
| 7,303,746 B2 | 12/2007 | Wiegand et al. |
| 7,303,747 B2 | 12/2007 | Wiegand et al. |
| 7,303,748 B2 | 12/2007 | Wiegand et al. |
| 7,306,799 B2 | 12/2007 | Wiegand et al. |
| 7,354,578 B2 | 4/2008 | Kandel et al. |
| 7,354,579 B2 | 4/2008 | Holash et al. |
| 7,354,580 B2 | 4/2008 | Cedarbaum |
| 7,354,581 B2 | 4/2008 | Cedarbaum et al. |
| 7,354,582 B2 | 4/2008 | Yung et al. |
| 7,374,757 B2 | 5/2008 | Papadopoulos et al. |
| 7,374,758 B2 | 5/2008 | Papadopoulos et al. |
| 7,396,664 B2 | 7/2008 | Daly et al. |
| 7,399,612 B2 | 7/2008 | Daly et al. |
| 7,449,182 B2 | 11/2008 | Cedarbaum et al. |
| 7,479,272 B2 | 1/2009 | Cedarbaum |
| 7,479,273 B2 | 1/2009 | Cedarbaum |
| 7,479,274 B2 | 1/2009 | Cedarbaum |
| 7,479,275 B2 | 1/2009 | Cedarbaum |
| 7,482,001 B2 | 1/2009 | Cedarbaum |
| 7,482,002 B2 | 1/2009 | Cedarbaum |

(Continued)

FOREIGN PATENT DOCUMENTS

| | | |
|---|---|---|
| CN | 1793179 A | 6/2006 |
| EP | 1183353 B1 | 4/2005 |

(Continued)

OTHER PUBLICATIONS

Aiello, et al., Suppression of retinal neovascularization in vivo by inhibition of vascular endothelial growth factor (VEGF) using soluble VEGF-receptor chimeric proteins, Proc. Natl. Acad. Sci., USA, vol. 92, pp. 10457-10461, Nov. 1995, Medical Sciences.

(Continued)

*Primary Examiner* — Julie Ha
*Assistant Examiner* — Kristina M Hellman
(74) *Attorney, Agent, or Firm* — Eversheds Sutherland (US) LLP

(57) ABSTRACT

Provided are methods and compositions for treatment of angiogenic disorders using anti-VEGF agents. The anti-VEGF agents comprise VEGF binding domains and have the ability to bind vitreous. Provided are exemplary embodiments of Fc-IgG fusion proteins with VEGF binding domains with strong heparin-binding characteristics, strong inhibition of VEGF mitogenic activity, and improved pharmacokinetics, namely longer half-lives of the anti-VEGF agents and consequently less frequent dosing.

3 Claims, 33 Drawing Sheets
Specification includes a Sequence Listing.

(56) References Cited

U.S. PATENT DOCUMENTS

| | | | |
|---|---|---|---|
| 7,521,049 B2 | 4/2009 | Wiegand et al. |
| 7,531,172 B2 | 5/2009 | Stahl et al. |
| 7,531,173 B2 | 5/2009 | Wiegand et al. |
| 7,582,726 B2 | 9/2009 | Chen et al. |
| 7,608,261 B2 | 10/2009 | Furfine et al. |
| 7,635,474 B2 | 12/2009 | Daly et al. |
| 7,704,500 B2 | 4/2010 | Papadopoulos et al. |
| 7,807,164 B2 | 10/2010 | Furfine et al. |
| 7,972,598 B2 | 7/2011 | Daly et al. |
| 8,034,375 B2 | 10/2011 | Desai et al. |
| 8,034,772 B2 | 10/2011 | Kendall et al. |
| 8,048,418 B2 | 11/2011 | Noguera-Troise et al. |
| 8,084,234 B2 | 12/2011 | Papadopoulos et al. |
| 8,092,803 B2 | 1/2012 | Furfine et al. |
| 8,110,546 B2 | 2/2012 | Dix et al. |
| 8,324,169 B2 | 12/2012 | Quinn |
| 8,350,010 B2 | 1/2013 | Chuntharapai et al. |
| 8,404,638 B2 | 3/2013 | Dix et al. |
| 8,481,046 B2 | 7/2013 | Furfine et al. |
| 8,647,842 B2 | 2/2014 | Papadopoulos et al. |
| 8,710,004 B2 | 4/2014 | Dix et al. |
| 8,735,394 B2 | 5/2014 | Desai et al. |
| 8,802,107 B2 | 8/2014 | Furfine et al. |
| 8,921,316 B2 | 12/2014 | Dix et al. |
| 9,056,102 B2 | 6/2015 | Quinn |
| 9,139,644 B2 | 9/2015 | Papadopoulos et al. |
| 9,254,338 B2 | 2/2016 | Yancopoulos |
| 9,273,113 B2 | 3/2016 | Davis-Smyth et al. |
| 9,284,369 B2 | 3/2016 | Ferrara et al. |
| 9,340,594 B2 | 5/2016 | Furfine et al. |
| 9,416,167 B2 | 8/2016 | Dix et al. |
| 9,441,029 B2 | 9/2016 | Stefano et al. |
| 9,511,140 B2 | 12/2016 | Dix et al. |
| 9,561,288 B2 | 2/2017 | Desai et al. |
| 9,580,489 B2 | 2/2017 | Furfine et al. |
| 9,636,400 B2 | 5/2017 | Dix et al. |
| 9,637,534 B2 | 5/2017 | Pechan et al. |
| 9,657,084 B2 | 5/2017 | Ke et al. |
| 9,669,069 B2 | 6/2017 | Yancopoulos |
| 9,708,386 B2 | 7/2017 | Papadopoulos et al. |
| 9,777,261 B2 | 10/2017 | Kim et al. |
| 9,856,462 B2 | 1/2018 | Kim et al. |
| 9,914,763 B2 | 3/2018 | Furfine et al. |
| 9,931,330 B2 | 4/2018 | Zarnitsyn et al. |
| 10,023,627 B2 | 7/2018 | Kim et al. |
| 10,130,681 B2 | 11/2018 | Yancopoulos |
| 10,183,983 B2 | 1/2019 | Pechan et al. |
| 10,206,910 B2 | 2/2019 | Beeharry et al. |
| 10,308,917 B2 | 6/2019 | Stefano et al. |
| 10,342,669 B2 | 7/2019 | Hopkins |
| 10,364,466 B2 | 7/2019 | Bais et al. |
| 10,392,430 B2 | 8/2019 | Papadopoulos et al. |
| 10,400,025 B2 | 9/2019 | Furfine et al. |
| 10,406,226 B2 | 9/2019 | Dix et al. |
| 2003/0017977 A1 | 1/2003 | Xia et al. |
| 2007/0010442 A1 | 1/2007 | Kendall et al. |
| 2008/0292628 A1 | 11/2008 | Hui |
| 2010/0331250 A1* | 12/2010 | Zhou ............... C07K 14/71 |
| | | 514/8.1 |
| 2013/0101557 A1* | 4/2013 | Yun ............... A61P 9/08 |
| | | 424/93.2 |
| 2013/0195984 A1 | 8/2013 | Desai et al. |
| 2015/0175675 A1 | 6/2015 | Kitajewski et al. |
| 2016/0024483 A1 | 1/2016 | Kim et al. |
| 2016/0032259 A1 | 2/2016 | Kim et al. |
| 2017/0232199 A1 | 8/2017 | Fiedler |
| 2017/0281725 A1 | 10/2017 | Sims et al. |
| 2017/0305996 A1 | 10/2017 | Kim et al. |
| 2017/0342127 A1 | 11/2017 | Pechan et al. |
| 2018/0015181 A1 | 1/2018 | Desai et al. |
| 2018/0092747 A1 | 4/2018 | Hopkins |
| 2018/0326126 A1 | 11/2018 | Fiedler |
| 2018/0339018 A1 | 11/2018 | Yancopoulos |
| 2019/0046609 A1 | 2/2019 | Yancopoulos |
| 2019/0117767 A1 | 4/2019 | Vitti et al. |
| 2019/0194271 A1 | 6/2019 | Wu et al. |
| 2019/0201385 A1 | 7/2019 | Beeharry et al. |
| 2019/0240208 A1 | 8/2019 | Zarnitsyn et al. |
| 2019/0247463 A1 | 8/2019 | Yancopoulos |
| 2019/0345223 A1 | 11/2019 | Pechan et al. |
| 2022/0088128 A1 | 3/2022 | Ferrara |
| 2022/0088129 A1 | 3/2022 | Ferrara |
| 2022/0144918 A1 | 5/2022 | Ferrara |

FOREIGN PATENT DOCUMENTS

| | | |
|---|---|---|
| EP | 1962895 A2 | 6/2007 |
| EP | 1261317 B1 | 10/2007 |
| EP | 2029103 A2 | 12/2007 |
| EP | 1544299 B1 | 12/2008 |
| EP | 2663325 A1 | 7/2012 |
| EP | 2364691 B1 | 4/2013 |
| EP | 2802346 A1 | 7/2013 |
| EP | 1938799 B1 | 8/2013 |
| EP | 2097078 B1 | 4/2014 |
| EP | 2099489 B1 | 5/2014 |
| EP | 2916827 A4 | 5/2014 |
| EP | 1989231 B1 | 5/2015 |
| EP | 1861116 B1 | 9/2015 |
| EP | 2944306 A1 | 11/2015 |
| EP | 3143044 A1 | 11/2015 |
| EP | 2203479 B1 | 1/2016 |
| EP | 2481405 B1 | 3/2016 |
| EP | 3224278 A4 | 6/2016 |
| EP | 3108885 A1 | 12/2016 |
| EP | 2601214 B1 | 1/2017 |
| EP | 2586459 B1 | 5/2017 |
| EP | 3377151 A1 | 5/2017 |
| EP | 3195874 A1 | 7/2017 |
| EP | 3222285 A1 | 9/2017 |
| EP | 3327032 A1 | 5/2018 |
| EP | 3412288 A1 | 12/2018 |
| EP | 3215158 B1 | 5/2019 |
| EP | 3492495 A1 | 5/2019 |
| EP | 3194974 B1 | 10/2019 |
| WO | WO-0075319 A1 | 12/2000 |
| WO | WO-2007149334 A2 | 12/2007 |
| WO | WO-2012097019 A1 | 7/2012 |
| WO | 2013082511 A1 | 6/2013 |
| WO | WO-2013106765 A1 | 7/2013 |
| WO | WO-2015000181 A1 | 1/2015 |
| WO | 2017/001990 A1 | 1/2017 |
| WO | 2018224614 A1 | 12/2018 |
| WO | 2019004799 A1 | 1/2019 |
| WO | 2019055902 A1 | 3/2019 |
| WO | 2019062642 A1 | 4/2019 |
| WO | 2019099921 A2 | 5/2019 |
| WO | 2019147944 A1 | 8/2019 |
| WO | 2019154776 A1 | 8/2019 |
| WO | WO-2021108255 A1 | 6/2021 |

OTHER PUBLICATIONS

Davis-Smyth, et al., The second immunoglobulin-like domain of the VEGF tyrosine kinase receptor Flt-1 determines ligand binding and may initiate a signal transduction cascade, The EMBO Journal, vol. 15, No. 18, pp. 4919-4927, 1996.

Ferrara, et al., Vascular endothelial growth factor is essential for corpus luteum angiogenesis, Nature Medicine, vol. 4, No. 3, pp. 336-340, Mar. 1998.

Herley, et al., Characterization of the VEGF Binding Site on the Flt-1 Receptor, Biochemical and Biophysical Research Communications, 262, pp. 731-738, 1999.

Holash, et al., VEGF-Trap: A VEGF blocker with potent antitumor effects, PNAS, vol. 99, No. 17, pp. 11393-11398, Aug. 20, 2002.

Lee, et al., Novel Glycosylated VEGF Decoy Receptor Fusion Protein, VEGF-Grab, Efficiently Suppresses Tumor Angiogenesis and Progression, Mol. Cancer Ther., 14(2), pp. 470-479, 2015, Published OnlineFirst Dec. 22, 2014.

Li, et al., A fusion Fragment from Flt-1 and KDR, acted as VEGF decoy receptor and exhibited anti-tumor function, Biotechnol Lett, 32:1609-1613, 2010.

(56) References Cited

OTHER PUBLICATIONS

Ma, et al., Identification of the ligand-binding domain of human vascular-endothelial-growth-factor receptor Flt-I, Biotechnol. Appl. Biochem. 34, 199-204, 2001.
Park, et al., The Fourth Immunoglobulin-like Loop in the Extracellular Domain of FLT-1, a VEGF Receptor, Includes a Major Heparin-Binding Site, Biochemical and Biophysical Research Communications, 264, 730-734, 1999.
Pechan, et al., Novel anti-VEGF chimeric molecules delivered by AAV vectors in inhibition of retinal neovascularization, Gene Therapy, 16, 10-16, 2009.
Tan, et al., A small peptide derived from Flt-1 (VEGFR-1) functions as an angiogenic inhibitor, FEBS Letters, 494, 150-156, 2001.
Yu, et al., Soluble Vascular Endothelial Growth Factor Decoy Receptor FP3 Exerts Potent Antiangiogenic Effects, www.moleculartherapy.org, vol. 20, No. 5, 938-947, May 2012.
International Application PCT/US2020/061519 Search Report and Written Opinion, dated Feb. 12, 2021, 9 pages.
PCT International Search Report and Written Opinion for PCT Application No. PCT/US2019/015160 dated Apr. 10, 2019 (11 pages).
Alitalo et al.: Lymphangiogenesis in development and human disease. Nature. 438:946-953 (2005).
Apte et al.: VEGF in Signaling and Disease: Beyond Discovery and Development. Cell. 176:1248-1264 (2019).
Bachmann et al.: The role of antibody concentration and avidity in antiviral protection. Science. 276:2024-2027 (1997).
Barleon et al.: Mapping of the sites for ligand binding and receptor dimerization at the extracellular domain of the vascular endothelial growth factor receptor FLT-1. Journal of Biological Chemistry. 272:10382-10388 (1997).
Bhattacharya et al.: PLoS ONE 12(3):e0171355. https://doi.org/10/1371/journal.pone.0171355 22 pages (2017).
Bogdanovich et al.: Human IgG1 antibodies suppress angiogenesis in a target-independent manner. Signal Transduct Target Ther. 1 (2016).
Brozzo et al.: Thermodynamic and structural description of allosterically regulated VEGFR-2 dimerization. Blood. 119:1781-1788 (2012).
Campa et al.: Effects of an anti-VEGF-A Monoclonal antibody on laser-induced choroidal neovascularization in mice: optimizing methods to quantify vascular changes. Invest Ophthalmol Vis Sci. 49:1178-1183 (2008).
Capon et al.: Designing CD4 immunoadhesins for AIDS therapy. Nature. 337:525-531 (1989).
Chakrabarti et al.: Studies to Prevent Degradation of Recombinant Fc-Fusion Protein Expressed in Mammalian Cell Line and Protein Characterization. International Journal of Molecular Sciences. 17(6):1-22 (2016).
Chamow et al.: Immunoadhesins: principles and applications. Trends in Biotechnology. 14:52-60 (1996).
Chamow et al.: Therapeutic Fc-Fusion Proteins. Willey Blackwell (2014).
Chen et al.: Erythropoietin deficiency decreases vascular stability in mice. J Clin Invest. 118:526-533 (2008).
Chen et al.: Selection and analysis of an optimized anti-VEGF antibody: crystal structure of an affinity-matured Fab in complex with antigen. Journal of Molecular Biology. 293:865-881 (1999).
Chen et al.: Suppression of retinal neovascularization by erythropoietin siRNA in a mouse model of proliferative retinopathy. Invest Ophtalmol Vis Sci. 50:1329-1335 (2009).
Christinger et al.: The Crystal Structure of Placental Growth Factor in Complex with Domain 2 of Vascular Endothelial Growth Factor Receptor-1. J Biol Chem. 279:10382-10388 (2004).
De Vries et al.: The fms-like tyrosine kinase, a receptor for vascular endothelial growth factor. Science. 255:989-991 (1992).
Dvorak et al.: Distribution of vascular permeability factor (vascular endothelial growth factor) in tumors: concentration in tumor blood vessels. Journal of Experimental Medicine. 174:1275-1278 (1991).
Ellison et al.: The nucleotide sequence of a human immunoglobulin Cγ1 gene. Nucleic Acids Research. 10(13): 4071-4079 (1982).

European Patent Application No. 19744016.7 Extended European Search Report dated Oct. 21, 2021.
Fenton et al.: Rheostat positions: A new classification of protein positions relevant to pharmacogenomics. Medicinal Chemistry Research. 29:1133-1146 (2020).
Ferrara et al.: Ten years of anti-vascular endothelial growth factor therapy. Nat Rev Drug Discov. 15:385-403 (2016).
Ferrara et al.: The biology of VEGF and its receptors. Nature Med. 9:669-676 (2003).
Ferrara N.: Binding to the extracellular matrix and proteolytic processing: two key mechanisms regulating vascular endothelial growth factor action. Mol Biol Cell. 21:687-690 (2010).
Ferrara N.: VEGF and the quest for tumour angiogenesis factors. Nat Rev Cancer. 2:759-803 (2002).
Folkman et al.: Angiogenic factors. Science. 235:442-447 (1987).
Freund et al.: Aflibercept: a review of its use in the treatment of choroidal neovascularization due to age-related macular degeneration. Clinical Ophthalmology. 9:2355-2371 (2015).
Gait et al.: Oligonucleotide Synthesis, a Practical Approach: Oxford Press. pp. 217 Abstract (1984).
Gardiner et al.: Inhibition of tumor necrosis factor-alpha improves physiological angiogenesis and reduces pathological neovascularization in ischemic retinopathy. Am J Pathol. 166:637-644 (2005).
Gerber et al.: Complete inhibition of rhabdomyosocarcoma xenograft growth and neovascularization requires blockade of both tumor and host vascular endothelial growth factor. Cancer Res. 60:6253-6258 (2000).
Gerber et al.: Mice expressing a humanized form of VEGF-A may provide insights into safety and efficacy of anti-VEGF antibodies. Proc Natl Acad Sci U.S.A. 104:3478-3483 (2007).
Gerber et al.: VEGF couples hypertrophic cartilage remodeling, ossification and angiogenesis during endochrondral bone formation. Nature Med. 5:623-628 (1999).
Gerber et al.: VEGF is required for growth and survival in neonatal mice. Development. 126:1149-1159 (1999).
Gerhardt et al.: VEGF guides angiogenic sprouting utilizing endothelial tip cell filopodia. J Cell Biol. 161:1163j-1177 (2003).
Harding et al.: Adeno-Associated Virus Serotype 6 (AAV-6) Vector Mediated Gene Transfer of Soluble VEGF Receptors for the Treatment of Glioblastoma Multiforme. Molecular Therapy. Elsevier Inc. 9:405-406 (2004) Abstract.
Holz et al.: Multi-country real-life experience of anti-vascular endothelial growth factor therapy for wet age-related macular degeneration. Br J Ophthalmol. 99:220-226 (2015).
Houck et al.: Dual regulation of vascular endothelial growth factor bioavailability by genetic and proteolytic mechanisms. J-Biol-Chem 267:26037-26037 (1992).
Houck et al.: The vascular endothelial growth factor family: identification of a fourth molecular species and characterization of alternative splicing of RNA. Molecular Endocrinology. 5:1806-1814(1991).
Joukov et al.: A novel vascular endothelial growth factor, VEGF-C, is a ligand for the Flt4 (VEGFR-3) and KDR (VEGRF-2) receptor tyrosine kinases. EMBO-J. 15:1751 issn: 0261-4189 (1996).
Kim et al.: Potent VEGF blockade causes regression of coopted vessels in a model of neuroblastoma. Proc Natl Acad Sci U.S.A. 99:11399-11404 (2002).
Klagsbrun et al.: Regulators of angiogenesis. Annu Rev Physiol. 53:217-239 (1991).
Kwak et al.: VEGF is major stimulator in model of choroidal neovascularization. Invest Ophthalmol Vis Sci. 41:3158-3164 (2000).
Lambert et al.: Laser-induced choroidal neovascularization model to study age-related macular degeneration in imce. Nat Protoc. 8:2197-2211 (2013).
Lange et al. Intravitreal injection of the heparin analog 5-amino-2-naphthalenesulfonate reduces retinal neovascularization in mice. Exp Eye Res. 85:323-327 (2007).
Lissbrant et al.: Neutralizing VEGF bioactivity with a soluble chimeric VEGF-receptor protein flt(1-3)IgG inhibits testosterone-stimulated prostate growth in castrated mice. Prostate. 58:57-65 (2004).
Maguire et al.: Comparison of Age-related Macular Degeneration Treatments Trials Research. Ophthalmology. 123:1751-1761 (2016).

(56) References Cited

OTHER PUBLICATIONS

Malyala et al.: Endotoxin limits in formulations for preclinical research. J Pharm Sci. 97:2041-2044 (2008).
Markovic-Mueller et al.: Structure of the Full-length VEGFR-1 Extracellular Domain in Complex with VEGF-A. Structure. 25:341-352 (2017).
Miller et al.: Vascular endothelial growth factor a in intraocular vascular disease. Ophthalmology. 120:106-114 (2013).
Morin et al.: Neurodevelopmental Outcomes Following Bevacizumab Injections for Retinopathy of Prematurity. Pediatrics. 137 (2016).
Nguyen et al.: Combercept (KH-902) for the treatment of neovascular age-related macular degeneration. Expert Rev Clin Pharmacol. 8:541-548 (2015).
Olsson et al.: VEGF receptor signalling—in control of vascular function. Nat Rev Mol Cell Biol. 7:359-371 (2006).
Park et al.: Placenta growth factor. Potentiation of vascular endothelial growth factor bioactivity, in vitro and in vivo, and high affinity binding to Flt-1 but not to Flk-1/KDR. J-Biol-Chem. 269:25646-25654 (1994).
Park et al. The vascular endothelial growth factor isoforms (VEGF): Differential deposition into the subepithelial extracellular matrix and bioactivity of extracellular matrix-bound VEGF. Molecular Biology of the Cell. 4:1317-1326 (1993).
PCT/US2019/015160 International Preliminary Report on Patentability dated Jul. 28, 2020.
Plate et al.: Vascular endothelial growth factor is a potential tumour angiogenesis factor in human gliomas in vivo. Nature. 359:845-848 (1992).
Presta et al.: Humanization of an Anti-Vascular Endothelial Growth Factor Monoclonal Antibody for the Therapy of Solid Tumors and Other Disorders. Cancer Res. 57:4593-4599 (1997).
Qu et al.: Ultrastructural localization of vascular permeability factor/vascular endothelial growth factor (VPF/VEGF) to the abluminal plasma membrane and vesiculovacuolar organelles of tumor microvascular endothelium. Journal of Histochemistry & Cytochemistry. 43:381-389 (1995).
Rakoczy et al.: Gene therapy with recombinant adeno-associated vectors for neovascular age-related macular degeneration: 1 year follow-up of a phase 1 randomised clinical trial. Lancet. 386:2395-2403 (2015).
Ratanji et al.: Immunogenicity of therapeutic proteins: influence of aggregation. J Immunotoxicol. 11:99-109 (2014).
Regula et al.: Targeting key angiogenic pathways with a bispecific CrossMAb optimized for neovascular eye diseases. EMBO Mol Med. 8:1265-1288 (2016).
Roberts CJ: Therapeutic protein aggregation: mechanisms, design, and control. Trends Biotechnol. 32:372-380 (2014).
Rodrigues et al.: Functional Characterization of Abicipar-Pegol, an Anti-VEGF DARP in Therapeutic That Potently Inhibits Angiogenesis and Vascular Permeability. Invest Ophthalmol Vis Sci. 59:5836-5846 (2018).
Ruhrberg et al.: Spatially restricted patterning cues provided by heparin-binding VEGF-A control blood vessel branching morphogenesis. Genes Dev. 16:2684-2698 (2002).
Saishin et al.: VEGF-TRAP(R1 R2) suppresses choroidal neovascularization and VEGF-induced breakdown of the blood-retinal barrier. J Cell Physiol. 195:241-248 (2003).
Sankar et al.: Anti-vascular endothelial growth factor (VEGF) drugs for treatment of retinopathy of prematurity. Cochrane Database Syst Rev. 1:CD009734 (2018).
Sarrazin et al.: Heparan sulfate proteoglycans. Cold Spring Harb Perspect Biol. 3(7):a004952 (2011).
Shibuya M.: VEGFR and type-V RTK activation and signaling. Cold Spring Harb Perspect Biol. 5:a009092 (2013).
Silva et al.: Tyrosine kinase blocking collagen IV-derived peptide suppresses ocular neovascularization and vascular leakage. Sci Transl Med. 9 (2017).
Singapore Patent Application No. SG11202007130R Written Opinion dated Mar. 1, 2022.
Smith et al.: Essential role of growth hormone in ischemia-induced retinal neovascularization. Science. 276:1706-1709 (1997).
Smith et al.: Regulation of vascular endothelial growth factor-dependent retinal neovascularization by insulin-like growth factor-1 receptor. Nature Medicine. 5:1390-1395 (1999).
Terman et al.: Identification of the KDR tyrosine kinase as a receptor for vascular endothelial cell growth factor. Biochem-Biophys-Resj-Commun. 187:1579-1586 (1992).
Tischer et al.: The human gene for vascular endothelial growth factor. Multiple protein forms are encoded through alternative exon splicing. Journal of Biological Chemistry. 266:11947-11954 (1991).
U.S. Appl. No. 17/522,318 Office Action dated Jan. 20, 2022.
U.S. Appl. No. 17/522,422 Office Action dated Mar. 29, 2022.
U.S. Appl. No. 17/526,929 Office Action dated Jan. 21, 2022.
Vorum et al.: Real world evidence of use of anti-VEGF therapy in Denmark. Curr Med Res Opin. 1-32 (2016).
Wang et al.: IgG Fc engineering to modulate antibody effector functions. Protein Cell 9:63-73 (2018).
Wiesmann et al.: Crystal structure at 1.7 a resolution of VEGF in complex with domain 2 of the Flt-1 receptor. Cell. 91:695-704 (1997).
Woodard et al.: Heparan Sulfate Binding Promotes Accumulation of Intravitreally Delivered Adeno-associated Viral Vectors at the Retina for Enhanced Transduction by Weakly Invluences Tropism. J Virol. 90:9878-9888 (2016).
Xiao et al.: Fully automated, deep learning segmentation of oxygen-induced retinopathy images. JCI Insight. 2 (2017).
Xin et al.: Evidence for Pro-angiogenic Functions of VEGF-Ax. Cell. 167:275-284 e6 (2016).
Xin et al.: Heparin-binding VEGFR1 variants as long-acting VEGF inhibitors for treatment of intraocular neovascular disorders. PNAS. 118(21):e191252118 (2021).
Yang et al.: Comparison of binding characteristics and in vitro activities of three inhibitors of vascular endothelial growth factor a. Mol Pharm. 11:3421-3430 (2014).
Yang et al.: Comparison of biosensor platforms in the evaluation of high affinity antibody-antigen binding kinetics. Anal Biochem. 508:78-96 (2016).
Yu et al.: Interaction between Bevacizumab and Murine VEGF-A: A Reassessment. Invest Ophthalmol Vis Sci. 49:522-527 (2008).
Zheng et al.: Contribution of vascular endothelial growth factor in the neovascularization process during the pathogenesis of herpetic stromal keratitis. J Virol. 75:9828-9835 (2001).

* cited by examiner $V_{123}$ Amino acid sequence

*MVSYWDTGVLLCALLSCLLILTGSSSGSKLKDPELSLKGTQHIMQAGQTLHLQCRGEAAHKWSLPEMVS*
*KESERLSITKSAGRNGKQFCSTLTLNTAQANHTGFYSCKYLAVPTSKKKETESAIYIFISDTGRPFV*
*EMYSEIPEIIHMTEGRELVIPCRVTSPNITVILKKFPLDTLIPDGKRIIWDSRKGFIISNATYKEIGL*
LTCEATVNGHLYKTNYLTHRQTNTIIDVQISTPRPVKLLRGHTLVLNCTATTPLNTRVQMTWSYPDEK
NKRASVRRRIDQSNSHANIFYSVLTIDKMQNKDKGLYTCRVSGPSFKSVNTSVHIYDKTHTCPPC
PAPELLGGPSVFLFPPKPKDTLMISRTPEVTCVVVDVSHEDPEVKFNWYVDGVEVHNAKTKPREEQYN
TYRVVSVLTVLHQDWLNGKEYKCKVSNKALPAPIEKTISKAKGQPREPQVYTLPPSREEMTKNQVSLT
*VKGFYPSDIAVEWESNGQPENNYKTTPPVLDSDGSFFLYSKLTVDKSRWQQGNVFSCSVMHEALHNLH*
*YTQKSLSLSGK*

Nucleic acid sequence

*ATGGTCAGCTACTGGGACACCGGGGTCCTGCTGTGCGCTCTGCTCAGCTGTCTGCTTCTCACAGGATC*
*TAGTTCAGGTTCAAAATTAAAGGATCCAGAGCTGAGTTTAAAGGCCACCCAGCACATCATGCAAGCAG*
GCCAGACACTGCATCTCCAATGCAGGGGAAGCAGCATAACTAAAATCTGCCTGTGAAGAATGGTGAGT
AAGGAAAGCGAAAGGCTGAGCTTCAAGACACAAGCAATCTGCAATATCTAGCTGTGTCCTA
TTTAACCTTGAAGAAGAAGAAACAGAAYCCCGAAATTTACTTTAAAGAAGTTCCACTTGACAACGTAA
CTTCAAGATGTACAGTGAAAYCCACATCAGAAGAAGGAGCTCGTCATTCCCTGCCG
GAGATGTACAGTGAGATCCCGGAATTATACTGTTACTTTAAAGAAGTTCCACTTGACAACGTA
ACGCCATAATCTGGGACAGCAACAGRCAATGGCATTTGTATAAGACAAACTATCTCACACATGACAAACCAA
CTGACCTGTGAAGCAACTGGCATTTGTATAAGACAAACTATCTCACACATGACAAACCAA

V23 Amino acid sequence

MVSYWDTGVLLCALLSCLLLTGSSSGIFISDTGRPFVEMYSEIPEIIHMTEGRELVIPCRVTSPNITV
TLKKFPLDTLIPDGKRIIWDSRKGFIISNATYKEIGLLTCEATVNGHLYKTNYLTHRQTNTIIDVQIS
TPRPVKLLRGHTLVLNCTATTPLNTRVQMTWSYPDEKNKRASVRRRIDQSNSHANIFYSVLTIDKMQN
KDKGLYTCRVRSGPSFKSVNTSVHIYDKDKTHTCPPCPSPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSNKAL
PAPIEKTISKAKGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPGK

Nucleic acid sequence

ATGGTCAGCTACTGGGACACCGGGGTCCTGCTGTGCGCGCTGCTCTCAGCTGTCTGCTTCTCACAGATC
TAGTTCAGGTATATTTATTAGTGATACAGGGAGACCTTTCGTAGAGATGTACAGTGAAATCCCGAAA
TTATACACATGACTGAAGGAAGGGAGCTCGTTCATVVVTGCCCGGTGGAAAACGCATAATCGGACAGTAGAAA
ACTTTAAAAAAAGTTTCCACTGACAACTTGACAACGTATCTCACAGAGGCTTCTGACCTGTGAAGCAACAGTCAATG
GGGCTTCATCATATCAAAGACAAATCGACAACTCTTGTCCCATGAAAAAATAAGAGAGCTCCTGTAAGGCACA
ACACCACGAGAGTTCAAATGACCTGGAGTTACCCTGGAGTTACCCTGAACATATTCTACAGTGTTCTTACAGTGTTCTTACAGTGACA
GAATTGACCAAAGCAACTTTATACTTTCGTGTGAGTGGACCATCAATCTCAAATCTGTTAACACCTCAGT
AAAGACAAAGGACTTTATACTTTGATAAAGACAAACAAACTCACAGCAAGTCTCAGTTAACACCTCAGT
GCATATATATGATAAAGACAAACATGCCCAGCACCGTGCCCACCGTGAACTCCTGAACTCCTGGGGGAC

FIG. 4

```
CGTCAGTCTTCCTCTTCCCCCAAAACCCAAGGACACCCCTCATGATCTCCCGGACCCCTGAGGTCACA
CGTCAGTCTTCCTCTTCCCCCAAAACCCAAGGACACCCCTCATGATCTCCCGGACCCCTGAGGTCACA
TGCGTGGTGGTGGACGTGAGCCACGAAGACCCTGAGGTCAAGTTCAACTGGTACGTGGACGGCGTGGA
GGTGCATAATGCCAAGACAAAGCCGCGGGAGGAGCAGTACAACAGCACGTACCGTGTGGTCAGCGTCC
TCACCGTCCTGCACCAGGACTGGCTGAATGGCAAGGAGTACAAGTGCAAGGTCTCCAACAAAGCCCTC
CCAGCCCCCATCGAGAAAACCATCTCCAAAGCCAAAGGGCAGCCCCGAGAACCAGGTGTACACCCTGC
CCCCATCCCGGGAGGAGATGACCAAGAACCAGGTCAGCCTGACCTGCCTGGTCAAAGGCTTCTATC
CCAGCGACATCGCCGTGGAGTGGGAGAGCAATGGGCAGCCGGAGAACAACTAXAAGACCACGCCTCCC
GTGCTGGACTCCGACGGCTCCTTCTTCCTCTACAGCAAGCTCACCGTGGACAAGAGCAGGTGGCAGCA
GGGGAACGTCTTCTCATGCTCCGTGATGCATGAGGCTCTGCACAACCACTACACGCAGAAGAGCCTCT
CCCTGTCTCCGGGTAAA
```

| | |
|---|---|
| Signal Peptide | ......... |
| Ig-like Domain 2 | — — — |
| Ig-like Domain 3 | ......... |
| Human IgG-1-Fc Fragment | Black with Underline |

FIG. 4
(Continued)

Amino acid sequence $V_{1233}$: MVSYWDTGVLLCALLSCLLLTGSSSGSKLKDPELSLKGTQHIMQAGQTLHLQCRGEAAHKWSLPEMVS
KESERLSITKSACGRNGKQFCSTKTKNTAQANHTGFYSCKYLAVPTSKKETESAIYIFISDYGRPFV
EMYSEIPEIIHMTEGRELVIPCRVTSPNITVTLKKFPLDTLIPDGKRIIWDSRKGFIISNATYKEIGL
LICEATVNGHLYKTNYLTHRQTNTIIDVQISTPRPVKLLRGHTLVLNCTATTPLNTRVQMTWSYPDEK
NKRASVRRRYDQSNDHANIFYSVLTIDKMQNKDKGLYTCRVRSGPSFKSVNTSVHIYDKAVQISTPRP
VKLLRGHTLVLNCTATTPLNTRVQMTWSYPDEKNKRASVRRRIDQSNSHANIFYSVLTIDKMQNKDKG
LYTCRVRSGPSFKSVNTSVHIYDKDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK Nucleic acid sequence ATGGTCAGCTACTGGGACACCGGGGTCCTGCTGTGCGCGCTGCTGTCTTGCTTCTCACAGGATC
TAGTTCAGGTTCAAAATAAAAGATCCAGGGGAAGCAGCCACCCGAGTTAAAGGCACCATGCAAGCAG
GCCAGAGCACTGCATCTCCAATGCTGAGCAGCAGCCTGAAGTGGTCTTTGCCTGAAATGGTGAGT
AAGGAAAAGCGAAAGGCTAAGAATCTGAACCACACTGGCTTTTACAGCTGCAAAATATCTAGTGCTAC
TTTAACCTTGAACAAGAAGGAAACAGAAATCTGCAATTATACACTTATGAAGGAAGGAGCTCATTCCGAA
CTTCAAGAAGAAGAAAAATCCCCGAAATTATACACTTATTAAAAAAGTTTCCACTTGATCCCTGATGGAA
GAGATGTACAGTGCTACCTGACACTGTTACTTTAAAAAAGTTTCCACTTGATCCCTGATGGAA
GGTTACGTCACCTGACACTGTAGGGCTTCATCATCAAATCAACGTACATCAAAGAAATAGGGCTT
AACGCATAATCTGGGACAGTCAGTCAATGGGCATTTGTATAAGACAAACTATCTCACACGTCGACAACCAA
CTGACCTGTGAACAAGAAGAAGCAACATCAAAGCTAAATCACTGACACAAACCAACCAA

Amino acid sequence

MVSYWDTGVLLCALLSCLLLLTGSSSGIFISDTGRPFVEMYSEIPEIIHMTEGRELVIPCRVISPNITV
TLKKFPLDTLIPDGKRIIWDSRKGFIISNATYKEIGLLTCEATVNGHLYKTNYLTHRQTNTIIDVQIS
TPRPVKLILRGHTLVLNCTATTPLNTRVQMTWSYPDEKNKRASVRRRIDQSNSHANIFYSVLTIDKMQN
KDKGLYTCRVRSGPSFKSVNTSVHIYDKAVQISTPRPVKLLRGHTLVLNCTATTPLNTRVQMTWSYPD
EKNKRASVRRRIDQSNSHANIFYSVLTIDKMQNKDKGLYTCRVRSGPSFKSVNTSVHIYDKDKTHTCP
PCPAPELLGGPSVFLFPPKPKDTLMISRIPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNVFSCSVMHEA
LHNHYTQKSLSLSPGK

Nucleic acid sequence

ATGGTCAGCTACTGGGAGACCGGGGTCCTGCTGTGCGCGCTGCTCAGCTGCCTGCTCCTGCTCACAGGATC
TAGTTCAGGTATATTTATTAGTGATACCGGGAGACCTTTCGTAGAGATGTACAGTGAAATCCCCGAAA
TTATACACATGACTGAAGGAGAGCTCGTCATTCCCTGCCGGGTTATCTCACCTAACACTGTT
ACTTTAAAAAAGTTTCCACACTGATCCCTGATGGAAAACGCATAATCTGGGACAGTAGAAA
GGGCTTCATCATATCAAATGCAACATATTCTGAAGCAAACCAATCATAGATGTCCAATAAGC
ACACCACGCCCAGTCAAATTACTTAGAGACTTCTGAAAAAAATAAGAGAGCTTCCGTAAGGCGAC
GAATTGACCAAAGCAATCTACAGTCCCATGCCAACATATTCTACAGTGTTCTTACTGTTAACATGCAGAAC
AAAGACAAAGGACTTTATACTTGTCGTGTAAGGAGTGGACCATCAAATCTGTTAACACTTCAGT
GCATATATATGATAAGCCAGTCCAAATTACTTAGAGGCCATACTC

FIG. 6

TTGTCCTCAATTGTACTGCTACCACTCCCTTGAACACGAGAGTTCAAATGACCCTGAGTTACCCTGAT
GAAAAAATAAGAGAGCTTCCGTAAGGCGAATTGACCAAAGCAATTCCCAATGCCAACATATTCTA
CAGTGTTCTTACTATTGACAAATGCAGAAGACAAAGACTTTATACTTGTCGTGTAAGGAGTG
GACCATCATTCAAATCTGTTAACACCTCAGTGCATATATGATAAAGACAAAACTCACACATGCCCA
CCGTGCCCAGCACTCCTGGGGACCGTCAGTCTTCCTCTTCCCCCCAAAACCCAAGGACACAC
CCTCATGATCTCCCGGACCCCTGAGGTCACATGCGTGGTGGTGGACGTGAGCCACGAAGACCCTGAGG
TCAAGTTCAACTGGTACGTGGACGGCGTGGAGGTGCATAATGCCAAGACAAAGCCGCGGGAGGAGCAG
TACAACAGCACGTACCGTGTGGTCAGCGTCCTCACCGTCCTGCACCAGGACTGGCTGAATGGCAAGGA
GTACAAGTGCAAGGTCTCCAACAAAGCCCTCCCAGCCCCCATCGAGAAAACCATCTCCAAAGCCAAAG
GGCAGCCCCGAGAACCACAGGTGTACACCCTGCCCCCATCCCGGGAGGAGATGACCAAGAACCAGGTC
AGCCTGACCTGCCTGGTCAAAGGCTTCTATCCCAGCGACATCGCCGTGGAGTGGGAGAGCAATGGGCA
GCCGGAGAACAACTACAAGACCACGCCTCCCGTGCTGGACTCCGACGGCTCCTTCTTCCTCTACAGCA
AGCTCACCGTGGACAAGAGCAGGTGGCAGCAGGGGAACGTCTTCTCATGCTCCGTGATGCACGAGGCT
CTGCACAACCACTACACGCAGAAGAGCCTCTCCCTGTCTCCGGGTAAA

Signal Peptide ........

Ig-like Domain 2 — - — -

Ig-like Domain 3 ........

Human IgG-1-Fc Fragment  <u>Black with Underline</u>

FIG. 6
(Continued)

V_{1234} Amino acid sequence

MVSYWDTGVLLCALLSCLLLTGSSSSGSKLKDPELSLKGTQHIMQAGQTLHLQCRGEAAHKWSLPEMVS
KESERLSITKSACGRNGKQFCSTLTLNTAQANHTGFYSCKYLAVPTSKKKETESAIYIFISDTGRPFV
EMYSEIPEIIHMTEGRELVIPCRVTSPNIVTLKKFPLDTLIPDGKRIIWDSRKGFIISNATYKEIGL
LTCEATVNGHLYKINYLTHRQTNTIIDVQISTPRPVKLLRGHTLVLNCTATTPLNTRVQMIWSYPDEK
NKRASVRRRIDQSNSHANIFYSVLTIDKMQNKDGLYTCRVSGPSFKSVNTSVHIYDKAFITVKHRK
QQVLETVAGKRSYRLSMKVKAFPSPEVVWLKDGLPATEKSARYLTRGYSLIKDVTEEDAGNYTILLS
IKQSNVFKNLTATLIVNVKPDKTHTCPPCPAPELLGGPSVFLFPPKPKDTLMISRTPEVICVVDVSH
EDPEVKFNWYVDGVEVHNAKTKPREEQYNSTYVVSVLTVLHQDWLNGKEYKCKVSNKALPAPIEKTI
SKAKGQPREPQVYTLPPRDELTKNQVSLTCLVKGFYPSDIAVEWESNGQPENNYKTTPPVLDSDGSF
FLYSKLTVDKSRWQQGNVFSCSVMHEALHYTQKSLSPGK

Nucleic acid sequence

ATGGTCAGTCAGTCTACTGGGACACCGGGGTCCTGCTGTGTGCGGCGCTGTCTGCTGCTTCTCACAGGATC
TAGTTCAGGTTCAAAAGATCTAAAAGATCCTGAACTGAGTTTAAAAGGCACCCAGCATCATGCAAGCAG
GCCAGACACTGCATCTCCAATGCAGGGGAAGCAGCAGCCCTGTGAAATCTGCCTGGGAAATGGTGAGT
AAGGAAAGCGAAAGGCTGAGCATAACAAAGTCCGCCATTAACAGCAAAATGTTGCCAAATCTGCAGTAC
TTTAACCTTGAACAGCTGACAGGAAAACAGGAAAACAGAATCTGAAGCTCGTACAGCTGCAAATATCTAGCTGTACCTA
CTTCAAGAGATGTACAGTGAAATCCCGAAATTATACTGTTACTTTAAAAAGTTCCACTTGATCCCTGATGGAA
GAGATGTACGTCACCTGACATGGAGAAAAAGGCTTCATATCAAAGACAACGTCGTCATTTGATCCCTGCCG
GGTTACGTCACCTGACAGTAGAAAAGGCTTCATATCAAAGACAACTATCTCACACTATCTCACATCGACAAACCA
AACGCCATAATCTGGGAACAGTCAATGGGCATTTGTATAAGAACAAACTATCTCACACATCGACAAACCA
TCTGACCTGTGAAGCTCAATGGGCATTTGTATAAGAACAAACTATCTCACACATCGACAAACCA

V234 Amino acid sequence

MVSYWDTGVLLCALLSCLLLTGSSSGFISDTGRPFVEMYSEIPEIIHMTEGRELVIPCRVTSPNITV
TLKKFPLDTLIPDGKRIIWDSRKGFIISNATYKEIGLLTCEATVNGHLYKTNYLTHRQTNTIIDVQIS
TPRPVKLLRGHTLVLNCTATTPLNTRVQMTWSYPDEKNKRASVRRRIDQSNSHANIFYSVLTIDKMQN
KDKGLYTCRVRSGPSFKSVNTSVHIYDKAFITVKHRKQQVLETVAGKRSYRLSMKVKAFPSPEVVWLK
DGLPATEKSARYLTRGYSLIIKDVTEEDAGNYTILLSIKQSNVFKNLTATLIVNVKPDKTHTCPPCPA
PELLGGPSVFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRWQQGNVFSCSVMHEALHNH
YTQKSLSPGK

Nucleic acid sequence

ATGGTCAGCTACTGGGACACCGGGGTCCTGCTGTGTGCGCTGCTCTCAGCTGTCTGCTTCTCACAGGATC
TAGTTCAGGTATATTTATTAGTGATACAGGTAGACCTTTCGTAGAGATGTACAGTGAAATCCCCGAAA
TTATACACATGACTGAAGGAAGGGAGCTCGTCATTCCCTGCCGGGTTACGTCACCTAACATCACTGTT
ACTTTAAAAAAGTTTCCACTTGACAATCAAAGACAACTATCTCCACAGGCATAACCTGTGAAGCAACGCAATG
GGGCTTCATCATATCAAATGCAACTTACAAAGAGATAGGCTTGCTGACCTGTGAAGCAACAGTCAATG
GGCATTTGTATAAGACAAATTACCTTCACTCGACAATCAGACAACCATCTTGTCCTCAATAGAGAGTTCAAATAAG
CACACCGCCCAGTCAGGTTCAAATGATGACCTGGAGTTACCCTGAAAAAATAAGAGAGCTTCCGTAAAATGCAGAAC
GAATTGACCAAGCAATTCCCATGCCAACAGATTCTTACAGTGTTCTTACTGTTCTTACTGACAAATGCAGAAC
AAAGACAAAGGAGACTTTATACTTGTCGTGTAAGGAGTGGACCATCATTCAAATCTGTTAACACCTCAGT

FIG. 8

```
GCATATATATGATAAGCATTCATCACTGTGAAATCATCAGTGCTTGAAACCGTAGCTG
GCAAGCGGTCTTACCGGCTCTTATGAAAGTGAAGGCATTTCCCTCGTCGGCGAAGTTGTATGTTAAA
GATGGGTTACCTGCGACTGAGAAATCTGCTCGCTATTTGACTCGTGGCTACTCGTTAATTATCAAGGA
CGTAACTGAAGAGGATGCAGGAATTATACAATCTTGCGCATAAACAGTCAAATGTGTTAAA
ACCTCACTGCCACTCTAATTGTCAATGTGAAACCGACAAAACTCACACATGCCACCGTGCCAGCA
CCTGAACTCTGGGGACCGTCAGTCGTTGGAGGTCACATGCTGTGCAATAAGTGAGACACCCCTCATGATCTC
CCGGACCCCTGAGGTCACGGCGTGGAGGTCACATGCTCGTGCATAATGCCAAGACCCTGAGGTCAAGTTCAACT
GGTACGTGTGGTCAGCCGTCAGCGTTCCTGCCACCGTCCCTGAGCGTGAATGGCTGAATGGCAGTACAACAGCACG
TACCGTGTGGTCAGCCGTCAGCGTTCCTGCCACCGTCCCCAGCCCCCATCCCGGAGGAGATGACCAAGAACCAGGT
GGTCTCCAACAAAGGCTTCTACCCCAGCGACATCGCCGTGGAGTGGGAGAGCAATGGGCAGCCGGAGAACAA
CTGGTCAAAGACCACGCCTCCCGTGCTGGACTCCGACGGCTCCTTCTTCCTCTACAGCAAGCTCACCGTGG
ACAAGAGCAGGTGGCAGCAGGGGAACGTCTTCTCATGCTCCGTGATGCATGAGGCTCTGCACAACCAC
TACACGCAGAAGAGCCTCTCCCTGTCTCCGGGTAAA
```

Signal Peptide  
Ig-like Domain 2  
Ig-like Domain 3  
Ig-like Domain 4  
Human IgG-1-Fc Fragment    Black with Underline

FIG. 8
(Continued)

V24 Amino acid Sequence

MVSYWDTGVLLCALLSCLLLTGSSSGIFISDTGRPFFVEMYSEIPEIIHMTEGRELVIPCRVTSPNITV
TLKKFPLDTLIPDGKRIIWDSRKGFIISNATYKEIGLLTCEATVNGHLYKTNYLTHRQTNTIIDVFIT
VKHRKQQVLETVAGKRSYRLSMKVKAFPSPEVVWLKDGLPATEKSARYLITRGYSLIIKDVTEEDAGNY
TILLSIKQSNVFKNLTATLIVNKPDKTHTCPPCPAPELLGGPSVFLFPPKPDTLMISRTPEVTCVV
VDVSHEDPEVKFNWYVDGVEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK

Nucleic Acid Sequence

ATGGTCAGCTACTGGGACACCGGGGTCCTGCTGTGTGCGCTGCTCTCAGCTGTGTGCTCTCACAGGATC
TAGTTCAGGTATATTTATTAGTGATACAGGGAGACCTTTCCCTGCCGGTCGTCATTCCCTGACCATCA
TTATACACATGACTGAAGGAGAGCACACTTGTACACAACGTATCTCACACCAACATCCCGAAA
ACTTTAAAAAAGTTTCCACTTGACACCAATCAAATGCCTTGACCCTGTGAAGCAACAGTCATTGG
GGGCTTCATCATAAGACAAACAGCAGGCTCTGCTTGAAGTTGTATGGGTTAAAAGATGGGTTACCGC
GGCATTTGTATAAGACAAACAGCAGGCTCTGCTTGAAGTTGTATGGGTTAAAAGATGGGCTACCGC
GTGAAACATCGAAAGCATTTCCCTCGTGGCTACTGGTTAATTATCAAGGACGTAACTGAAGAATCTG
CTCGCTATTTGACTCGTGGCTACTGTTTAAACAACCTAAAATCAAGGACGTAACTGCAGGAATATT
ACAATCTTGCTGAGCATAAACAGTCAAATGTGTTTAAAAACCTCACTGCCACTCTAATTGTCAATGT

FIG. 9

GAAACCCGACAAAACTCACACATGCCCACCGTGCCCAGCACCTGAACTCCTGGGGGGACCGTCAGTCT
TCCTCTTCCCCCCAAAACCCAAGGACACCCTCATGATCTCCCGGACCCCTGAGGTCACATGCGTGGTG
GTGGACGTGAGCCACGAAGACCCTGAGGTCAAGTTCAACTGGTACGTGGACGGCGTGGAGGTGCATAA
TGCCAAGACAAAGCCGCGGGAGGAGCAGTACAACAGCACGTACCGTGTGGTCAGCGTCCTCACCGTCC
TGCACCAGGACTGGCTGAATGGCAAGGAGTACAAGTGCAAGGTCTCCAACAAAGCCCTCCCAGCCCCC
ATCGAGAAAACCATCTCCAAAGCCAAAGGGCAGCCCCGAGAACCAGGTGTACACCCTGCCCCCATC
CCGGGAGGAGATGACCAAGAACCAGGTCAGCCTGACCTGCCTGGTCAAAGGCTTCTATCCCAGCGACA
TCGCCGTGGAGTGGGAGAGCAATGGGCAGCCGGAGAACAACTACAAGACCACGCCTCCCGTGCTGGAC
TCCGACGGCTCCTTCTTCCTCTACAGCAAGCTCACCGTGGACAAGAGCAGGTGGCAGCAGGGGAACGT
CTTCTCATGCTCCGTGATGCATGAGGCTCTGCACAACCACTACACGCAGAAGAGCCTCTCCCTGTCTC
CGGGTAAA

Signal Peptide            ........
Ig-like Domain 2          -- -- --
Ig-like Domain 4          -- -- -- --
Human IgG-1-Fc Fragment   Black with Underline FIG. 9
(Continued)

Log Concentration of VEGF (ng/ml)

Log Concentration of VEGF (ng/ml)

METHODS AND COMPOSITIONS FOR TREATMENT OF ANGIOGENIC DISORDERS USING ANTI-VEGF AGENTS

CROSS REFERENCE TO RELATED APPLICATIONS

This application claims the priority benefit of PCT/US2019/015160 filed on Jan. 25, 2019 which claims the priority benefit of U.S. Provisional Application No. 62/622,382, filed Jan. 26, 2018, which applications are incorporated herein by reference.

SEQUENCE LISTING

The instant application contains a Sequence Listing which has been submitted electronically in ASCII format and is hereby incorporated by reference in its entirety. Said ASCII copy, created on Jan. 25, 2019, is named 24978-0470_SL.txt and is 50,960 bytes in size.

BACKGROUND

The development of a neovascular supply or angiogenesis serves crucial homeostatic roles since the blood vessels carry nutrients to tissues and organs and remove catabolic products[1]. However, uncontrolled growth of blood vessels can promote or facilitate numerous disease processes, including tumors and intraocular vascular disorders[1]. Although several angiogenic factors were initially identified and characterized (e.g., EGF, TGF-α, TGF-β, aFGF, bFGF, angiogenin)[2], work conducted over the last three decades has established the critical role of VEGF-A (VEGF hereafter) in normal and pathological angiogenesis[3,4]. VEGF is a member of a gene family that also includes PlGF, VEGF-B, VEGF-C and VEGF-D. Three related receptor tyrosine kinase (RTKs) have been reported to bind VEGF ligands: VEGFR-1, VEGFR-2 and VEGFR-3[5]. PlGF and VEGF-B interact selectively with VEGFR-1, VEGF binds both VEGFR-1 and VEGFR-2. A third member of this family of RTKs, VEGFR-3[6], binds VEGF-C and VEGF-D, which are implicated in lymphangiogenesis. Each member of this RTK class has seven immunoglobulin (Ig)-like domains in the extracellular portion[7]. There is agreement that VEGFR-2 is the main signaling receptor for VEGF[5]. However, VEGFR-1 binds VEGF with substantially higher binding affinity than VEGFR-2[7].

VEGF inhibitors have become a standard of therapy in multiple tumors and have revolutionized the treatment of intraocular neovascular disorders such as the neovascular form of age-related macular degeneration (AMD), proliferative diabetic retinopathy and retinal vein occlusion, which are leading causes of severe vision loss and legal blindness[8,4]. Currently, three anti-VEGF drugs are widely used in the USA for ophthalmological indications: bevacizumab, ranibizumab and aflibercept[4]. Bevacizumab is a full-length IgG antibody targeting VEGF[9]. Even though bevacizumab was not developed for ophthalmological indications, it is widely used off-label due to its low cost. Ranibizumab is an affinity-matured anti-VEGF Fab[10]. Aflibercept is an IgG-Fc fusion protein[11,12], with elements from VEGFR-1 and VEGFR-2, that binds VEGF, PlGF and VEGF-B[13] Conbercept is a soluble VEGF receptor structurally related to aflibercept, widely used as treatment of intraocular neovascularization in China[14]. Millions of patients worldwide have been treated with these drugs. Importantly, after five-year treatment with ranibizumab or bevacizumab, about half of neovascular AMD patients had good vision, i.e. visual acuity 20/40 or better, an outcome that would have been out of reach before anti-VEGF agents were available[15].

However, in real-life clinical settings, many patients receive fewer anti-VEGF injections than in clinical trials and it has been hypothesized that this may correlate with poor visual outcomes[16]. Indeed, the need to perform relatively frequent intravitreal injections has hampered patient compliance and ultimately the benefits of the therapy, especially in some countries[16]. Therefore, there is a need to develop agents with longer duration when injected in the eye, thus reducing the frequency of injections and a number of approaches to this end have been attempted[17,18]. Aflibercept (EYLEA) was approved based on clinical trials showing that every 8-week administration of the dose of 2 mg could match the efficacy of monthly ranibizumab (0.5 mg). However, despite the prediction that a switch to aflibercept would reduce the number of intravitreal injections, recent studies suggest that it is not the case[19]. Therefore, there is still an unmet medical need for intravitreal anti-VEGF agents with improved half-life.

In 1996 Davis-Smyth et al[20] (see also U.S. Pat. No. 5,952,199) reported that domain (D) 2 of VEGFR-1 is the critical binding element for VEGF and PIGF. Deletion of D2 completely abolished binding. Replacing D2 of VEGFR-3 with VEGFR-1 D2 conferred on VEGFR-3 the ligand specificity of VEGFR-1[20]. Subsequent work documented the interaction between D2 and VEGF (or PlGF) by X-ray crystallography[21-23].

The initial studies led to the design of a construct with full VEGF binding characteristics, comprising the first three Ig-like Ds of VEGFR-1, fused to an Fc-IgG (Flt-1-3-IgG)[20]. Flt-1-3-IgG showed a potent ability to neutralize VEGF, in vitro and in vivo[24-27] However, the systemic half-life of this molecule was hampered by the presence of D3, which has significant heparin affinity due to the presence of clusters of basic residues, resulting in binding to HSPGs in various tissues. In 2002 Holash et al[13] (U.S. Pat. No. 7,070,959) described an IgG fusion construct comprising of VEGFR-1 D2 (the binding element) and D3 of VEGFR2, which has much weaker heparin affinity compared to VEGFR-1 D3. This molecule, known today as aflibercept (marketed as EYLEA), was reported to have a longer half-life compared to Flt-(1-3-IgG) following systemic administration[13], clearly an advantage for treatment aiming, for example, at oncological indications.

SUMMARY OF THE INVENTION

The present invention provides compositions and methods for inhibiting angiogenesis and for treating VEGF-associated conditions, such as ocular disease, including but not limited to, age-related macular degeneration, proliferative diabetic retinopathy, retinal vein occlusion, choroidal neovascularization secondary to myopia, retinopathy of prematurity, diabetic macular edema, polypoidal choroidal vasculopathy, comprising administering an anti-VEGF agent that inhibits the activity of VEGF and, at the same time, has strong heparin-binding characteristics, thereby providing superior pharmacokinetics, namely having a longer half-life of the therapeutic agent following intravitreal administration.

In embodiments, the present invention provides compositions and methods of treating conditions in which local direct administration of an anti-VEGF agent is beneficial, for example, treating and preventing endothelial cell proliferative conditions or angiogenesis, for example, in treating solid tumors, such as but not limited to, intracranial administration in glioblastomas.

In embodiments, the present invention provides an anti-VEGF agent, wherein the anti-VEGF agent is an Fc-IgG construct fusing domains with VEGF binding characteristics and domains that bind heparin proteoglycans. In embodiments, the present invention provides an anti-VEGF agent, wherein the anti-VEGF agent is an Fc-IgG construct having the ability to bind heparin and contains one or more domains with VEGF binding characteristics. In embodiments, the present invention provides an anti-VEGF agent, wherein the anti-VEGF agent is a fusion protein with improved efficacy for binding to VEGF and heparin. In embodiments, the present invention provides an anti-VEGF agent, wherein the anti-VEGF agent is a fusion protein with very low endotoxin levels.

In embodiments, the present invention provides an anti-VEGF agent, wherein the anti-VEGF agent is an IgG chimeric protein comprising elements of VEGF receptors. In embodiments, the present invention provides an IgG chimeric protein, wherein the IgG chimeric protein comprises one or more fragments of the seven immunoglobulin (Ig)-like domains in the extracellular portion of VEGF tyrosine kinase receptors. In embodiments, the present invention provides an IgG chimeric protein, wherein the IgG chimeric protein comprises one or more extracellular domain fragments of VEGFR-1 fused with Fc-IgG. In embodiments, the present invention provides an IgG chimeric protein comprising at least one VEGF binding domain VEGFR-1 domain 2 and at least one additional VEGFR-1 domain 1 or 3, and not including domain 4. In embodiments, the present invention provides an IgG chimeric protein, wherein the IgG chimeric protein comprises one or more extracellular domain fragments of VEGFR-2 fused with Fc-IgG. In embodiments, the present invention provides an IgG chimeric protein, wherein the IgG chimeric protein comprises one or more extracellular domain fragments of VEGFR-1 and VEGFR-2 fused with Fc-IgG.

In embodiments, the present invention provides an anti-VEGF agent comprising a VEGF binding portion operatively linked to a Fc-IgG, wherein the VEGF binding portion comprises at least one VEGF binding domain that is an IgG-like domain 2 of VEGFR-1, and wherein the anti-VEGF agent has a VEGF-stimulated mitogenesis-inhibiting ability greater than aflibercept. In embodiments, the present invention provides that the anti-VEGF agent has a vitreous binding ability greater than aflibercept. In embodiments, the present invention provides that the anti-VEGF agent has a vitreous bound VEGF-stimulated endothelial cell proliferation-inhibiting ability greater than aflibercept. In embodiments, the present invention provides that the agent has an increased half-life in vivo compared to aflibercept.

In embodiments, the present invention provides that the VEGF binding portion consists essentially of IgG-like domains 1, 2, and 3 of VEGFR-1 ($V_{1-2-3}$). In embodiments, the anti-VEGF agent comprises amino acid sequence as defined in SEQ ID NO: 1.

In embodiments, the present invention provides that the VEGF binding portion consists essentially of IgG-like domains 2 and 3 of VEGFR-1 ($V_{2-3}$). In embodiments, the anti-VEGF agent comprises amino acid sequence as defined in SEQ ID NO: 3.

In embodiments, the present invention provides that the VEGF binding portion consists essentially of IgG-like domains 1, 2, 3 and 3 of VEGFR-1 ($V_{1-2-3-3}$). In embodiments, the anti-VEGF agent comprises amino acid sequence as defined in SEQ ID NO: 5.

In embodiments, the present invention provides that the VEGF binding portion consists essentially of IgG-like domains 2, 3 and 3 of VEGFR-1 ($V_{2-1-3}$). In embodiments, the the anti-VEGF agent comprises amino acid sequence as defined in SEQ ID NO: 7.

In embodiments, the present invention provides pharmaceutical compositions comprising a therapeutically effective amount of an anti-VEGF agent as defined claims and a pharmaceutically acceptable excipient. In embodiments, the present invention provides methods of treating a VEGF-related disorder in a subject in need comprising administering to the subject a therapeutically effective amount of an anti-VEGF agent as defined. The anti-VEGF agent can be directly injected into the affected tissue or organ, such as an eye.

In embodiments, the present invention provides a method for treating ocular disease, wherein an anti-VEGF agent is administered locally to the eye at a dosage corresponding to a molar ratio of 2:1 compared to VEGF. In embodiments, the present invention provides a method for treating ocular disease, wherein an anti-VEGF agent is administered by intravitreous injection. In embodiments, the present invention provides a method for treating ocular disease, wherein an anti-VEGF agent is administered every 4-6 weeks, and in other embodiments, the treatment is continued for a period of at least one year.

According to one embodiment, the present invention provides a method for treating ocular disease comprising administering a therapeutically effective amount of an anti-VEGF agent locally into the eye wherein the treatment is effective to treat occult, minimally classic, and predominantly classic forms of wet macular degeneration, wherein the agent is a fusion protein.

In embodiments the invention can be used to treat a wide variety of VEGF-related disorders including neovascular age related macular degeneration, choroidal neovascularization secondary to myopia, proliferative diabetic retinopathy, diabetic macular edema, retinal vascular obstruction such as retinal vein occlusion, ocular tumors, von Hippel Lindau syndrome, retinopathy of prematurity, polypoid choroidal vasculopathy, colorectal cancer, lung cancer, cervical cancer, endometrial cancer, ovarian cancer, kidney cancer, schwannomas, gliomas, ependimomas, and neoplastic or non-neoplastic disorders that benefit from anti-VEGF therapy.

According to another aspect, the present invention provides a pharmaceutical formulation comprising an anti-VEGF agent in a pharmaceutically acceptable carrier formulation for local administration such as into the eye.

In embodiments, the present invention discloses novel constructs, wherein the constructs potently neutralize the activity of VEGF while, at the same time, have strong heparin-binding characteristics.

BRIEF DESCRIPTION OF THE DRAWINGS

A better understanding of the features and advantages of the present disclosure will be obtained by reference to the following detailed description that sets forth illustrative embodiments, in which the principles of the disclosure are utilized, and the accompanying drawings of which:

FIG. 3 depicts the amino acid sequence and nucleic acid sequence of construct $V_{1-2-3}$. SEQ ID NO: 1 and SEQ ID NO: 2, respectively.

FIG. 4 depicts the amino acid sequence and nucleic acid sequence of construct $V_{2-3}$. SEQ ID NO: 3 and SEQ ID NO: 4, respectively.

FIG. 6 depicts the amino acid sequence and nucleic acid sequence of construct $V_{2-3}$. SEQ ID NO: 7 and SEQ ID NO: 8, respectively.

FIG. 7 depicts the amino acid sequence and nucleic acid sequence of construct $V_{1-2-3-3-4}$. SEQ ID NO: 9 and SEQ ID NO: 10, respectively.

FIG. 8 depicts the amino acid sequence and nucleic acid sequence of construct $V_{2-3-4}$. SEQ ID NO: 11 and SEQ ID NO: 12, respectively.

FIG. 9 depicts the amino acid sequence and nucleic acid sequence of construct $V_{2-4}$. SEQ ID NO: 13 and SEQ ID NO: 14, respectively.

FIG. 17B shows representative CD31 immunofluorescence images of groups in FIG. 17A.

DETAILED DESCRIPTION

Figure 1:
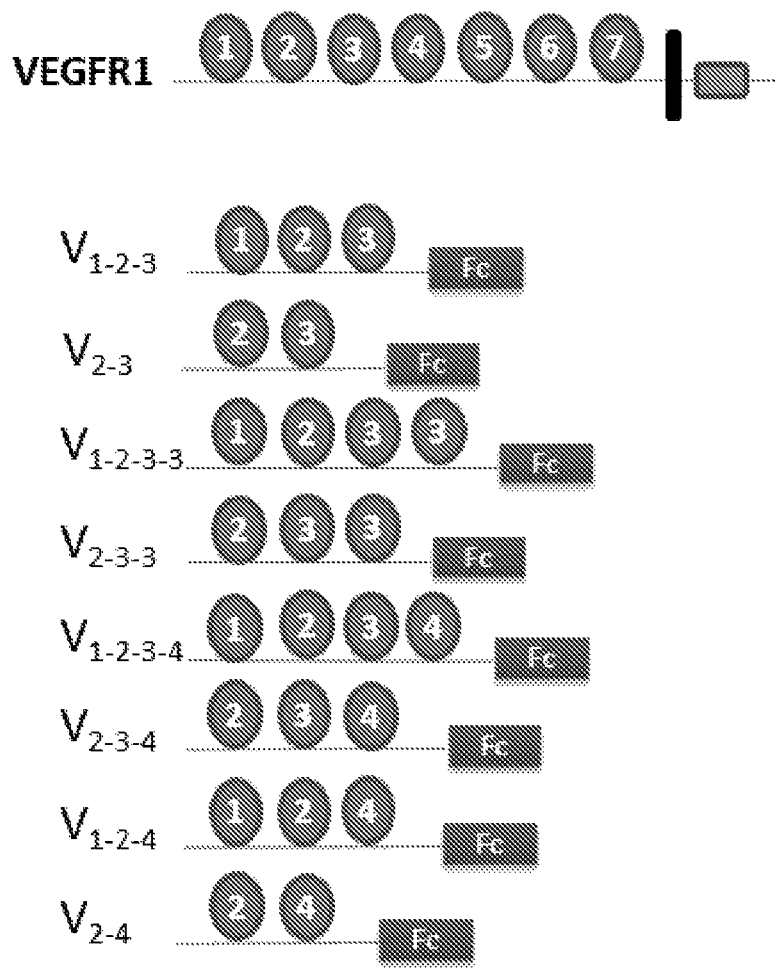
FIG. 1 depicts a schematic representation of exemplary constructed fusion proteins with various Ig-like extracellular domains of VEGFR-1 (V) fused to Fc-IgG (Fc). The following constructs are shown: $V_{1-2-3}$-Fc; $V_{2-3}$-Fc; $V_{1-2-3-3}$-Fc; $V_{2-3-3}$-Fc; $V_{1-2-3-4}$-Fc; $V_{2-3-4}$-Fc; $V_{1-2-4}$-Fc and $V_{2-4}$-Fc.

All publications, patents, and patent applications mentioned in this specification are incorporated herein by reference to the same extent as if each individual publication, patent, or patent application was specifically and individually indicated to be incorporated by reference.

It is understood that aspects and embodiments of the invention described herein include "consisting" and/or "consisting essentially of" aspects and embodiments. Other objects, advantages and features of the present invention will become apparent from the following specification taken in conjunction with the accompanying figures.

When introducing elements of the present invention or the preferred embodiment(s) thereof, the articles "a," "an," "the," and "said" are intended to mean that there are one or more of the elements. The terms "comprising," "including," and "having" are intended to be inclusive and mean that there may be additional elements other than the listed elements.

As used herein, the terms "comprises," "comprising," "includes," "including," "has," "having," "contains", "containing," "characterized by," or any other variation thereof, are intended to encompass a non-exclusive inclusion, subject to any limitation explicitly indicated otherwise, of the recited components. For example, a fusion protein, a pharmaceutical composition, and/or a method that "comprises" a list of elements (e.g., components, features, or steps) is not necessarily limited to only those elements (or components or steps), but may include other elements (or components or steps) not expressly listed or inherent to the fusion protein, pharmaceutical composition and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a fusion protein, pharmaceutical composition, and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

As used herein, the term "pharmaceutical composition" contemplates compositions comprising one or more therapeutic agents or drugs as described below, and one or more pharmaceutically acceptable excipients, carriers, or vehicles.

As used herein, the term "pharmaceutically acceptable excipients, carriers, or vehicles" comprises any acceptable materials, and/or any one or more additives known in the art. As used herein, the term "excipients," "carriers," or "vehicle" refer to materials suitable for drug administration through various conventional administration routes known in the art. Excipients, carriers, and vehicles useful herein include any such materials known in the art, which are nontoxic and do not interact with other components of the composition in a deleterious manner, and generally refers to an excipient, diluent, preservative, solubilizer, emulsifier, adjuvant, and/or vehicle with which an active agent or drug is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art.

As used herein, the term "therapeutically effective amount" refers to those amounts that, when administered to a particular subject in view of the nature and severity of that subject's condition, will have a desired therapeutic effect, e.g., an amount which will cure, prevent, inhibit, or at least partially arrest or partially prevent a target condition. In some embodiments, the term "therapeutically effective amount" or "effective amount" refers to an amount of a therapeutic agent or drug that when administered alone or in combination with an additional therapeutic agent or drug to a cell, tissue, organ, or subject is effective to prevent or ameliorate ocular diseases and cancers, including, but not limited to, age-related macular degeneration, proliferative diabetic retinopathy, retinal vein occlusion, choroidal neovascularization secondary to myopia; retinopathy of prematurity, diabetic macular edema, polypoidal choroidal vasculopathy, colorectal cancer, lung cancer, breast cancer, pancreatic cancer, and prostate cancer. A therapeutically effective dose further refers to that amount of the therapeutic agent or drug sufficient to result in amelioration of symptoms, e.g., treatment, healing, prevention, or amelioration of the relevant medical condition, or an increase in rate of treatment, healing, prevention, or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously.

As used herein, the terms "treating," "treatment," or "alleviation" refers to therapeutic treatment wherein the object is to slow down (lessen) if not cure the targeted pathologic condition or disorder or prevent recurrence of the condition. A subject is successfully "treated" if, after receiving a therapeutic amount of a therapeutic agent or drug, the subject shows observable and/or measurable reduction in or absence of one or more signs and symptoms of the particular condition. Reduction of the signs or symptoms of a condition may also be felt by the subject. A subject is also considered treated if the subject experiences stable condition. In some embodiments, treatment with a therapeutic agent or drug is effective to result in the subjects being symptom-free 3 months after treatment, preferably 6 months, more preferably one year, even more preferably 2 or more years post treatment. These parameters for assessing successful treatment and improvement in the condition are readily measurable by routine procedures familiar to a physician of appropriate skill in the art.

As used herein, "preventative" treatment is meant to indicate a postponement of development of a condition or a symptom of a condition, suppressing symptoms that may appear, or reducing the risk of developing or recurrence of a condition or symptom. "Curative" treatment includes reducing the severity of or suppressing the worsening of an existing symptom, or condition.

As used herein, the term "therapeutic agent," "anti-VEGF agent," "fusion protein," "chimeric protein," or "recombinant protein" comprises a first polypeptide operatively linked to a second polypeptide, wherein the "therapeutic agent," "anti-VEGF agent," "fusion protein," "chimeric protein," or "recombinant protein" inhibits the activity of VEGF. Chimeric proteins may optionally comprise a third, fourth or fifth or other polypeptide operatively linked to a first or second polypeptide. Chimeric proteins may comprise two or more different polypeptides. Chimeric proteins may comprise multiple copies of the same polypeptide. Chimeric proteins may also comprise one or more mutations in one or more of the polypeptides. Methods for making chimeric proteins are well known in the art. In some embodiments the term "therapeutic agent," "fusion protein," "chimeric protein," or "recombinant protein" refers to any constructs expressed or synthesized, including but not limited to, peptides or proteins operatively linking one or more of the Ig-like domains or domain fragments of VEGFR-1 and/or VEGFR-2 with Fc-IgG.

The term "Ig-like domains" refers to Ig-like domains 1-7 of VEGFR-1 and VEGFR-2. The term "Ig-like domain fragments" comprise a portion of a full length domain, generally the heparin and/or VEGF binding or variable region thereof. Examples of domain fragments include amino acid sequences comprising a segment of at least 75%, more preferably at least 80%, 90%, 95%, and most preferably 99% of the full length domain with 100% sequence identity and variations thereof. Variations in the amino acid sequences of fusion proteins are contemplated as being encompassed by the present disclosure, providing that the variations in the amino acid sequence maintain at least 75%, more preferably at least 80%, 90%, 95%, and most preferably 99%. Certain percentages in between are included, such as 75%, 76%, 77%, 78%, 79% 80%, 81%, 82%, 83%, 84%, 85%, 86%, 87%, 88%, 89%, 90%, 91%, 92%, 93%, 94%, 95%, 96%, 97%, 98%, and 99% sequence identity. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional fusion protein can readily be determined by assaying the specific activity of the fusion protein derivative. Fragments or analogs of fusion proteins can be readily prepared by those of ordinary skill in the art.

Preferred amino- and carboxy-termini of fragments or analogs occur near boundaries of functional domains.

As used herein, an "isolated" or "purified" fusion protein means the fusion protein is the predominant species present (i.e., on a molar basis it is more abundant than any other individual species in the composition), and preferably a substantially purified fraction is a composition wherein the fusion protein comprises at least about 50% (on a molar basis) of all macromolecular species present. Generally, a purified composition will comprise more than about 80% of all macromolecular species present in the composition, more preferably more than about 85%, 90%, 95%, and 99%. Most preferably, the fusion protein is purified to essential homogeneity (contaminant species cannot be detected in the composition by conventional detection methods) wherein the composition consists essentially of a single macromolecular species.

Values or ranges may be expressed herein as "about," from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value, or within 2% of the recited value.

In one aspect the present invention discloses a composition comprising a therapeutic agent, where the therapeutic agent comprises one or more heparin binding domains of VEGFR-1 or VEGFR-2, and one or more VEGF binding domains, thereby inhibiting the binding of VEGF to its cognate receptor.

In embodiments, the present invention provides an anti-VEGF agent comprising a VEGF binding portion operatively linked to a Fc-IgG, wherein the VEGF binding portion comprises at least one VEGF binding domain that is an IgG-like domain 2 of VEGFR-1, and wherein the anti-VEGF agent has a VEGF-stimulated mitogenesis-inhibiting ability greater than aflibercept. In embodiments, the present invention provides that the anti-VEGF agent has a vitreous binding ability greater than aflibercept. In embodiments, the present invention provides that the anti-VEGF agent has a vitreous bound VEGF-stimulated endothelial cell proliferation-inhibiting ability greater than aflibercept. In embodiments, the present invention provides that the agent has an increased half-life in vivo compared to aflibercept.

In embodiments, the present invention provides that the VEGF binding portion consists essentially of IgG-like domains 1, 2, and 3 of VEGFR-1 ($V_{1-2-3}$). In embodiments, the anti-VEGF agent comprises amino acid sequence as defined in SEQ ID NO: 1.

In embodiments, the present invention provides that the VEGF binding portion consists essentially of IgG-like domains 2 and 3 of VEGFR-1 ($V_{2-3}$). In embodiments, the anti-VEGF agent comprises amino acid sequence as defined in SEQ ID NO: 3.

In embodiments, the present invention provides that the VEGF binding portion consists essentially of IgG-like domains 1, 2, 3 and 3 of VEGFR-1 ($V_{1-2-3-3}$). In embodiments, the anti-VEGF agent comprises amino acid sequence as defined in SEQ ID NO: 5.

In embodiments, the present invention provides that the VEGF binding portion consists essentially of IgG-like domains 2, 3 and 3 of VEGFR-1 ($V_{2-3-3}$). In embodiments, the anti-VEGF agent comprises amino acid sequence as defined in SEQ ID NO: 7.

In embodiments, the present invention provides pharmaceutical compositions comprising a therapeutically effective amount of an anti-VEGF agent as defined claims and a pharmaceutically acceptable excipient. In embodiments, the present invention provides methods of treating a VEGF-related disorder in a subject in need comprising administering to the subject a therapeutically effective amount of an anti-VEGF agent as defined. The anti-VEGF agent can be directly injected into the affected tissue or organ, such as an eye.

In embodiments the invention can be used to treat a wide variety of VEGF-related disorders including neovascular age related macular degeneration, choroidal neovascularization secondary to myopia, proliferative diabetic retinopathy, diabetic macular edema, retinal vascular obstruction such as retinal vein occlusion, ocular tumors, von Hippel Lindau syndrome, retinopathy of prematurity, polypoid choroidal vasculopathy, colorectal cancer, lung cancer, cervical cancer, endometrial cancer, ovarian cancer, kidney cancer, schwannomas, gliomas, ependimomas, and neoplastic or non-neoplastic disorders that benefit from anti-VEGF therapy.

In some embodiments, the therapeutic agent is in an administrable dosage form, comprising the therapeutic agent, and an additional excipient, carrier, adjuvant, solvent, or diluent.

In some embodiments, the present invention discloses a pharmaceutical composition suitable for treating and/or preventatively treating a subject, wherein the therapeutic agent is contained in an amount effective to achieve its intended purpose.

In some embodiments, the therapeutic agent or compositions disclosed herein are administered by injection. In certain embodiments, the compositions or the therapeutic agent are injected directly into the diseased organ or tissue. In some embodiments, the therapeutic agent can be topically administered, for example, by patch or direct application to the diseased organ or tissue, or by iontophoresis. The therapeutic agents may be provided in sustained release compositions, such as those described in, for example, U.S. Pat. Nos. 5,672,659 and 5,595,760. The use of immediate or sustained release compositions depends on the nature of the condition being treated. If the condition consists of an acute or over-acute disorder, treatment with an immediate release form will be preferred over a prolonged release composition. Alternatively, for certain preventative or long-term treatments, a sustained released composition may be appropriate.

The therapeutic agent may also be delivered using an implant, such as but not limited to an intraocular implant. Such implants may be biodegradable and/or biocompatible implants, or may be non-biodegradable implants. The implants may be permeable or impermeable to the active agent. The specific implants for delivery of the therapeutic agent is dependent on both the affected tissue or organ as well as the nature of the condition being treated. The use of such implants is well known in the art.

The inhibitors described in this invention can be formulated in nanoparticles or other drug formulations in order to provide precise delivery to specific tissues and also provide controlled release therapy.

The inhibitors described in this application can be delivered not only as purified recombinant proteins but also by a gene therapy approach. Recombinant adeno-associated vectors (rAAVs) or other suitable vectors can be used to deliver the VEGF inhibitor by sub-retinal or intravitreal delivery[43,44].

In a related aspect, the present invention provides a method for treating a VEGF-related or neovascular disorder in a subject, wherein the method involves administering to the subject: (a) an effective amount of a fusion protein capable of binding heparin and diminishing or preventing the development of unwanted neovasculature. The fusion protein may be combined with other anti-VEGF agents including, but are not limited to: antibodies or antibody fragments specific to VEGF; antibodies specific to VEGF receptors; compounds that inhibit, regulate, and/or modulate tyrosine kinase signal transduction; VEGF polypeptides; oligonucleotides that inhibit VEGF expression at the nucleic acid level, for example antisense RNAs; and various organic compounds and other agents with angiogenesis inhibiting activity.

The invention provides that heparin-binding mediated by D3 (or other Ig-like domain) of VEGFR1[28], while a disadvantage for systemic administration, can confer important advantages for intravitreal (or other local) administration. Indeed, the ability to bind HGPSG, key components of the extracellular matrix[29], promotes accumulation in the vitreous as well as retinal penetration[30]. The invention provides a series of VEGFR-1 Fc fusion constructs having differential abilities to interact with HSPGs. This enables election of VEGF inhib9itors with different duration/half life in the eye, which are useful under difference clinical conditions.

The features and other details of the invention will now be more particularly described and pointed out in the following examples describing preferred techniques and experimental results. The examples are provided for the purpose of illustrating the invention and should not be construed as limiting.

EXAMPLES

In embodiments, the present invention therefore discloses anti-VEGF agents that are novel and improve on existing anti-VEGF agents, including aflibercept, owing to high biological potency combined with strong heparin-binding characteristics. The heparin binding is predictive of a longer half-life and consequently reduced frequency of administration.

The invention provides that heparin-binding mediated by D3 (or other Ig-like domain) of VEGFR1[28], while a disadvantage for systemic administration, can confer important advantages for intravitreal (or other local) administration. Indeed, the ability to bind HGPSG, key components of the extracellular matrix[29], may promote accumulation in the vitreous as well as retinal penetration[30]. The invention provides a series of VEGFR-1 Fc fusion constructs having differential abilities to interact with HSPGs.

Figure 2:
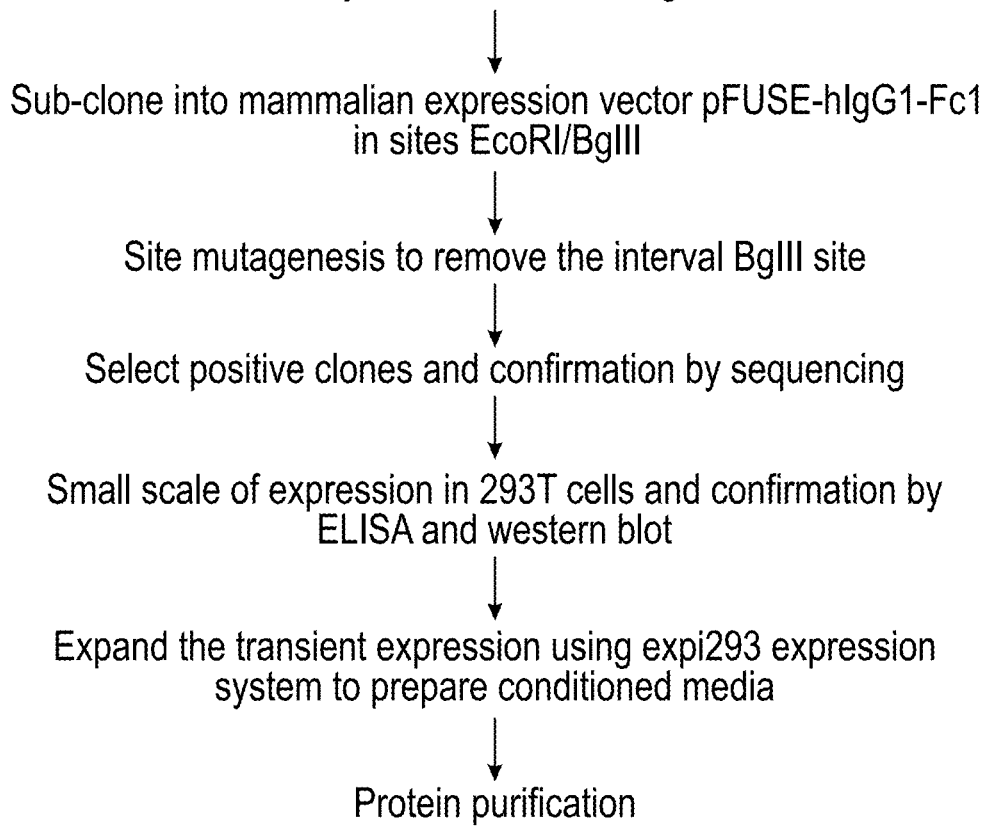
FIG. 2 depicts a strategy of plasmid construction and expression.
Figure 2:
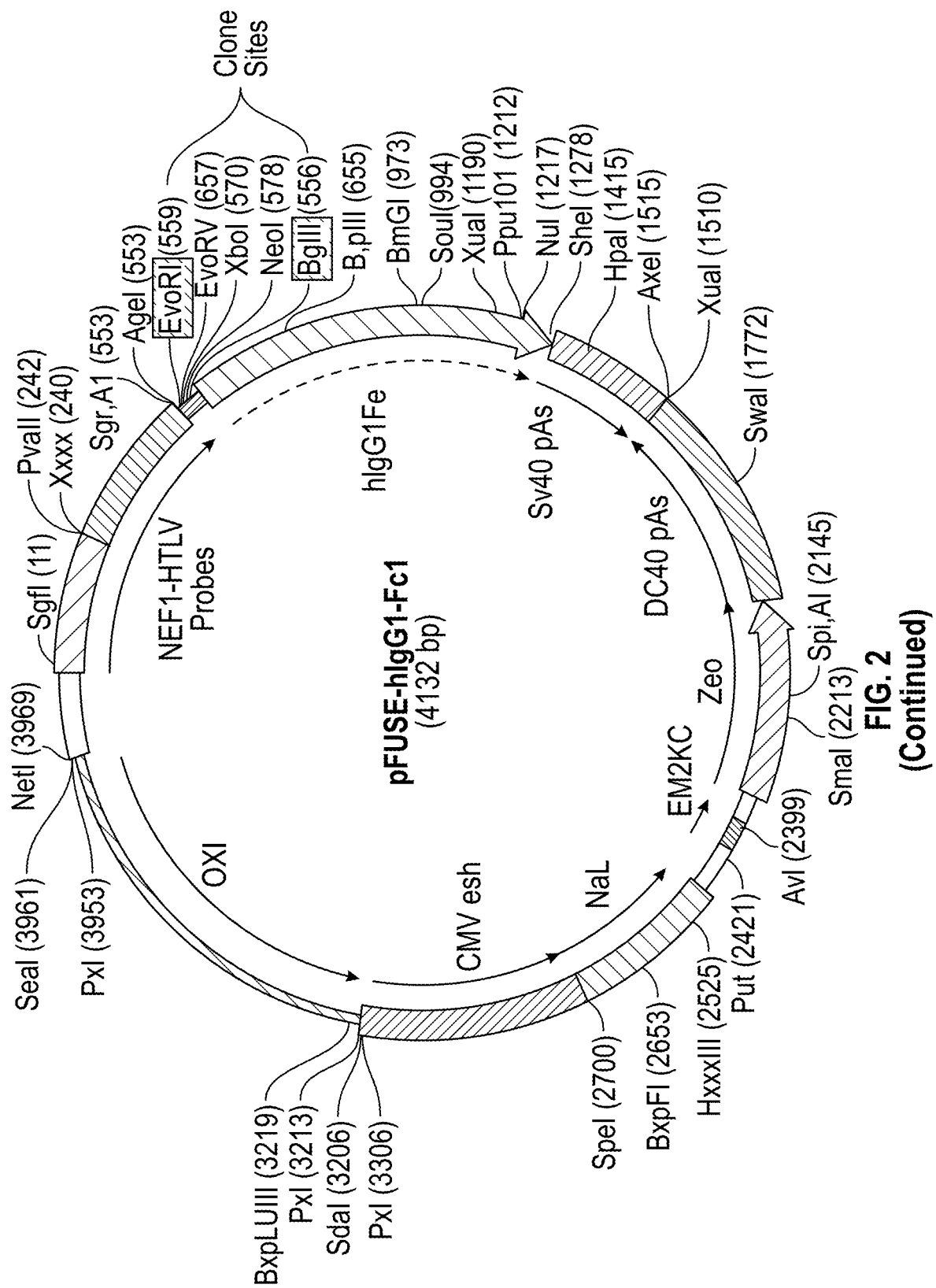
Figure 3:
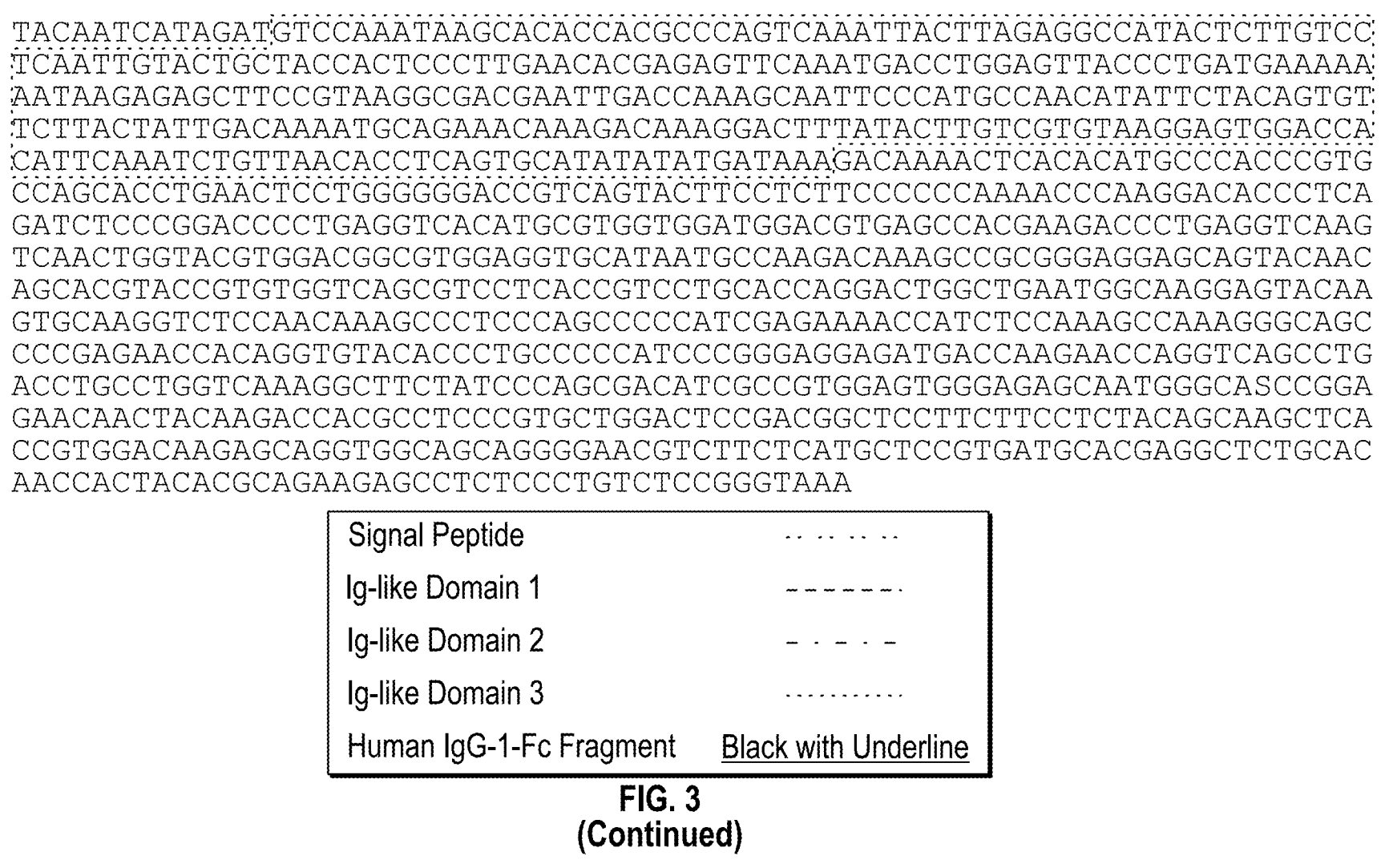
Figure 5:
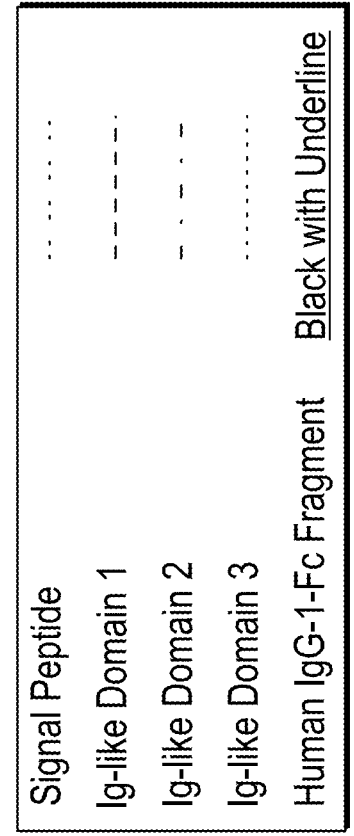
FIG. 5 depicts the amino acid sequence and nucleic acid sequence of construct $V_{1-2-3-3}$. SEQ ID NO: 5 and SEQ ID NO: 6, respectively.

FIG. 1 provides a schematic representation of the constructs employed here. FIG. 2 illustrates the vector employed and the cloning strategy. FIG. 3-9 show the nucleic acid and amino acid sequences of the constructs generated.

Figure 10:
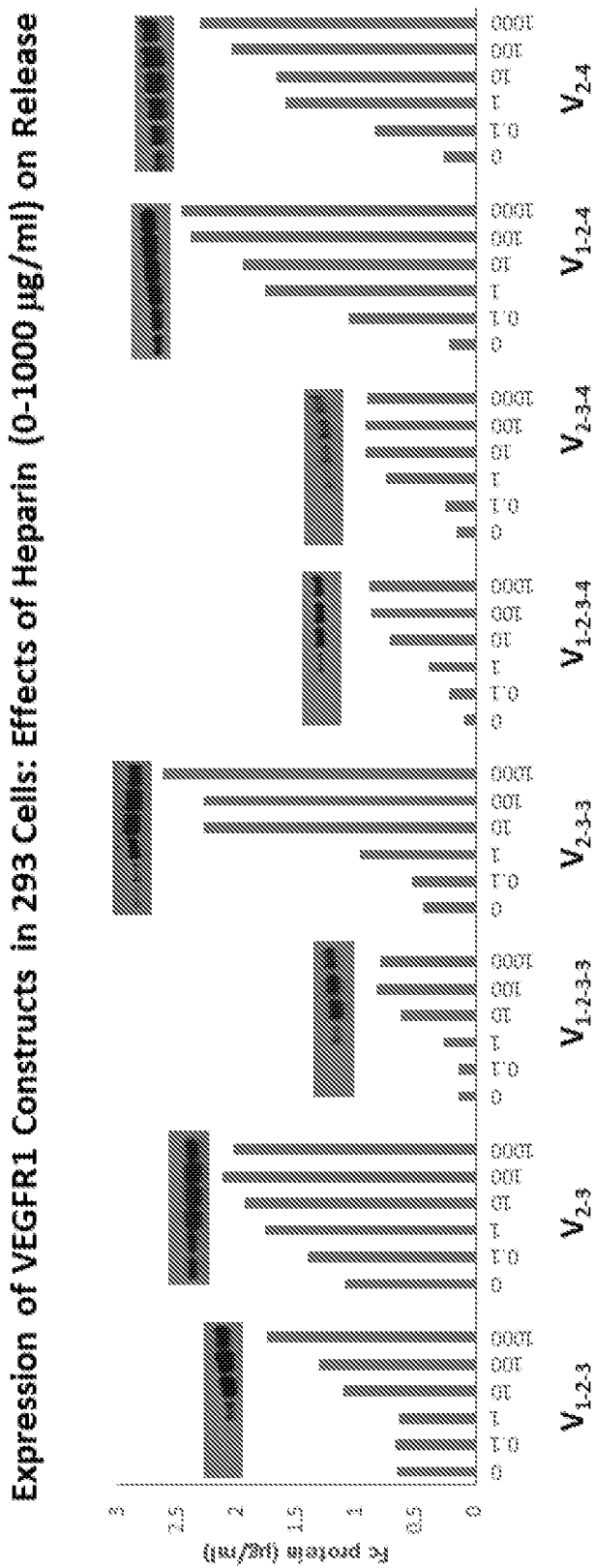
FIG. 10 depicts the expression of VEGFR-1 constructs in 293 cells.

The Examples show that the expression levels of most constructs were low; $V_{1-2-3-4}$, $V_{1-2-3-3}$, $V_{2-3-4}$ and $V_{1-2-4}$ were almost completely undetectable in the conditioned media. Previous studies had shown that VEGF isoforms with high affinity for heparin (VEGF$_{189}$ or VEGF$_{206}$) are undetectable in the conditioned media of transfected cells, being tightly bound to the cells surface or the extracellular matrix[31,32]. However, they could be released in a soluble form by the addition of heparin or heparinase, indicating that the binding site consisted of HSPG[31,32] This example sought to determine whether the addition of heparin may also affect the levels of recombinant VEGFR-1 fusion proteins. Indeed, adding heparin to the media of transfected cells in 6-well plates resulted in dose-dependent increases in the concentrations of recombinant protein in the media (FIG. 10).

Figure 11:
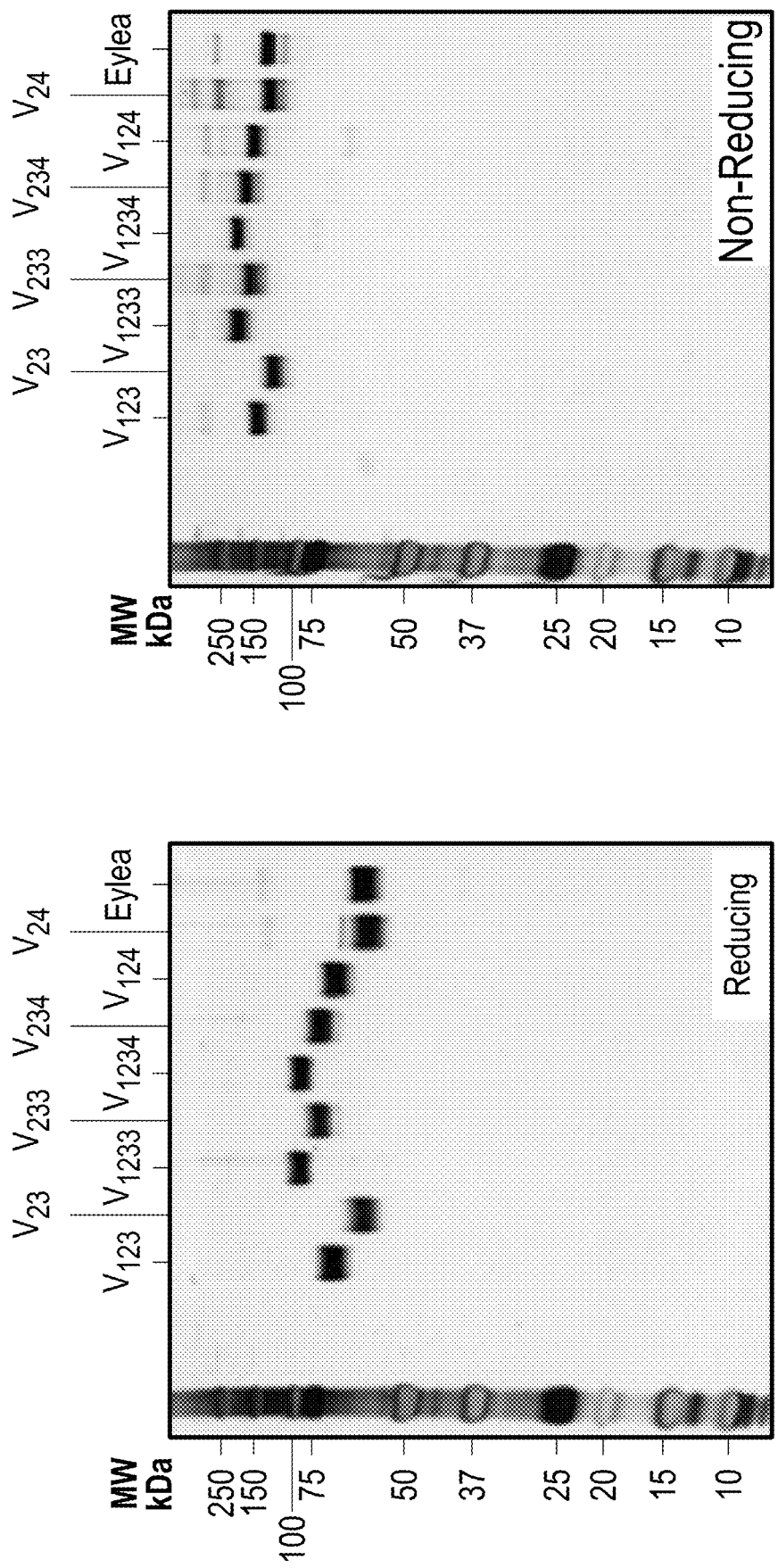
FIG. 11 depicts silver-stained PAGE gels under reducing and non-reducing conditions of 200 ng of each VEGFR-1 Fc fusion protein compared to EYLEA.
Figure 12A:
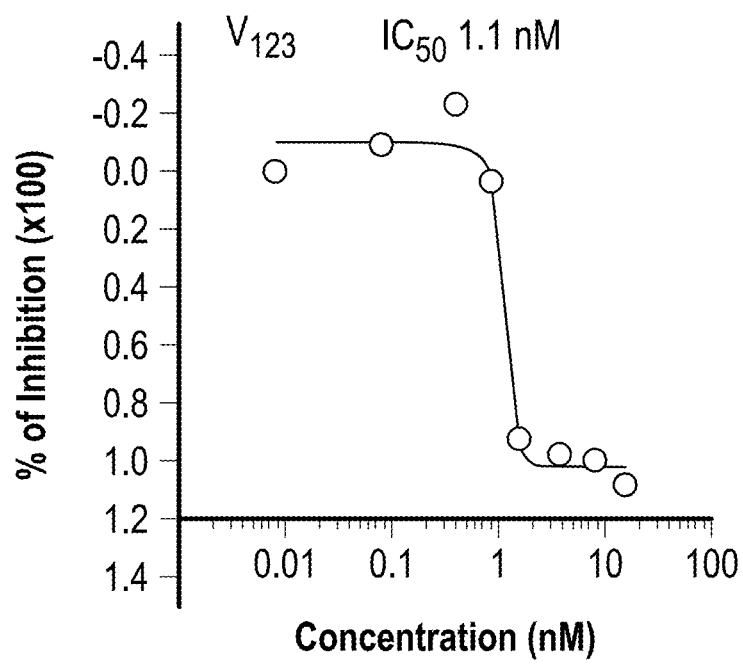
FIG. 12 depicts inhibitory effects of VEGF receptor chimeric proteins on VEGF-stimulated endothelial cell proliferation.
Figure 12B:
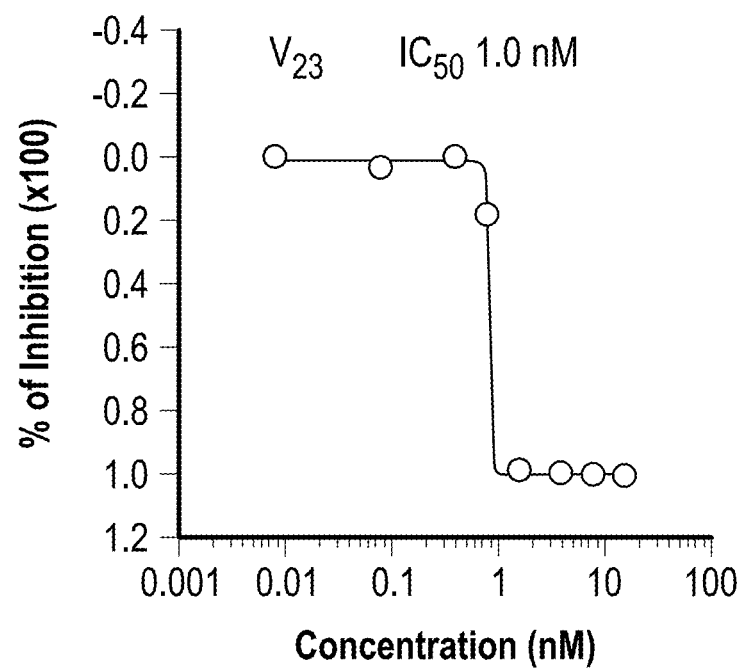
Figure 12C:
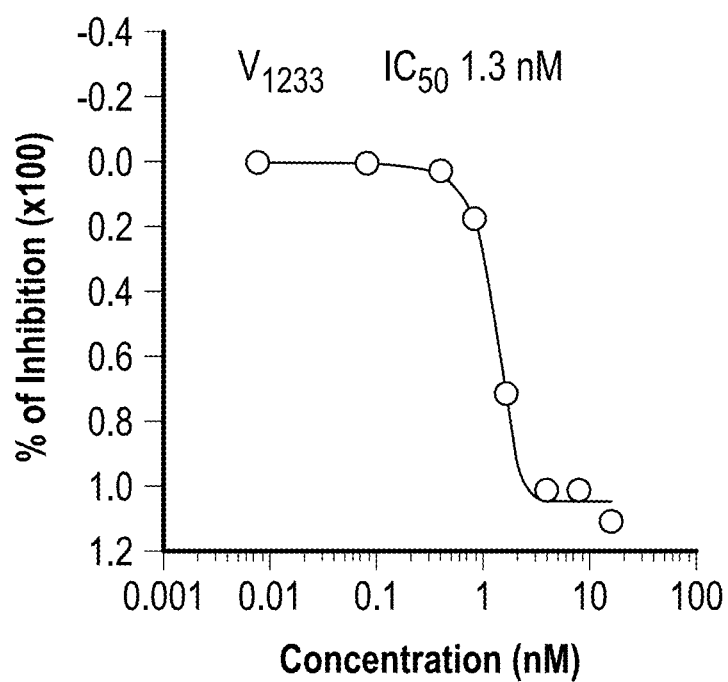
Figure 12D:
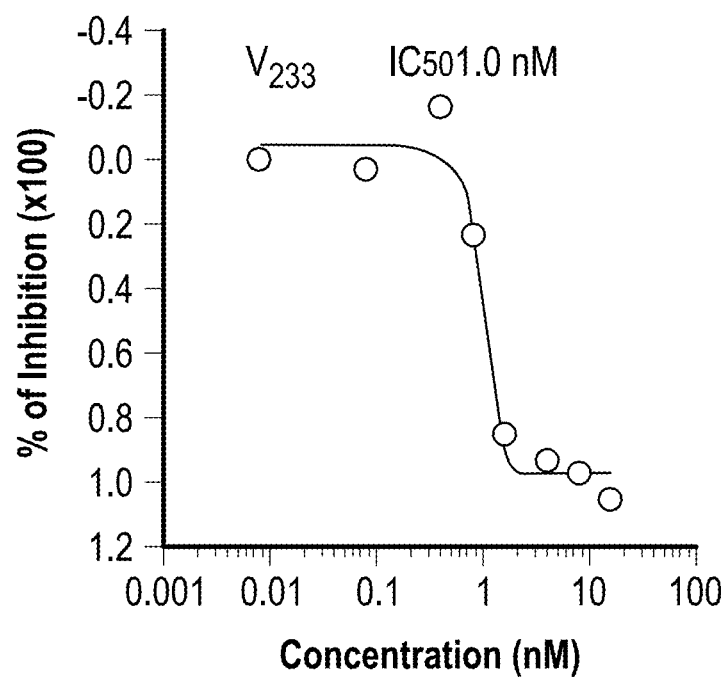
Figure 12E:
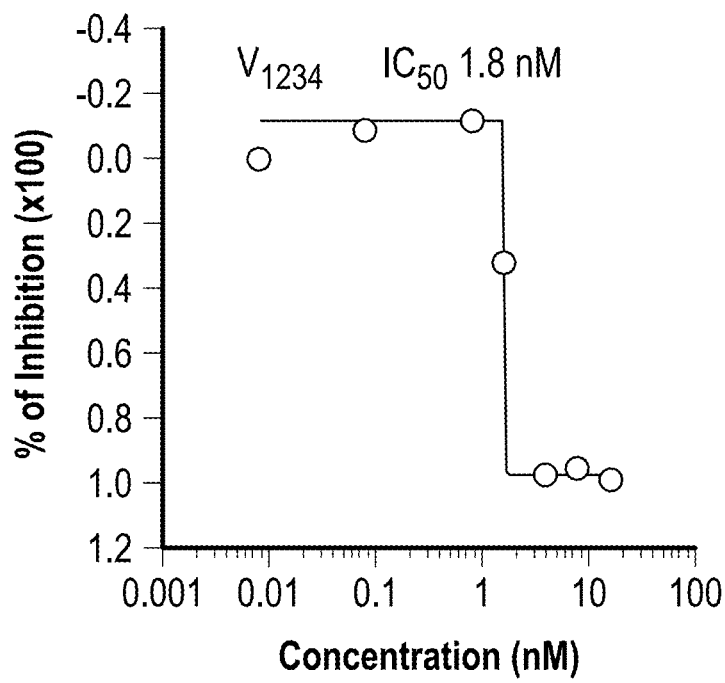
Figure 12F:
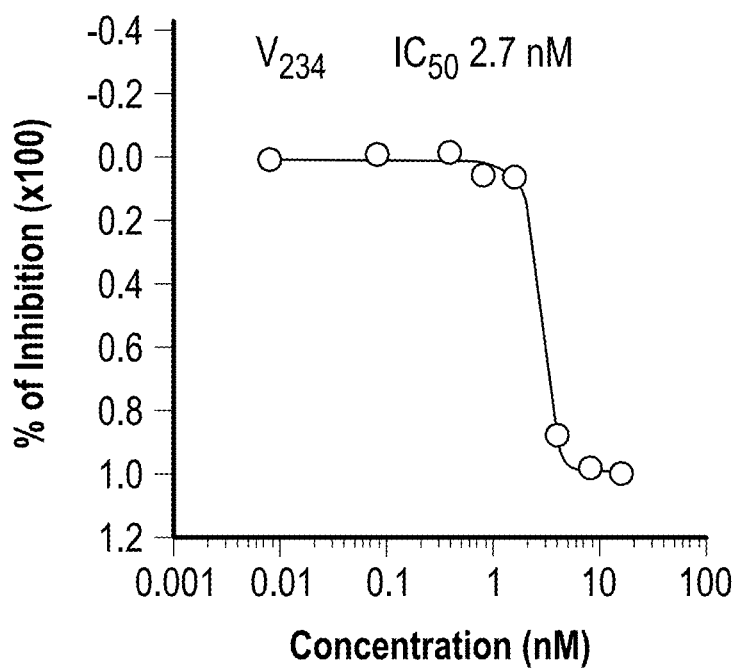
Figure 12G:
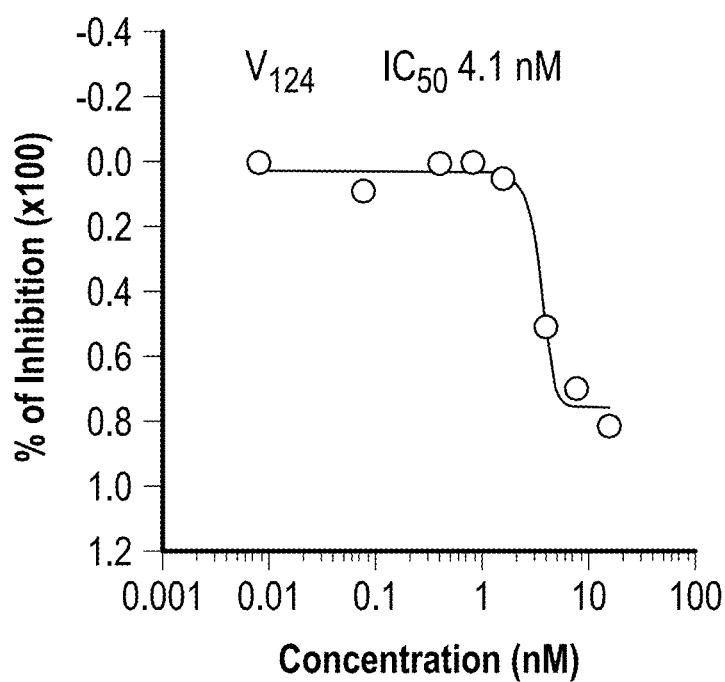
Figure 12H:
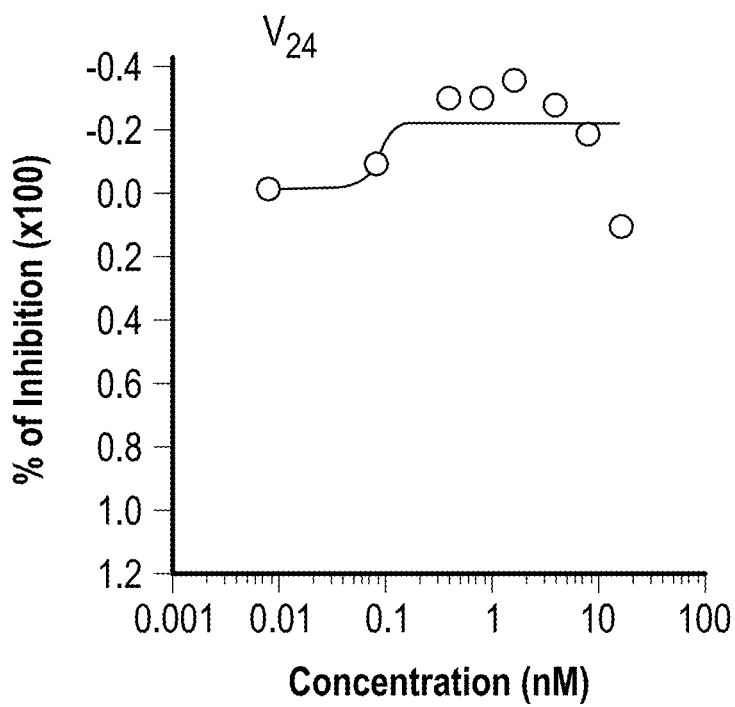
Figure 12I:
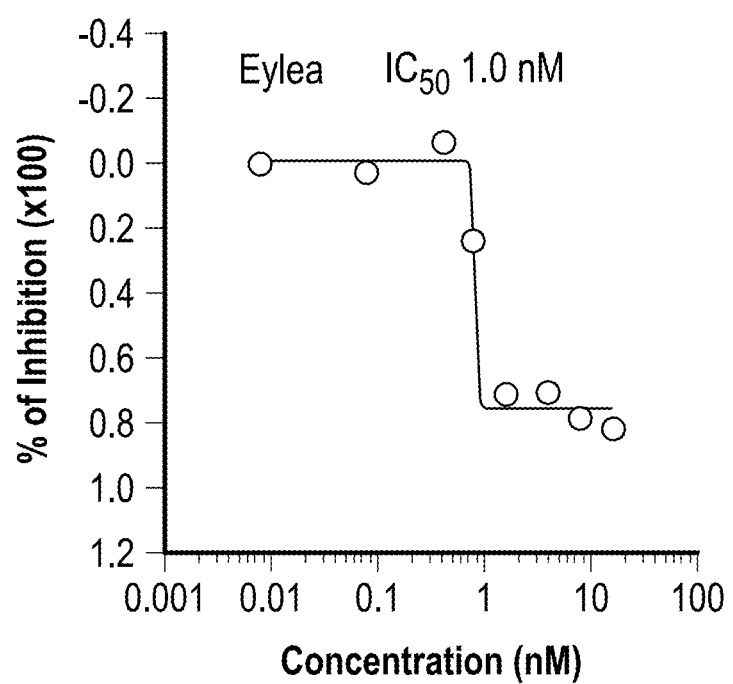
Figure 13A:
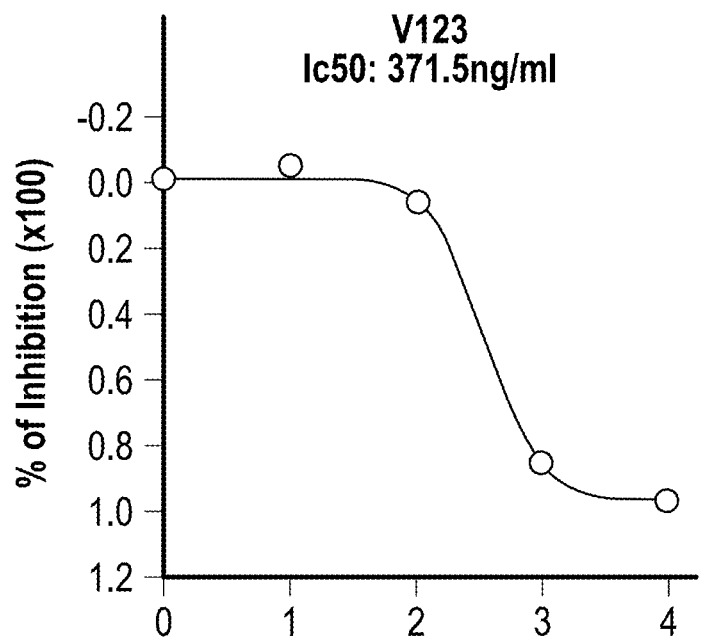
FIG. 13 depicts competition of VEGF for Biotinylated VEGF (at 100 ng/ml) binding to VEGFR1 soluble receptor.
Figure 13B:
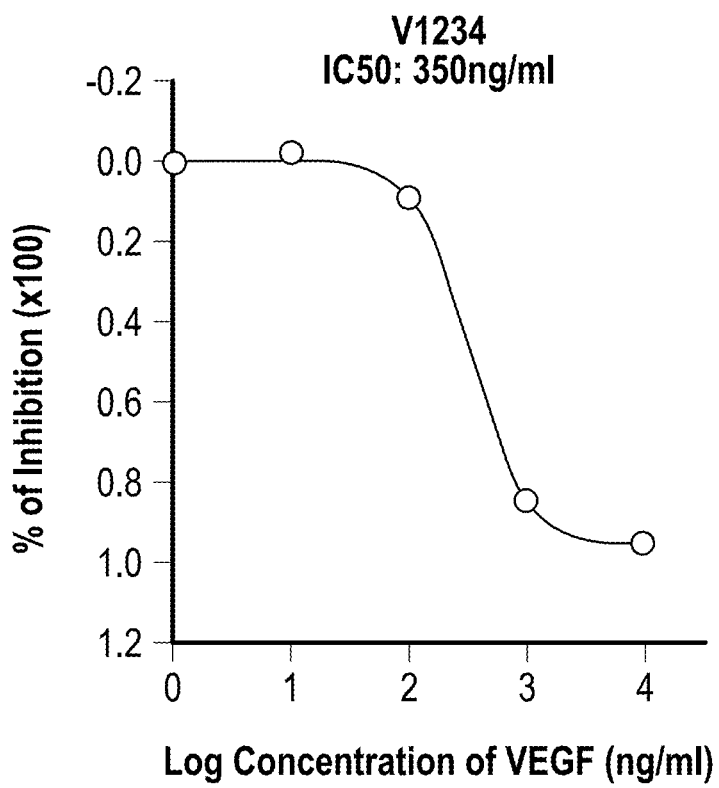
Figure 13C:
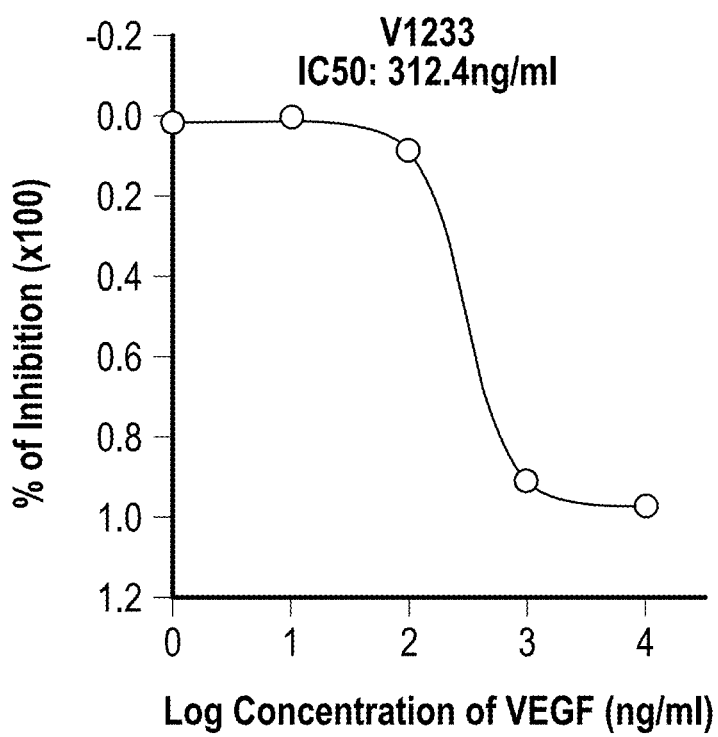
Figure 13D:
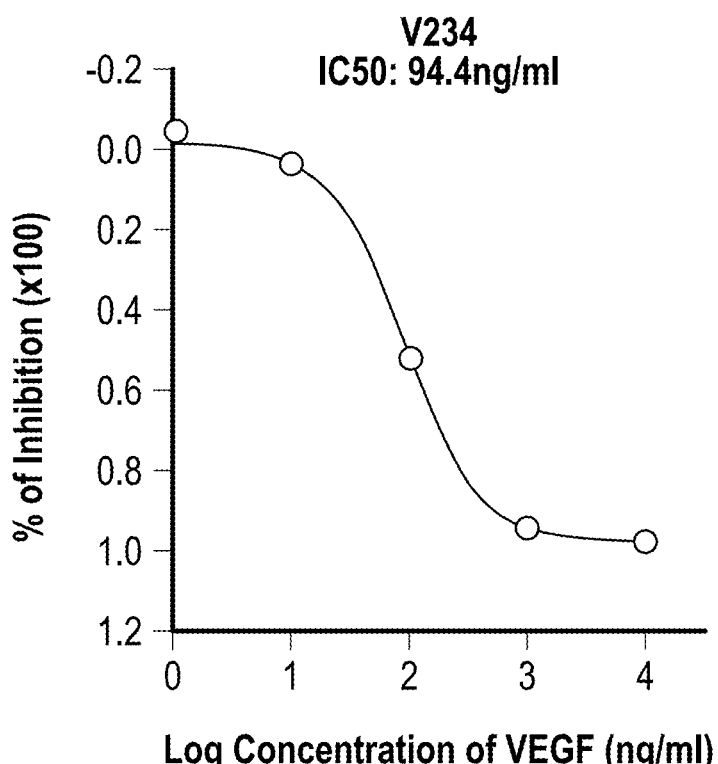
Figure 13E:
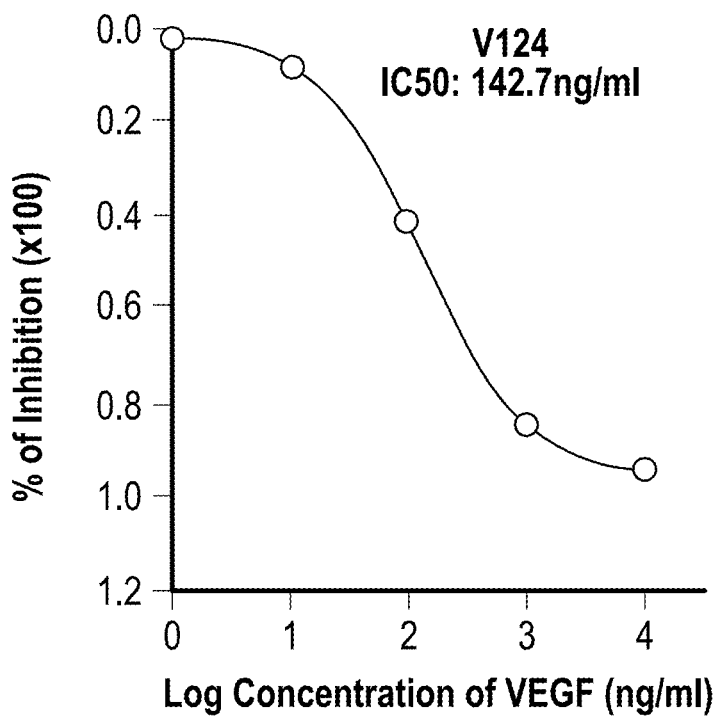
Figure 13F:
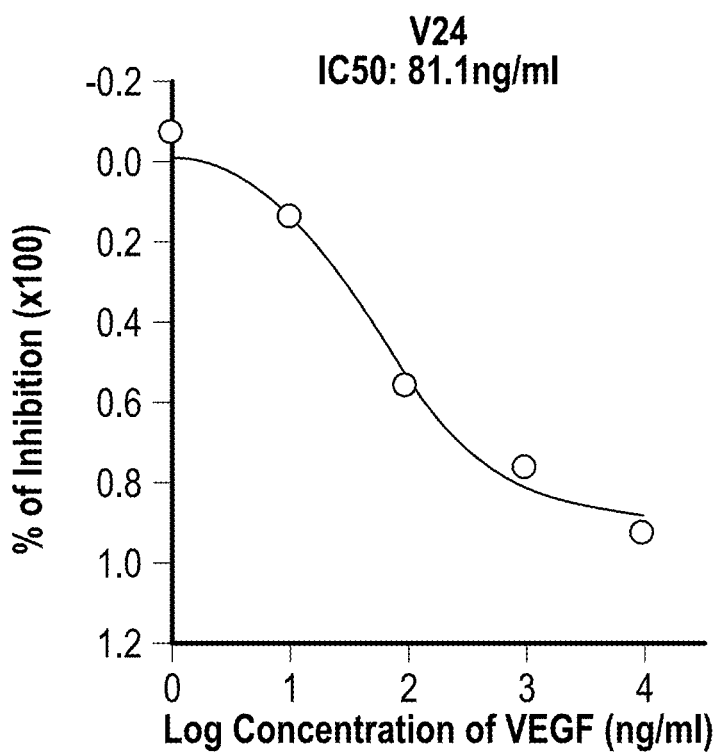
Figure 13G:
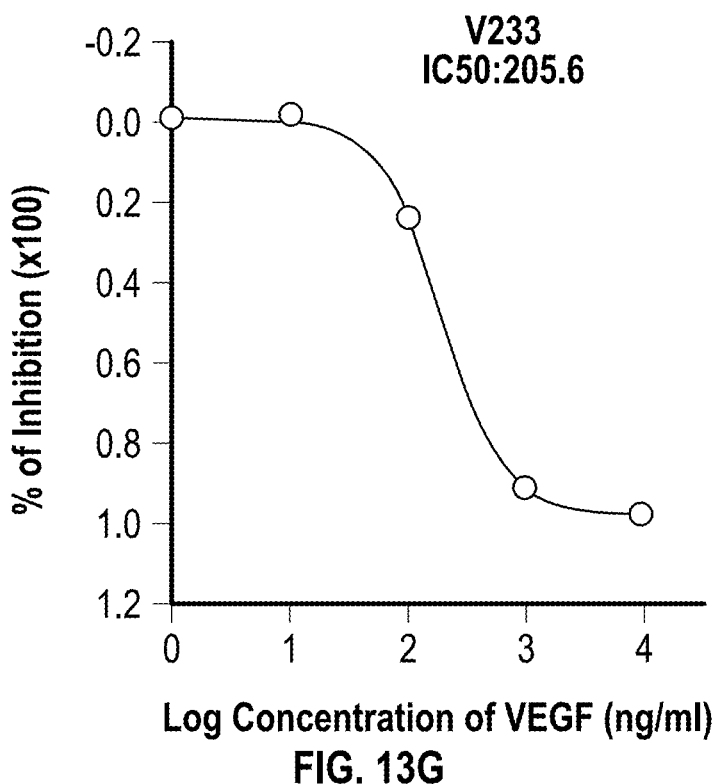
Figure 13H:
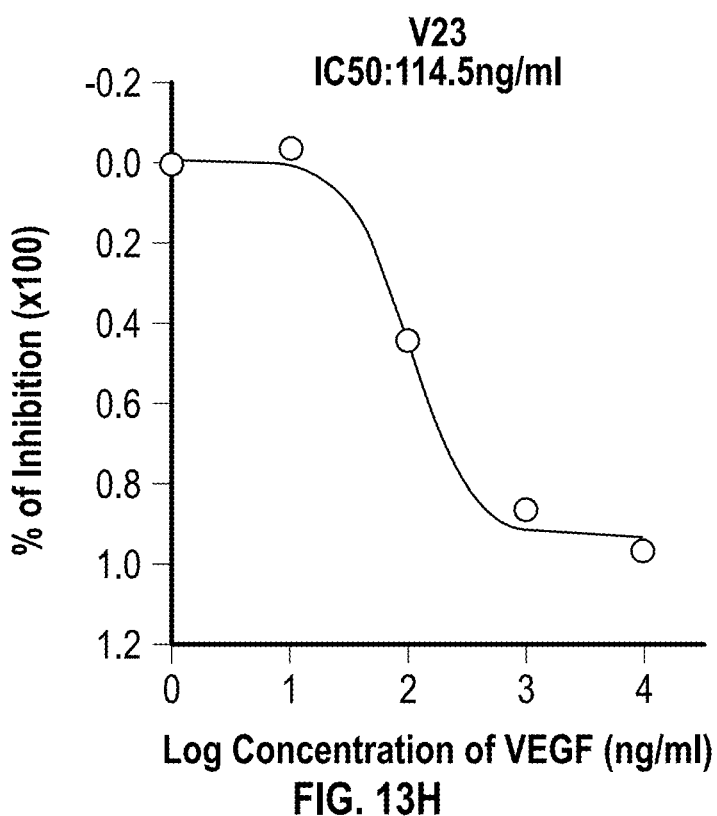
Figure 13I:
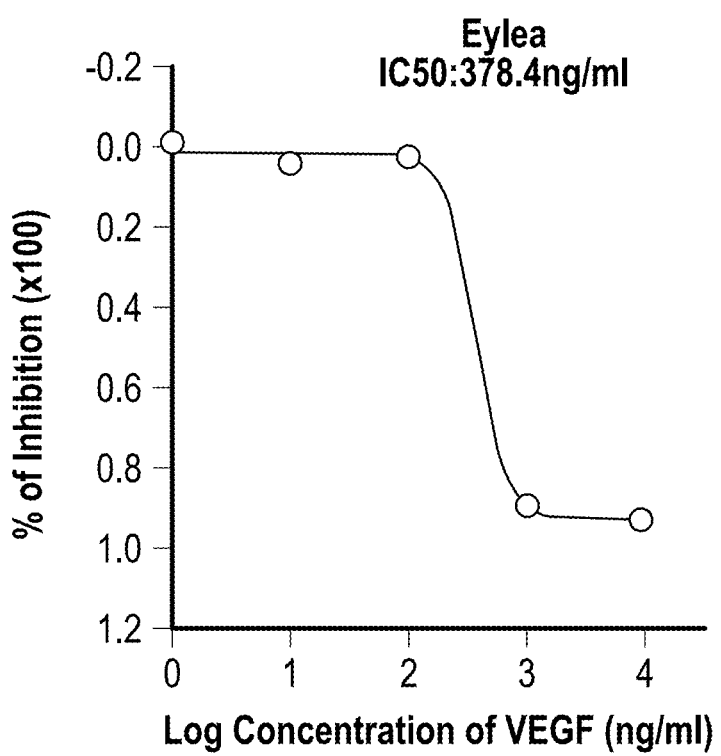

In seeking to purify the recombinant proteins, conventional protein A (PA) affinity chromatography alone yielded a major band of the expected mass, but with numerous minor bands, likely reflecting the interaction of the recombinant proteins with host cell-derived HSPGs and other molecules. A protocol was developed that removed such impurities, as described in Methods. A wash at high pH (for example 9.2) in the presence of 1.2 M NaCl while the protein is bound to PA, resulted in release of numerous contaminants. The next step, anion exchange chromatography with Hi-Trap Q, was very effective at removing the bulk of contaminants and aggregates, while the purified proteins were in the flow-through. The LPS levels in the final purified preparations were <0.1 EU/mg (range 0.02-0.08), a very low level compatible with preclinical studies[33]. As shown in FIG. 11, the purity of recombinant proteins was >95%, as assessed by silver-stained SDS/PAGE gel and was similar to that of the FDA-approved drug EYLEA.

The recombinant proteins were tested for their ability to inhibit mitogenesis stimulated by VEGF (10 ng/ml) in bovine choroidal endothelial cells. The recombinant proteins had inhibitory effects, with $IC_{50}$ values were in the range of ~1 nM, except for $V_{1-2-4}$ and $V_{2-4}$, which were less potent (FIG. 12). Interestingly, EYLEA, even at the highest concentration tested, inhibited no more than ~80% of VEGF-stimulated proliferation (FIG. 12). In contrast, the present VEGFR-1 constructs, (except, $V_{1-2-4}$ and $V_{2-4}$), completely blocked VEGF-induced proliferation (FIG. 12). Binding assays documented the interaction between the soluble VEGF receptors and the biotinylated VEGF and the ability of VEGF to displace binding (FIG. 13, 14).

Figure 14:
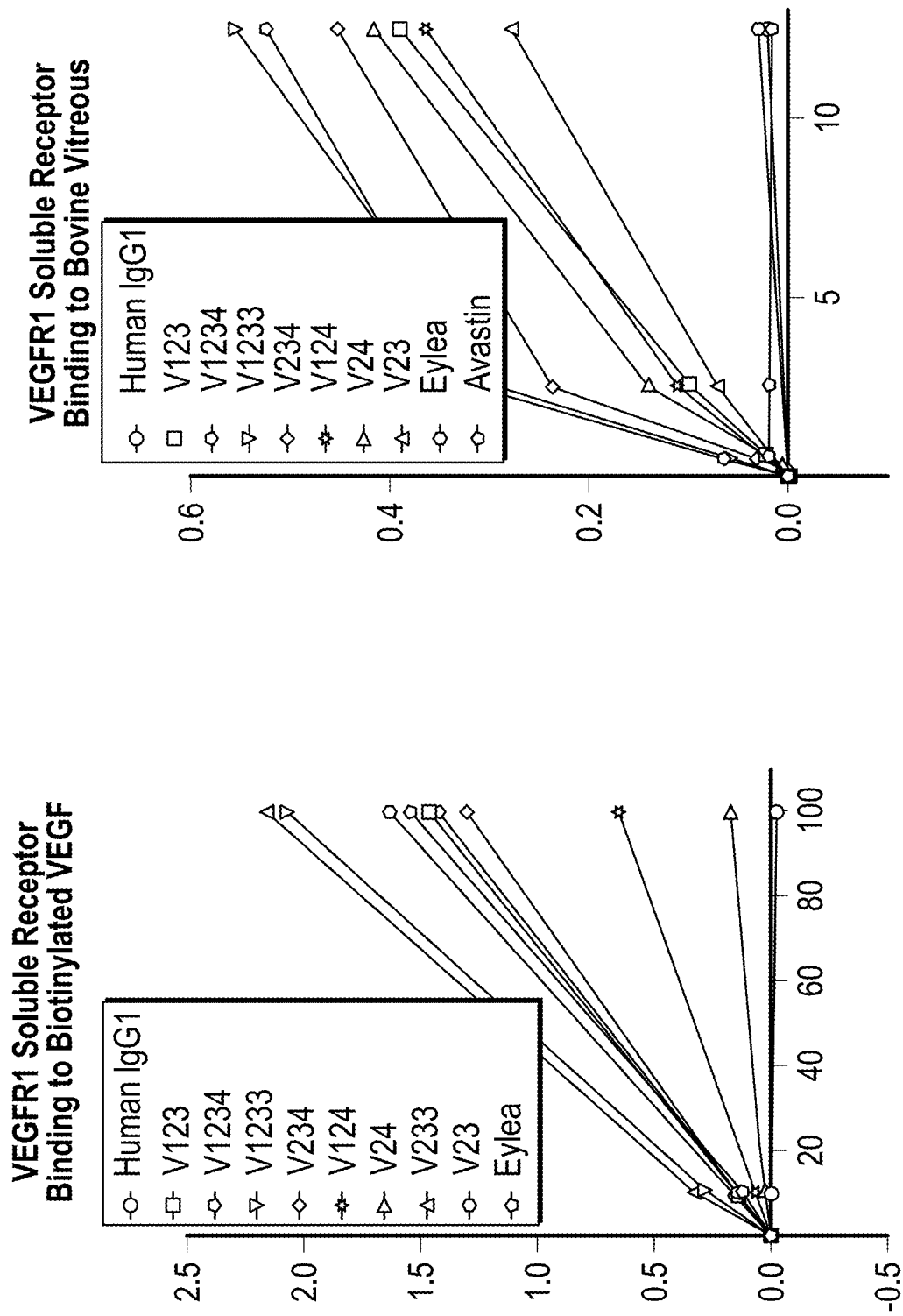
FIG. 14 depicts VEGFR-1 soluble receptor binding to Biotinylated VEGF and bovine vitreous.

To further define therapeutically relevant interactions, we sought to assess whether the recombinant proteins bind bovine vitreous in vitro. As illustrated in FIG. 14, while EYLEA or control IgG had little or no binding, the present proteins showed significant binding. The strongest binders were $V_{1-2-3-3}$, $V_{2-3-3}$ and $V_{1-2-3-4}$ followed by $V_{1-2-3}$. $V_{2-3}$ had intermediate binding characteristics, between EYLEA (or control IgG) and $V_{1-2-3-3}$. AVASTIN, a monoclonal antibody[9] commonly used to treat intraocular neovascularization, also had little or no binding.

Figure 15:
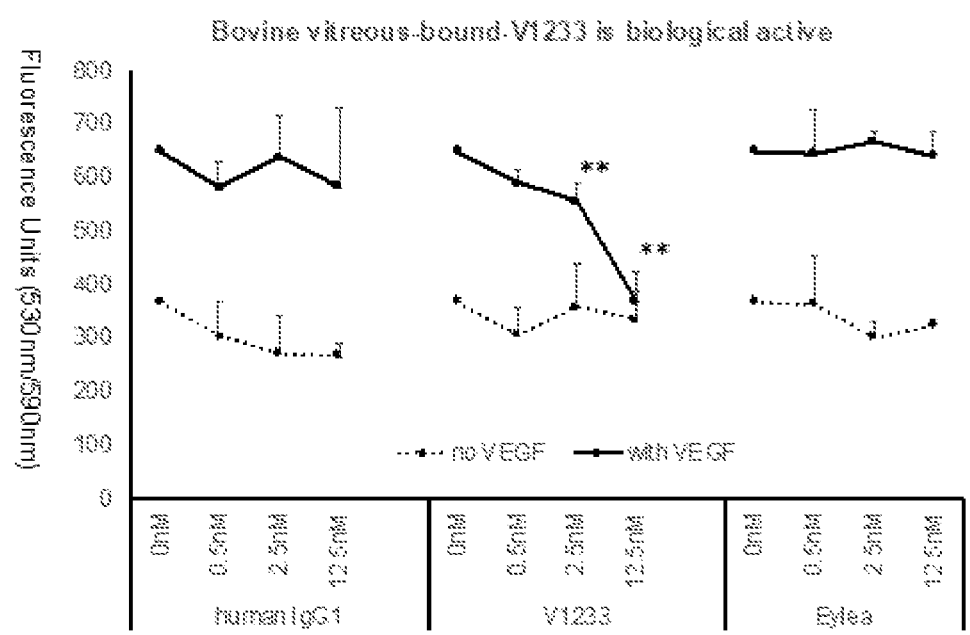
FIG. 15 depicts bovine vitreous-bound $V_{1-2-3-3}$ is biologically active.

To determine whether vitreous-bound VEGFR-1 FC fusion may be biologically active, plates were coated with bovine vitreous. Addition of $V_{1-2-3-3}$, but not EYLEA or control IgG, inhibited the ability of exogenously added VEGF to stimulate endothelial cell proliferation (FIG. 15).

Figure 16:
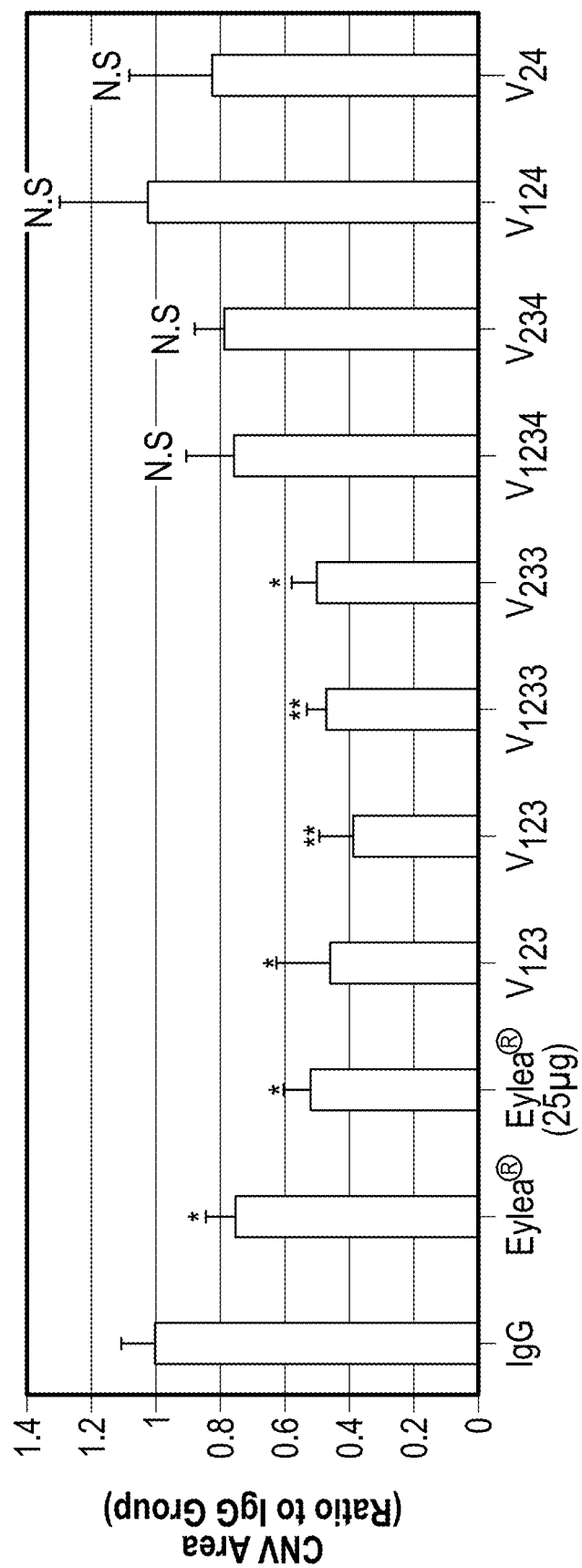
FIG. 16 shows effects of control IgG, EYLEA, or VEGFR-1 Fc fusion proteins on choroidal neovascularization (CNV) area. Each protein was injected intravitreally in the mouse at the dose of 2.5 mg one day before laser treatment. EYLEA was tested also at 25 mg. Asterisks denote significant differences (Student's t test) compared to the appropriate IgG control groups ($**p<0.01$, $*p<0.05$).

The recombinant proteins were tested in the mouse CNV assay and compared them to control IgG or EYLEA. Each protein was injected intravitreally at the dose of 2.5 µg one day before laser treatment. EYLEA was tested also at 25 µg. $V_{1-2-3}$, $V_{2-3}$, $V_{1-2-3-3}$ and $V_{2-3-3}$ at the dose of 2.5 µg demonstrated a degree of inhibition similar or greater to that achieved with 25 µg EYLEA. However, none of the constructs containing D4 demonstrated significant inhibition under the circumstances tested (FIG. 16).

Figure 17A:
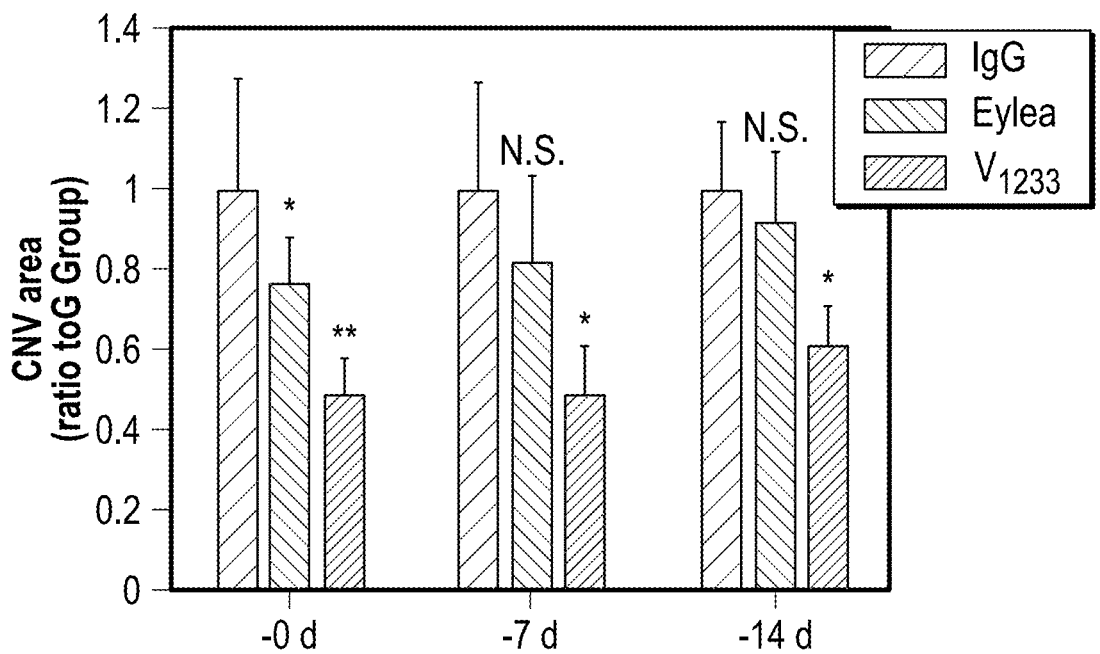
FIGS. 17A and 17B show effects of EYLEA, $V_{1,2,3,3}$ or control IgG on CNV area following a single intravitreal administration (2.5 mg), 1 day, 7 days or 14 days before laser treatment. Asterisk denote significant differences ($p<0.05$, Student's t test) compared to the IgG control group.
Figure 17B:
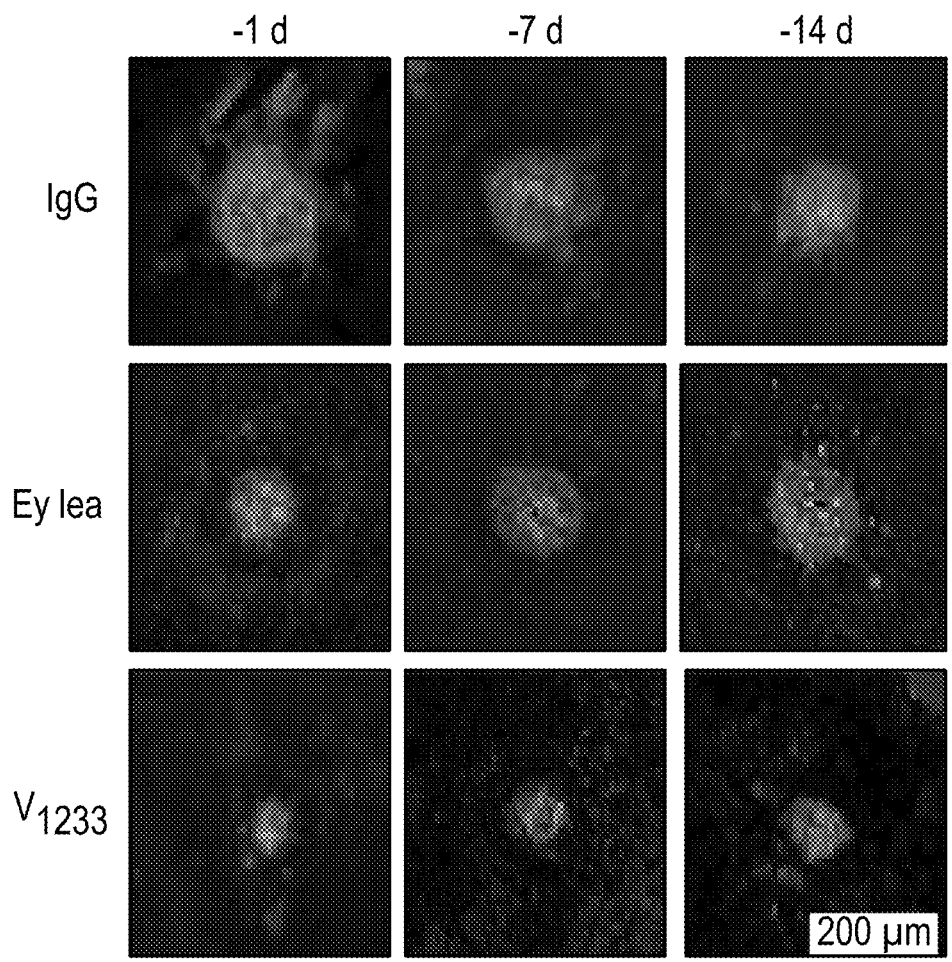

To determine whether heparin binding may translate in durable therapeutic effects following a single administration, $V_{1-2-3-3}$, EYLEA or control IgG, were injected intravitreally (2.5 µg) 1 day, 7 days or 14 days before the laser-induced injury. As shown in FIG. 17, EYLEA resulted in a significant inhibition only when administered 1 day before the injury. However, $V_{1-2-3-3}$ resulted in a significant inhibition also when administered 7 days or 14 days prior to the injury.

Disclosed are several novel VEGFR-1-Fc constructs evaluated in a variety of in vitro and in vivo assays. To purify the recombinant proteins, a multi-step protocol was used. This was dictated to a large degree by the relatively low expression levels in transiently expressing 293 cells, requiring the addition of heparin to the media to improve release. However, the need to use heparin may be in part or entirely obviated by different host cells (e.g., having a different composition of HSPG or mutants thereof) or by higher expression levels such as in amplified, stable cell lines.

All constructs, except $V_{2-4}$, potently neutralized the activity of VEGF and, at the same time, had strong heparin-binding characteristics, which may predict a long half-life following intravitreal administration. The example documents that these proteins bind to bovine vitreous. The strongest binders were $V_{1-2-3-3}$, $V_{2-3-3}$, $V_{1-2-3-4}$, followed by $V_{1-2-3}$. $V_{2-3}$ had significant but lower vitreous binding. Control IgG, EYLEA, or AVASTIN had instead minimal binding. One of the strongest vitreous binders, $V_{1-2-3-3}$, was selected to test the hypothesis that a vitreal matrix-bound VEGFR1 Fc constructs may be biologically active. As shown in FIG. 15, in plates coated with bovine vitreous, addition of $V_{1-2-3-3}$, but not EYLEA or control IgG, inhibited the ability of exogenously added VEGF to stimulate endothelial cell proliferation.

Next the recombinant proteins were tested in the mouse CNV model for their ability to inhibit laser-induced neovascularization. EYLEA was used as a positive control and human IgG1 as a negative control. Relatively low dose was chosen for in vivo testing, being best suited to reveal potency differences among the various constructs. Also, it has been reported that intravitreal administration of relatively high doses of antibodies of the IgG1 isotype may have off-target inhibitory effects, mediated by FcgRI (CD64) and c-Cbl, when injected intravitreally 34. The dose employed should avoid such off-target effects and detect truly specific effects.

As shown in FIG. 16, EYLEA resulted in an approximately 30% inhibition at the dose of 2.5 μg and ~50% inhibition at 25 μg. These findings are largely consistent with the published literature. Saishin et al reported that the intravitreal injection of ~5 μg aflibercept resulted in ~30% inhibition of CNV area in the mouse[35]. Indeed, the dose of 40 g is commonly used to achieve a maximal effect in the mouse CNV model[36]. An unexpected finding of our study was the greater potency of some of our constructs: $V_{1-2-3}$, $V_{2-3}$, $V_{1-2-3-3}$ and $V_{2-3-3}$. Administering 2.5 μg of these constructs one day before the injury matched or even exceeded the level of inhibition achieved with 25 μg of EYLEA. The finding that $V_{1-2-3-3}$, but not EYLEA, has significant effect on preventing CNV when administered 7 days or 14 days before the injury (FIG. 17), documents the durability of the effect and the therapeutic value.

An unexpected finding is that none of the constructs containing D4 ($V_{1-2-3-4}$, $V_{2-3-4}$, $V_{1-2-4}$, $V_{2-4}$) resulted in marked inhibition in vivo (at least at the dose tested), in spite of the fact that these molecules (with the exception of $V_{2-4}$) demonstrated an ability to block VEGF-stimulated mitogenesis in vitro. However, all of these constructs demonstrated a propensity to form multimers or aggregates, as assessed by SDS/PAGE gel under non-reducing conditions (FIG. 11) or size exclusion chromatography (not shown). Although earlier work[37] identified D4 (together with D7) as a requirement for VEGFR-1 dimerization, such effect has been known to be ligand-dependent. Crystal structure studies revealed a loop in D4 responsible for such homotypic interactions[23]. It is conceivable that high concentrations and/or the forced dimerization imposed by the Fc construct may result in ligand-independent interactions, resulting in aggregation. In any event, aggregates are not desirable pharmaceuticals given the possibility of inflammation and immunogenicity[38, 39] Therefore, an aspect of the present invention is the identification of constructs having VEGFR-1 D2/D3, but not D4, in embodiments.

It is noteworthy that well-characterized Fc mutations, well known to the skilled in the art, that reduce effector functions could be useful additions to the invention in order to minimize antibody-dependent cytoxicity (ADCC) well as interactions with C1q and the initiation of the complement cascade[40].

In conclusion, aflibercept was designed to eliminate the heparin-binding heparin domain in order to improve systemic half-life for oncological indications. The constructs described in the present study are instead designed to promote binding and retention in the vitreous to ensure more sustained and therapeutically relevant interactions.

Methods

For construction of VEGFR-$1_{ECD}$-Fc expression plasmids, the nucleic acid fragments encoded the signal peptide and a variety of extracellular Ig-like domains one to four[20] of VEGRF-1 (Gene ID: 2321) were synthesized by GenScript USA Inc. The variety of the extracellular Ig-like domain constructs is as follows: V123 contains D1, 2 and 3; V23, D1 and D2; V1234, D1, 2, 3 and 4; V1233, D1, 2, 3 and 3; V234, D 2, 3 and 4; V124, D1, 2 and 4; V24, D2 and 4; F7 is ECD2, 2 and 3 and F8 is ECD2 and 3. The synthesized fragments were inserted into pFUSE-hIgGl-Fc vector (InvivoGen, #pfuse-hgifc1) at EcoRI and BglII sites, generating the plasmids containing the various Flt1 ECDs. Then, using PrineSTAR Mutagenesis Basal Kit (Takara, R046A), the interval amino acid R and S (BglII site) between the ECDs and the Fc fragment were removed, generating the plasmids (F1-F8) expressing the fusion proteins of Flt1 ECDs with a 227-amino acid human IgG1-Fc.

Transfection and Conditioned Media Preparation

The Expi293 expression system (Life technologies, A14524) was used to generate the conditioned media for purification, according to the manufacturer's instructions. In brief, Expi293F™ Cells (ThermoFisher) were suspension-cultured in Expi293™ expression medium at 37° C. in a humidified atmosphere with 8% CO2. When the cell density reached to 2.5 million/ml, plasmids DNA and Expi-Fectamine™ 293 reagent was mixed, incubated 5 min and added to the cells. The final concentration of the DNA and transfected reagent was 1 μg and 2.7 μl per milliliter respectively. Five hours after transfection, 100 μg/ml Heparin (Sigma, H3149) and protease inhibitor cocktail, 1:400 (Sigma, P1860), were added to the cells. 16 hours after transfection, enhancer reagents 1 and 2 were added. Ninety-six hours after transfection, conditioned media were harvested. Aliquots were tested for Fc fusion proteins concentrations using a human Fc ELISA Kit (Syd Labs, EK000095-HUFC-2) according to the manufacturer's instructions. Protease inhibitors were added (1:500) to the bulk, which was stored at −80° C. until further use.

Purification of Recombinant Proteins

Pyrogen-free reagents were employed. Prior to use, columns and equipment (Akta Explorer System) were sanitized by exposure to 0.5 N NaOH for approximately 45 minutes. Conditioned media from transfected cells were adjusted to PBS, 0.01% polysorbate (PS) 20. PS20 was added to buffers at all steps. After centrifugation at 20,000×g for 30 minutes, supernatants were subjected to protein A (PA) affinity chromatography using a Hi-Trap MabSeledt SuRe (5 ml, GE Healthcare). After loading, the column was washed with 20 mM diethanolamine, pH 9.2, 1.2 M NaCl, prior to elution with 0.1 M citric acid, pH 3.0, which was immediately neutralized. The PA elution pool was then diluted in 20 mM diethanolamine, pH 9.2, and applied to Hi-Trap Q (5 ml, GE Healthcare) anion-exchange column. The bound material was eluted with a gradient of NaCl. The flow-through, which contained the purified recombinant protein, was immediately adjusted to 20 mM Tris, pH 6.8, and then concentrated through binding to heparin-sepharose (Hi-Trap™-HS). After a wash with 0.2-0.45 M NaCl (depending on the construct), the recombinant VEGFR1 fusion protein was eluted with 1 M NaCl. The final polishing step consisted of size-exclusion chromatography (SEC), using, for example, Superdex 200 Increase, 10/300 GL or Hi-Load 16/600 Superdex 200 µg, GE Healthcare. Finally, the proteins were buffer-exchanged by dialysis into 10 mM Tris, pH 6.8, 10 mM histidine, 1% threalose, 40 mM NaCl, 0.01% PS20. To determine endotoxin levels, ToxinSensor Chromogenic LAL Endotoxin Assay Kit (GenScript, L00350) was used according to the manufacturer's protocol.

Cell Proliferation Assays

Bovine endothelial cell proliferation assays were performed essentially as previously described[41]. Log phase growing bovine choroidal endothelial cells (BCEC) (passage <10) were trypsinized, re-suspended and seeded in 96-well plates (no coating) in low glucose DMEM supplemented with 10% bovine calf serum, 2 mM glutamine, and antibiotics, at a density of 1000 cells per well in 200 µl volume. rhVEGF$_{165}$ (Peprotech) was added at the concentration of 10 ng/ml. Aflibercept (EYLEA) was purchased from a pharmacy. The inhibitors were added to cell at various concentrations, as indicated in the figures, before adding the ligands. After 5 or 6 days, cells were incubated with Alamar Blue for 4 hr. Fluorescence was measured at 530 nm excitation wavelength and 590 nm emission wavelength.

Solid-Phase VEGFR-1 Variant Binding Assays

Costar 96-well EIA/RIA stripwells (#2592, Corning Incorporated, Kennebunk, Me.) were coated overnight at 4° C. with purified VEGF receptor proteins (250 ng/well) in coating buffer (Biolegend, San Diego, Calif., #421701). Nonspecific binding sites were blocked by incubating the strips with 2% BSA (Sigma, A6003) in PBS for 1 hour at room temperature (RT) after a single wash with ELISA wash buffer (R&D systems 895003). Strips were then washed 3 times, followed by adding biotinylated human VEGF$_{165}$ (G&P Biosciences, Santa Clara, Calif.) in assay diluent (Biolegend, #421203) alone or in combination with various concentrations of non-biotinylated human VEGF165 (R&D systems) at 37° C. for 2 hours. After three washes, bound biotinylated human VEGF$_{165}$ to VEGFR1 was detected by incubation with HRP Streptavidin (1:1000, Biolegend, #405210) for 1 hour at RT. Strips were washed 5 times before incubation with TMB high sensitivity substrate solution (Biolegend, #421501) for 30 min, and absorbance at 450 nm was measured after adding equal amount of stop solution (Biolegend, #77316). All experiments were carried out in duplicate wells and repeated for at least two times.

In Vitro Binding to Bovine Vitreous

Bovine vitreous (InVision BioResource, Seattle, Wash.) was thawed at 4° C. Material was first diluted 1:1 with PBS, filtered through 0.22 m filter, aliquoted and stored at −80° C. Total protein concentration of bovine vitreous material was measured by Pierce BCA protein assay. Costar 96-well EIA/RIA stripwells were coated with bovine vitreous (1 µg/well) for 4 hr at RT, followed by one wash with ELISA wash buffer. Nonspecific binding sites were blocked by adding 2% BSA in PBS for 1 hr at RT, followed by washing three times with 0.01% PBS-T. To each well, 50 ul VEGFR1 or control proteins were added overnight at 4° C. Next day, plates were washed three times with 0.01% PBS-T, followed by incubating with 100 ul AP-conjugated goat anti-human Fc (1:2000, Invitrogen, #A18832)) for 1 hr at RT. Plates were further washed five times with 0.01% PBS-T before adding 50 ul 1 step PNPP substrate (Thermo Scientific, Rockford, Ill., #37621) for 15-30 min at RT. OD was measured at 405 nm.

Effects of vitreous bound VEGFR1 on VEGF-stimulated endothelial cell proliferation in Costar 96-well EIA/RIA stripwells were first UV-sterilized for 1 hr, followed by coating with 1 g/well bovine vitreous, diluted in PBS for 4 hr at RT. Plates were washed with PBS once, blocked with 2% BSA at 4° C., and washed two times with PBS in biosafety hood. Equal amounts of soluble receptors or control IgG were added to plates, diluted in PBS O/N at 4° C. (50 µl/well). Plates were then washed once with PBS, followed by one wash with assay media containing 10% BCS. 100 µl media was added to each well, followed by addition of VEGF at 5 ng/ml or PBS only as no VEGF control. Plates were incubated with VEGF or PBS for 1 hr, followed by adding 100 µl BCEC cell suspension (final 2500 cells/well). 48 hrs later, proliferation was measured by adding Alamar Blue.

Laser-Induced Choroidal Neovascularization (CNV)

Male C57BL/6J mice (6-8 week) were anesthetized with ketamine/Xylazine cocktail before laser treatment. CNV lesions were induced by laser photocoagulation using a diode laser (IRIDEX, Oculight GL) and a slit lamp (Zeiss) with a spot size of 50 um, power of 180 mW and exposure duration of 100 ms.[36, 42] Four laser burns were typically induced at 3, 6, 9 and 12 o'clock position around the optic disc in each eye. Different constructs or IgG isotype control were injected intravitreally, at the dose of 2.5 µg per eye, in a 1 µl volume. EYLEA was used as a positive control at 2.5 or 25 µg. One day after injection, laser treatment was conducted and eyes were enucleated and fixed in 4% paraformaldehyde (PFA) for 15 min, 7 days after laser treatment. In a separate set of studies, selected constructs were injected once 1 day, 7 days or 14 days prior to laser treatment. Choroid-sclera complexes and retinas were separated and anti-CD31 immunofluorescence (IF) was performed to evidence the vasculature by whole mount staining of both retina and choroidal tissues. For CD31 IF, rat anti-mouse antibody BD 550274 was diluted 1:100 and incubated overnight at 4° C. After 4-hour incubation with a secondary anti-rat antibody (Life Technologies A11006), whole mounts were imaged at 488 nm. Quantification of neovascularization in lesion area and vascular density in retina was carried out by Image J. P values were assessed by Student's t test (significant change, p<0.05).

REFERENCES

[1] Folkman J, Klagsbrun M: Angiogenic factors. Science 1987, 235:442-7.
[2] Klagsbrun M, D'Amore P A: Regulators of angiogenesis. Annu Rev Physiol 1991, 53:217-39.
[3] Ferrara N, Gerber H P, LeCouter J: The biology of VEGF and its receptors. Nature Med 2003, 9:669-76.

[4] Ferrara N, Adamis A P: Ten years of anti-vascular endothelial growth factor therapy. Nat Rev Drug Discov 2016, 15:385-403.
[5] Olsson A K, Dimberg A, Kreuger J, Claesson-Welsh L: VEGF receptor signalling—in control of vascular function. Nat Rev Mol Cell Biol 2006, 7:359-71.
[6] Alitalo K, Tammela T, Petrova T V: Lymphangiogenesis in development and human disease. Nature 2005, 438:946-53.
[7] Ferrara N: VEGF and the quest for tumour angiogenesis factors. Nat Rev Cancer 2002, 2:795-803.
[8] Miller J W, Le Couter J, Strauss E C, Ferrara N: Vascular endothelial growth factor a in intraocular vascular disease. Ophthalmology 2013, 120:106-14.
[9] Presta L G, Chen H, O'Connor S J, Chisholm V, Meng Y G, Krummen L, Winkler M, Ferrara N: Humanization of an Anti-Vascular Endothelial Growth Factor Monoclonal Antibody for the Therapy of Solid Tumors and Other Disorders. Cancer Res 1997, 57:4593-9.
[10] Chen Y, Wiesmann C, Fuh G, Li B, Christinger H W, McKay P, de Vos A M, Lowman H B: Selection and analysis of an optimized anti-VEGF antibody: crystal structure of an affinity-matured Fab in complex with antigen. Journal of Molecular Biology 1999, 293:865-81.
[11] Chamow S M, Ashkenazi A: Immunoadhesins: principles and applications. Trends In Biotechnology 1996, 14:52-60.
[12] Chamow S M, Ryll T, Lowman H B, Farson D: Therapeutic Fc-Fusion Proteins. Wiley Blackwell, 2014.
[13] Holash J, Davis S, Papadopoulos N, Croll S D, Ho L, Russell M, Boland P, Leidich R, Hylton D, Burova E, Ioffe E, Huang T, Radziejewski C, Bailey K, Fandl J P, Daly T, Wiegand S J, Yancopoulos G D, Rudge J S: VEGF-Trap: a VEGF blocker with potent antitumor effects. Proc Natl Acad Sci USA 2002, 99:11393-8.
[14] Nguyen T T, Guymer R: Conbercept (KH-902) for the treatment of neovascular age-related macular degeneration. Expert Rev Clin Pharmacol 2015, 8:541-8.
[15] Comparison of Age-related Macular Degeneration Treatments Trials Research G, Maguire M G, Martin D F, Ying G S, Jaffe G J, Daniel E, Grunwald J E, Toth C A, Ferris F L, 3rd, Fine S L: Five-Year Outcomes with Anti-Vascular Endothelial Growth Factor Treatment of Neovascular Age-Related Macular Degeneration: The Comparison of Age-Related Macular Degeneration Treatments Trials. Ophthalmology 2016, 123:1751-61.
[16] Holz F G, Tadayoni R, Beatty S, Berger A, Cereda M G, Cortez R, Hoyng C B, Hykin P, Staurenghi G, Heldner S, Bogumil T, Heah T, Sivaprasad S: Multi-country real-life experience of anti-vascular endothelial growth factor therapy for wet age-related macular degeneration. Br J Ophthalmol 2015, 99:220-6.
[17] Regula J T, Lundh von Leithner P, Foxton R, Barathi V A, Cheung C M, Bo Tun S B, Wey Y S, Iwata D, Dostalek M, Moelleken J, Stubenrauch K G, Nogoceke E, Widmer G, Strassburger P, Koss M J, Klein C, Shima D T, Hartmann G: Targeting key angiogenic pathways with a bispecific CrossMAb optimized for neovascular eye diseases. EMBO Mol Med 2016, 8:1265-88.
[18] Rodrigues G A, Mason M, Christie L A, Hansen C, Hernandez L M, Burke J, Luhrs K A, Hohman T C: Functional Characterization of Abicipar-Pegol, an Anti-VEGF DARPin Therapeutic That Potently Inhibits Angiogenesis and Vascular Permeability. Invest Ophthalmol Vis Sci 2018, 59:5836-46.
[19] Vorum H, Olesen T K, Zinck J, Hedegaard M: Real world evidence of use of anti-VEGF therapy in Denmark. Curr Med Res Opin 2016:1-32.
[20] Davis-Smyth T, Chen H, Park J, Presta L G, Ferrara N: The second immunoglobulin-like domain of the VEGF tyrosine kinase receptor Flt-1 determines ligand binding and may initiate a signal transduction cascade. EMBO Journal 1996, 15:4919-27.
[21] Wiesmann C, Fuh G, Christinger H W, Eigenbrot C, Wells J A, de Vos A M: Crystal structure at 1.7 A resolution of VEGF in complex with domain 2 of the Flt-1 receptor. Cell 1997, 91:695-704.
[22] Christinger H W, Fuh G, de Vos A M, Wiesmann C: The Crystal Structure of Placental Growth Factor in Complex with Domain 2 of Vascular Endothelial Growth Factor Receptor-1. J Biol Chem 2004, 279:10382-8.
[23] Markovic-Mueller S, Stuttfeld E, Asthana M, Weinert T, Bliven S, Goldie K N, Kisko K, Capitani G, Ballmer-Hofer K: Structure of the Full-length VEGFR-1 Extracellular Domain in Complex with VEGF-A. Structure 2017, 25:341-52.
[24] Ferrara N, Chen H, Davis-Smyth T, Gerber H-P, Nguyen T-N, Peers D, Chisholm V, Hillan K J, Schwall R H: Vascular endothelial growth factor is essential for corpus luteum angiogenesis. Nature Medicine 1998, 4:336-40.
[25] Gerber H P, Vu T H, Ryan A M, Kowalski J, Werb Z, Ferrara N: VEGF couples hypertrophic cartilage remodeling, ossification and angiogenesis during endochondral bone formation. Nature Med 1999, 5:623-8.
[26] Gerber H P, Hillan K J, Ryan A M, Kowalski J, Keller G-A, Rangell L, Wright B D, Radtke F, Aguet M, Ferrara N: VEGF is required for growth and survival in neonatal mice. Development 1999, 126:1149-59.
[27] Gerber H P, Kowalski J, Sherman D, Eberhard D A, Ferrara N: Complete inhibition of rhabdomyosarcoma xenograft growth and neovascularization requires blockade of both tumor and host vascular endothelial growth factor. Cancer Res 2000, 60:6253-8.
[28] de Vries C, Escobedo J A, Ueno H, Houck K, Ferrara N, Williams L T: The fms-like tyrosine kinase, a receptor for vascular endothelial growth factor. Science 1992, 255:989-91.
[29] Sarrazin S, Lamanna W C, Esko J D: Heparan sulfate proteoglycans. Cold Spring Harb Perspect Biol 2011, 3.
[30] Woodard K T, Liang K J, Bennett W C, Samulski R J: Heparan Sulfate Binding Promotes Accumulation of Intravitreally Delivered Adeno-associated Viral Vectors at the Retina for Enhanced Transduction but Weakly Influences Tropism. J Virol 2016, 90:9878-88.
[31] Houck K A, Leung D W, Rowland A M, Winer J, Ferrara N: Dual regulation of vascular endothelial growth factor bioavailability by genetic and proteolytic mechanisms. J-Biol-Chem 1992, 267:26031-7.
[32] Ferrara N: Binding to the extracellular matrix and proteolytic processing: two key mechanisms regulating vascular endothelial growth factor action. Mol Biol Cell 2010 21:687-90.
[33] Malyala P, Singh M: Endotoxin limits in formulations for preclinical research. J Pharm Sci 2008, 97:2041-4.
[34] Bogdanovich S, Kim Y, Mizutani T, Yasuma R, Tudisco L, Cicatiello V, Bastos-Carvalho A, Kerur N, Hirano Y, Baffi J Z, Tarallo V, Li S, Yasuma T, Arpitha P, Fowler B J, Wright C B, Apicella I, Greco A, Brunetti A, Ruvo M, Sandomenico A, Nozaki M, Ijima R, Kaneko H, Ogura Y, Terasaki H, Ambati B K, Leusen J H, Langdon W Y, Clark M R, Armour K L, Bruhns P, Verbeek J S, Gelfand B D, De Falco S, Ambati J: Human IgG1 antibodies suppress angiogenesis in a target-independent manner. Signal Transduct Target Ther 2016, 1.

[35] Saishin Y, Takahashi K, Lima e Silva R, Hylton D, Rudge J S, Wiegand S J, Campochiaro P A: VEGF-TRAP (R1R2) suppresses choroidal neovascularization and VEGF-induced breakdown of the blood-retinal barrier. J Cell Physiol 2003, 195:241-8.

[36] Silva RLE, Kanan Y, Mirando A C, Kim J, Shmueli R B, Lorenc V E, Fortmann S D, Sciamanna J, Pandey N B, Green J J, Popel A S, Campochiaro P A: Tyrosine kinase blocking collagen I V-derived peptide suppresses ocular neovascularization and vascular leakage. Sci Transl Med 2017, 9.

[37] Barleon B, Totzke F, Herzog C, Blanke S, Kremmer E, Siemeister G, Marme D, Martiny-Baron G: Mapping of the sites for ligand binding and receptor dimerization at the extracellular domain of the vascular endothelial growth factor receptor FLT-1. Journal of Biological Chemistry 1997, 272:10382-8.

[38] Roberts C J: Therapeutic protein aggregation: mechanisms, design, and control. Trends Biotechnol 2014, 32:372-80.

[39] Ratanji K D, Derrick J P, Dearman R J, Kimber I: Immunogenicity of therapeutic proteins: influence of aggregation. J Immunotoxicol 2014, 11:99-109.

[40] Wang X, Mathieu M, Brezski R J: IgG Fc engineering to modulate antibody effector functions. Protein Cell 2018, 9:63-73.

[41] Yu L, Wu X, Cheng Z, Lee C V, Lecouter J, Campa C, Fuh G, Lowman H, Ferrara N: Interaction between Bevacizumab and Murine VEGF-A: A Reassessment. Invest Ophthalmol Vis Sci 2008, 49:522-7.

[42] Lambert V, Lecomte J, Hansen S, Blacher S, Gonzalez M L, Struman I, Sounni N E, Rozet E, de Tullio P, Foidart J M, Rakic J M, Noel A: Laser-induced choroidal neovascularization model to study age-related macular degeneration in mice. Nat Protoc 2013, 8:2197-211.

[43] Heier J. S., Kherani S., Desai S., Dugel P., Kaushal S., Cheng S. H., Delacono C., Purvis A., Richards S., Le-Halpere A., et al., Intravitreous injection of AAV2-sFLT01 in patients with advanced neovascular age-related macular degeneration: a phase 1, open-label trial, *Lancet* 390, 2017, 50-61.

[44] Heier Rakoczy E. P., Lai C. M., Magno A. L., Wikstrom M. E., French M. A., Pierce C. M., Schwartz S. D., Blumenkranz M. S., Chalberg T. W., Degli-Esposti M. A. and Constable I. J., Gene therapy with recombinant adeno-associated vectors for neovascular age-related macular degeneration: 1 year follow-up of a phase 1 randomised clinical trial, *Lancet* 386, 2015, 2395-2403.

What is claimed is:

1. An anti-VEGF agent comprising a VEGF binding portion operatively linked to a Fc-IgG, wherein the VEGF binding portion comprises a VEGF binding domain consisting essentially of an IgG-like domain 2 of VEGFR-1, a VEGF binding domain that is an IgG-like domain 3 of VEGFR-1, and a VEGF binding domain that is an IgG-like domain 4 of VEGFR-1.

2. The anti-VEGF agent of claim 1, wherein the anti-VEGF agent comprises the amino acid sequence of SEQ ID NO: 11.

3. A pharmaceutical composition comprising a therapeutically effective amount of the anti-VEGF agent of claim 1 and a pharmaceutically acceptable excipient.

* * * * *

SEQUENCE LISTING

```
<160> NUMBER OF SEQ ID NOS: 14

<210> SEQ ID NO 1
<211> LENGTH: 558
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
                20                  25                  30

Glu Leu Ser Leu Lys Gly Thr Gln His Ile Met Gln Ala Gly Gln Thr
            35                  40                  45

Leu His Leu Gln Cys Arg Gly Glu Ala Ala His Lys Trp Ser Leu Pro
        50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175
```

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
            195                 200                 205

Ala Thr Val Asn Gly His Leu Tyr Lys Thr Asn Tyr Leu Thr His Arg
210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
            245                 250                 255

Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
            275                 280                 285

Ala Asn Ile Phe Tyr Ser Val Leu Thr Ile Asp Lys Met Gln Asn Lys
            290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Asp Lys Thr His Thr
            325                 330                 335

Cys Pro Pro Cys Pro Ala Pro Glu Leu Leu Gly Gly Pro Ser Val Phe
            340                 345                 350

Leu Phe Pro Pro Lys Pro Lys Asp Thr Leu Met Ile Ser Arg Thr Pro
            355                 360                 365

Glu Val Thr Cys Val Val Val Asp Val Ser His Glu Asp Pro Glu Val
370                 375                 380

Lys Phe Asn Trp Tyr Val Asp Gly Val Glu Val His Asn Ala Lys Thr
385                 390                 395                 400

Lys Pro Arg Glu Glu Gln Tyr Asn Ser Thr Tyr Arg Val Val Ser Val
            405                 410                 415

Leu Thr Val Leu His Gln Asp Trp Leu Asn Gly Lys Glu Tyr Lys Cys
            420                 425                 430

Lys Val Ser Asn Lys Ala Leu Pro Ala Pro Ile Glu Lys Thr Ile Ser
            435                 440                 445

Lys Ala Lys Gly Gln Pro Arg Glu Pro Gln Val Tyr Thr Leu Pro Pro
450                 455                 460

Ser Arg Glu Glu Met Thr Lys Asn Gln Val Ser Leu Thr Cys Leu Val
465                 470                 475                 480

Lys Gly Phe Tyr Pro Ser Asp Ile Ala Val Glu Trp Glu Ser Asn Gly
            485                 490                 495

Gln Pro Glu Asn Asn Tyr Lys Thr Thr Pro Pro Val Leu Asp Ser Asp
            500                 505                 510

Gly Ser Phe Phe Leu Tyr Ser Lys Leu Thr Val Asp Lys Ser Arg Trp
            515                 520                 525

Gln Gln Gly Asn Val Phe Ser Cys Ser Val Met His Glu Ala Leu His
            530                 535                 540

Asn His Tyr Thr Gln Lys Ser Leu Ser Leu Ser Pro Gly Lys
545                 550                 555

<210> SEQ ID NO 2
<211> LENGTH: 1674
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

```
atggtcagct actgggacac cggggtcctg ctgtgcgcgc tgctcagctg tctgcttctc      60
acaggatcta gttcaggttc aaaattaaaa gatcctgaac tgagtttaaa aggcacccag     120
cacatcatgc aagcaggcca agacactgcat ctccaatgca gggggaagc agcccataaa     180
tggtctttgc ctgaaatggt gagtaaggaa agcgaaaggc tgagcataac taaatctgcc     240
tgtggaagaa atggcaaaca attctgcagt actttaacct tgaacacagc tcaagcaaac     300
cacactggct tctacagctg caaatatcta gctgtaccta cttcaaagaa gaaggaaaca     360
gaatctgcaa tctatatatt tattagtgat acaggtagac ctttcgtaga gatgtacagt     420
gaaatccccg aaattataca catgactgaa ggaagggagc tcgtcattcc ctgccgggtt     480
acgtcaccta acatcactgt tactttaaaa agtttccac ttgacacttt gatccctgat      540
ggaaaacgca taatctggga cagtagaaag ggcttcatca tatcaaatgc aacgtacaaa     600
gaaatagggc ttctgacctg tgaagcaaca gtcaatgggc atttgtataa gacaaactat     660
ctcacacatc gacaaaccaa tacaatcata gatgtccaaa taagcacacc acgcccagtc     720
aaattactta gaggccatac tcttgtcctc aattgtactg ctaccactcc cttgaacacg     780
agagttcaaa tgacctggag ttaccctgat gaaaaaaata gagagcttc cgtaaggcga     840
cgaattgacc aaagcaattc ccatgccaac atattctaca gtgttcttac tattgacaaa     900
atgcagaaca agacaaagg actttatact tgtcgtgtaa ggagtggacc atcattcaaa     960
tctgttaaca cctcagtgca tatatatgat aaagacaaaa ctcacacatg cccaccgtgc    1020
ccagcacctg aactcctggg gggaccgtca gtcttcctct ccccccaaa acccaaggac     1080
accctcatga tctcccggac ccctgaggtc acatgcgtgg tggtggacgt gagccacgaa    1140
gaccctgagg tcaagttcaa ctggtacgtg gacggcgtgg aggtgcataa tgccaagaca    1200
aagccgcggg aggagcagta caacagcacg taccgtgtgg tcagcgtcct caccgtcctg    1260
caccaggact ggctgaatgg caaggagtac aagtgcaagg tctccaacaa agccctccca    1320
gcccccatcg agaaaaccat ctccaaagcc aaagggcagc ccgagaacc acaggtgtac    1380
accctgcccc catcccggga ggagatgacc aagaaccagg tcagcctgac ctgcctggtc    1440
aaaggcttct atcccagcga catcgccgtg gagtgggaga gcaatgggca gccggagaac    1500
aactacaaga ccacgcctcc cgtgctggac tccgacggct ccttcttcct ctacagcaag    1560
ctcaccgtgg acaagagcag gtggcagcag gggaacgtct tctcatgctc cgtgatgcac    1620
gaggctctgc acaaccacta cacgcagaag agcctctccc tgtctccggg taaa          1674
```

<210> SEQ ID NO 3
<211> LENGTH: 459
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Met Val Ser Tyr Trp Asp Thr Gly Val Leu Leu Cys Ala Leu Leu Ser
 1               5                  10                  15

Cys Leu Leu Leu Thr Gly Ser Ser Ser Gly Ile Phe Ile Ser Asp Thr
            20                  25                  30

Gly Arg Pro Phe Val Glu Met Tyr Ser Glu Ile Pro Glu Ile Ile His
        35                  40                  45
```

-continued

Met Thr Glu Gly Arg Glu Leu Val Ile Pro Cys Arg Val Thr Ser Pro
         50                  55                  60

Asn Ile Thr Val Thr Leu Lys Lys Phe Pro Leu Asp Thr Leu Ile Pro
65                   70                  75                   80

Asp Gly Lys Arg Ile Ile Trp Asp Ser Arg Lys Gly Phe Ile Ile Ser
                 85                  90                  95

Asn Ala Thr Tyr Lys Glu Ile Gly Leu Leu Thr Cys Glu Ala Thr Val
             100                 105                 110

Asn Gly His Leu Tyr Lys Thr Asn Tyr Leu Thr His Arg Gln Thr Asn
         115                 120                 125

Thr Ile Ile Asp Val Gln Ile Ser Thr Pro Arg Pro Val Lys Leu Leu
     130                 135                 140

Arg Gly His Thr Leu Val Leu Asn Cys Thr Ala Thr Thr Pro Leu Asn
145                 150                 155                 160

Thr Arg Val Gln Met Thr Trp Ser Tyr Pro Asp Glu Lys Asn Lys Arg
                 165                 170                 175

Ala Ser Val Arg Arg Arg Ile Asp Gln Ser Asn Ser His Ala Asn Ile
             180                 185                 190

Phe Tyr Ser Val Leu Thr Ile Asp Lys Met Gln Asn Lys Asp Lys Gly
         195                 200                 205

Leu Tyr Thr Cys Arg Val Arg Ser Gly Pro Ser Phe Lys Ser Val Asn
     210                 215                 220

Thr Ser Val His Ile Tyr Asp Lys Asp Lys Thr His Thr Cys Pro Pro
225                 230                 235                 240

Cys Pro Ala Pro Glu Leu Leu Gly Gly Pro Ser Val Phe Leu Phe Pro
                 245                 250                 255

Pro Lys Pro Lys Asp Thr Leu Met Ile Ser Arg Thr Pro Glu Val Thr
             260                 265                 270

Cys Val Val Val Asp Val Ser His Glu Asp Pro Glu Val Lys Phe Asn
         275                 280                 285

Trp Tyr Val Asp Gly Val Glu Val His Asn Ala Lys Thr Lys Pro Arg
     290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                 325                 330                 335

Asn Lys Ala Leu Pro Ala Pro Ile Glu Lys Thr Ile Ser Lys Ala Lys
             340                 345                 350

Gly Gln Pro Arg Glu Pro Gln Val Tyr Thr Leu Pro Pro Ser Arg Glu
         355                 360                 365

Glu Met Thr Lys Asn Gln Val Ser Leu Thr Cys Leu Val Lys Gly Phe
     370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                 405                 410                 415

Phe Leu Tyr Ser Lys Leu Thr Val Asp Lys Ser Arg Trp Gln Gln Gly
             420                 425                 430

Asn Val Phe Ser Cys Ser Val Met His Glu Ala Leu His Asn His Tyr
         435                 440                 445

Thr Gln Lys Ser Leu Ser Leu Ser Pro Gly Lys
     450                 455

<210> SEQ ID NO 4
<211> LENGTH: 1377
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
atggtcagct actgggacac cggggtcctg ctgtgcgcgc tgctcagctg tctgcttctc    60
acaggatcta gttcaggtat atttattagt gatacaggta gaccttcgt agagatgtac    120
agtgaaatcc ccgaaattat acacatgact aaggaaggg agctcgtcat tccctgccgg    180
gttacgtcac ctaacatcac tgttacttta aaaaagtttc acttgacac tttgatccct    240
gatggaaaac gcataatctg gacagtaga aagggcttca tcatatcaaa tgcaacgtac    300
aaagaaatag gcttctgac ctgtgaagca acagtcaatg gcatttgta agacaaac      360
tatctcacac atcgacaaac caatacaatc atagatgtcc aaataagcac accacgccca   420
gtcaaattac ttagaggcca tactcttgtc ctcaattgta ctgctaccac tcccttgaac   480
acgagagttc aaatgacctg gagttaccct gatgaaaaaa ataagagagc ttccgtaagg   540
cgacgaattg accaaagcaa ttcccatgcc aacatattct acagtgttct tactattgac   600
aaaatgcaga acaaagacaa aggactttat acttgtcgtg taaggagtgg accatcattc   660
aaatctgtta acacctcagt gcatatatat gataaagaca aaactcacac atgcccaccg   720
tgcccagcac ctgaactcct gggggaccg tcagtcttcc tcttcccccc aaaacccaag   780
gacaccctca tgatctcccg gacccctgag gtcacatgcg tggtggtgga cgtgagccac   840
gaagaccctg aggtcaagtt caactggtac gtggacggcg tggaggtgca taatgccaag   900
acaaagccgc gggaggagca gtacaacagc acgtaccgtg tggtcagcgt cctcaccgtc   960
ctgcaccagg actggctgaa tggcaaggag tacaagtgca aggtctccaa caaagccctc  1020
ccagccccca tcgagaaaac catctccaaa gccaagggc agccccgaga accacaggtg  1080
tacaccctgc ccccatcccg ggaggagatg accaagaacc aggtcagcct gacctgcctg  1140
gtcaaaggct tctatcccag cgacatcgcc gtggagtggg agagcaatgg gcagccggag  1200
aacaactaca agaccacgcc tcccgtgctg gactccgacg gctccttctt cctctacagc  1260
aagctcaccg tggacaagag caggtggcag caggggaacg tcttctcatg ctccgtgatg  1320
cacgaggctc tgcacaacca ctacacgcag aagagcctct ccctgtctcc gggtaaa      1377
```

<210> SEQ ID NO 5
<211> LENGTH: 659
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

```
Met Val Ser Tyr Trp Asp Thr Gly Val Leu Leu Cys Ala Leu Leu Ser
1               5                  10                  15

Cys Leu Leu Leu Thr Gly Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60
```

```
Glu Met Val Ser Lys Glu Ser Glu Arg Leu Ser Ile Thr Lys Ser Ala
 65                  70                  75                  80

Cys Gly Arg Asn Gly Lys Gln Phe Cys Ser Thr Leu Thr Leu Asn Thr
             85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
            115                 120                 125

Ser Asp Thr Gly Arg Pro Phe Val Glu Met Tyr Ser Glu Ile Pro Glu
130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
            195                 200                 205

Ala Thr Val Asn Gly His Leu Tyr Lys Thr Asn Tyr Leu Thr His Arg
210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
            275                 280                 285

Ala Asn Ile Phe Tyr Ser Val Leu Thr Ile Asp Lys Met Gln Asn Lys
            290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Val Gln Ile Ser
                325                 330                 335

Thr Pro Arg Pro Val Lys Leu Leu Arg Gly His Thr Leu Val Leu Asn
            340                 345                 350

Cys Thr Ala Thr Thr Pro Leu Asn Thr Arg Val Gln Met Thr Trp Ser
            355                 360                 365

Tyr Pro Asp Glu Lys Asn Lys Arg Ala Ser Val Arg Arg Ile Asp
            370                 375                 380

Gln Ser Asn Ser His Ala Asn Ile Phe Tyr Ser Val Leu Thr Ile Asp
385                 390                 395                 400

Lys Met Gln Asn Lys Asp Lys Gly Leu Tyr Thr Cys Arg Val Arg Ser
            405                 410                 415

Gly Pro Ser Phe Lys Ser Val Asn Thr Ser Val His Ile Tyr Asp Lys
            420                 425                 430

Asp Lys Thr His Thr Cys Pro Pro Cys Pro Ala Pro Glu Leu Leu Gly
            435                 440                 445

Gly Pro Ser Val Phe Leu Phe Pro Pro Lys Pro Lys Asp Thr Leu Met
            450                 455                 460

Ile Ser Arg Thr Pro Glu Val Thr Cys Val Val Val Asp Val Ser His
465                 470                 475                 480
```

```
Glu Asp Pro Glu Val Lys Phe Asn Trp Tyr Val Asp Gly Val Glu Val
                485                 490                 495

His Asn Ala Lys Thr Lys Pro Arg Glu Glu Gln Tyr Asn Ser Thr Tyr
            500                 505                 510

Arg Val Val Ser Val Leu Thr Val Leu His Gln Asp Trp Leu Asn Gly
        515                 520                 525

Lys Glu Tyr Lys Cys Lys Val Ser Asn Lys Ala Leu Pro Ala Pro Ile
    530                 535                 540

Glu Lys Thr Ile Ser Lys Ala Lys Gly Gln Pro Arg Glu Pro Gln Val
545                 550                 555                 560

Tyr Thr Leu Pro Pro Ser Arg Glu Glu Met Thr Lys Asn Gln Val Ser
                565                 570                 575

Leu Thr Cys Leu Val Lys Gly Phe Tyr Pro Ser Asp Ile Ala Val Glu
            580                 585                 590

Trp Glu Ser Asn Gly Gln Pro Glu Asn Asn Tyr Lys Thr Thr Pro Pro
        595                 600                 605

Val Leu Asp Ser Asp Gly Ser Phe Phe Leu Tyr Ser Lys Leu Thr Val
    610                 615                 620

Asp Lys Ser Arg Trp Gln Gln Gly Asn Val Phe Ser Cys Ser Val Met
625                 630                 635                 640

His Glu Ala Leu His Asn His Tyr Thr Gln Lys Ser Leu Ser Leu Ser
                645                 650                 655

Pro Gly Lys

<210> SEQ ID NO 6
<211> LENGTH: 1977
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
atggtcagct actgggacac cggggtcctg ctgtgcgcgc tgctcagctg tctgcttctc      60
acaggatcta gttcaggttc aaaattaaaa gatcctgaac tgagtttaaa aggcacccag     120
cacatcatgc aagcaggcca gacactgcat ctccaatgca ggggggaagc agcccataaa     180
tggtctttgc ctgaaatggt gagtaaggaa agcgaaaggc tgagcataac taaatctgcc     240
tgtggaagaa atggcaaaca attctgcagt actttaacct tgaacacagc tcaagcaaac     300
cacactggct tctacagctg caaatatcta gctgtaccta cttcaaagaa gaaggaaaca     360
gaatctgcaa tctatatatt tattagtgat acaggtagac ctttcgtaga gatgtacagt     420
gaaatccccg aaattataca catgactgaa ggaagggagc tcgtcattcc tgccgggtt      480 acgtcaccta acatcactgt tactttaaaa agtttccac ttgacacttt gatccctgat      540
ggaaaacgca taatctggga cagtagaaag ggcttcatca tatcaaatgc aacgtacaaa     600
gaaatagggc ttctgacctg tgaagcaaca gtcaatgggc atttgtataa gacaaactat     660
ctcacacatc gacaaaccaa tacaatcata gatgtccaaa taagcacacc acgcccagtc     720
aaattactta gaggccatac tcttgtcctc aattgtactg ctaccactcc cttgaacacg     780
agagttcaaa tgacctggag ttaccctgat gaaaaaaata gagagcttc cgtaaggcga     840 cgaattgacc aaagcaattc ccatgccaac atattctaca gtgttcttac tattgacaaa     900
atgcagaaca agacaaagg actttatact tgtcgtgtaa ggagtggacc atcattcaa     960 tctgttaaca cctcagtgca tatatatgat aaagcagtcc aaataagcac accacgccca    1020
```

```
gtcaaattac ttagaggcca tactcttgtc ctcaattgta ctgctaccac tcccttgaac    1080
acgagagttc aaatgacctg gagttaccct gatgaaaaaa ataagagagc ttccgtaagg    1140
cgacgaattg accaaagcaa ttcccatgcc aacatattct acagtgttct tactattgac    1200
aaaatgcaga acaaagacaa aggactttat acttgtcgtg taaggagtgg accatcattc    1260
aaatctgtta acacctcagt gcatatatat gataaagaca aaactcacac atgcccaccg    1320
tgcccagcac ctgaactcct gggggggaccg tcagtcttcc tcttccccc aaaacccaag     1380 gacaccctca tgatctcccg gacccctgag gtcacatgcg tggtggtgga cgtgagccac    1440
gaagaccctg aggtcaagtt caactggtac gtggacggcg tggaggtgca taatgccaag    1500
acaaagccgc gggaggagca gtacaacagc acgtaccgtg tggtcagcgt cctcaccgtc    1560
ctgcaccagg actggctgaa tggcaaggag tacaagtgca aggtctccaa caaagccctc    1620
ccagccccca tcgagaaaac catctccaaa gccaagggc agccccgaga ccacaggtg     1680 tacaccctgc ccccatcccg ggaggagatg accaagaacc aggtcagcct gacctgcctg    1740
gtcaaaggct tctatcccag cgacatcgcc gtggagtggg agagcaatgg gcagccggag    1800
aacaactaca agaccacgcc tcccgtgctg gactccgacg gctccttctt cctctacagc    1860
aagctcaccg tggacaagag caggtggcag caggggaacg tcttctcatg ctccgtgatg    1920
cacgaggctc tgcacaacca ctacacgcag aagagcctct ccctgtctcc gggtaaa     1977
```

<210> SEQ ID NO 7
<211> LENGTH: 560
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ile Phe Ile Ser Asp Thr
            20                  25                  30

Gly Arg Pro Phe Val Glu Met Tyr Ser Glu Ile Pro Glu Ile Ile His
        35                  40                  45

Met Thr Glu Gly Arg Glu Leu Val Ile Pro Cys Arg Val Thr Ser Pro
    50                  55                  60

Asn Ile Thr Val Thr Leu Lys Lys Phe Pro Leu Asp Thr Leu Ile Pro
65                  70                  75                  80

Asp Gly Lys Arg Ile Ile Trp Asp Ser Arg Lys Gly Phe Ile Ile Ser
                85                  90                  95

Asn Ala Thr Tyr Lys Glu Ile Gly Leu Leu Thr Cys Glu Ala Thr Val
            100                 105                 110

Asn Gly His Leu Tyr Lys Thr Asn Tyr Leu Thr His Arg Gln Thr Asn
        115                 120                 125

Thr Ile Ile Asp Val Gln Ile Ser Thr Pro Arg Pro Val Lys Leu Leu
    130                 135                 140

Arg Gly His Thr Leu Val Leu Asn Cys Thr Ala Thr Thr Pro Leu Asn
145                 150                 155                 160

Thr Arg Val Gln Met Thr Trp Ser Tyr Pro Asp Glu Lys Asn Lys Arg
                165                 170                 175

Ala Ser Val Arg Arg Arg Ile Asp Gln Ser Asn Ser His Ala Asn Ile
            180                 185                 190
```

```
Phe Tyr Ser Val Leu Thr Ile Asp Lys Met Gln Asn Lys Asp Lys Gly
            195                 200                 205

Leu Tyr Thr Cys Arg Val Arg Ser Gly Pro Ser Phe Lys Ser Val Asn
    210                 215                 220

Thr Ser Val His Ile Tyr Asp Lys Ala Val Gln Ile Ser Thr Pro Arg
225                 230                 235                 240

Pro Val Lys Leu Leu Arg Gly His Thr Leu Val Leu Asn Cys Thr Ala
                245                 250                 255

Thr Thr Pro Leu Asn Thr Arg Val Gln Met Thr Trp Ser Tyr Pro Asp
            260                 265                 270

Glu Lys Asn Lys Arg Ala Ser Val Arg Arg Ile Asp Gln Ser Asn
    275                 280                 285

Ser His Ala Asn Ile Phe Tyr Ser Val Leu Thr Ile Asp Lys Met Gln
    290                 295                 300

Asn Lys Asp Lys Gly Leu Tyr Thr Cys Arg Val Arg Ser Gly Pro Ser
305                 310                 315                 320

Phe Lys Ser Val Asn Thr Ser Val His Ile Tyr Asp Lys Asp Lys Thr
                325                 330                 335

His Thr Cys Pro Pro Cys Pro Ala Pro Glu Leu Leu Gly Gly Pro Ser
            340                 345                 350

Val Phe Leu Phe Pro Pro Lys Pro Lys Asp Thr Leu Met Ile Ser Arg
    355                 360                 365

Thr Pro Glu Val Thr Cys Val Val Val Asp Val Ser His Glu Asp Pro
    370                 375                 380

Glu Val Lys Phe Asn Trp Tyr Val Asp Gly Val Glu Val His Asn Ala
385                 390                 395                 400

Lys Thr Lys Pro Arg Glu Glu Gln Tyr Asn Ser Thr Tyr Arg Val Val
                405                 410                 415

Ser Val Leu Thr Val Leu His Gln Asp Trp Leu Asn Gly Lys Glu Tyr
            420                 425                 430

Lys Cys Lys Val Ser Asn Lys Ala Leu Pro Ala Pro Ile Glu Lys Thr
    435                 440                 445

Ile Ser Lys Ala Lys Gly Gln Pro Arg Glu Pro Gln Val Tyr Thr Leu
    450                 455                 460

Pro Pro Ser Arg Glu Glu Met Thr Lys Asn Gln Val Ser Leu Thr Cys
465                 470                 475                 480

Leu Val Lys Gly Phe Tyr Pro Ser Asp Ile Ala Val Glu Trp Glu Ser
                485                 490                 495

Asn Gly Gln Pro Glu Asn Asn Tyr Lys Thr Thr Pro Pro Val Leu Asp
            500                 505                 510

Ser Asp Gly Ser Phe Phe Leu Tyr Ser Lys Leu Thr Val Asp Lys Ser
    515                 520                 525

Arg Trp Gln Gln Gly Asn Val Phe Ser Cys Ser Val Met His Glu Ala
    530                 535                 540

Leu His Asn His Tyr Thr Gln Lys Ser Leu Ser Leu Ser Pro Gly Lys
545                 550                 555                 560

<210> SEQ ID NO 8
<211> LENGTH: 1680
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 8

```
atggtcagct actgggacac cggggtcctg ctgtgcgcgc tgctcagctg tctgcttctc      60
acaggatcta gttcaggtat atttattagt gatacaggta gaccttcgt agagatgtac     120
agtgaaatcc ccgaaattat acacatgact gaaggaaggg agctcgtcat tccctgccgg    180
gttacgtcac ctaacatcac tgttacttta aaaagtttc cacttgacac tttgatccct    240
gatggaaaac gcataatctg ggacagtaga aagggcttca tcatatcaaa tgcaacgtac    300
aaagaaatag gcttctgac ctgtgaagca acagtcaatg gcatttgta aagacaaac     360
tatctcacac atcgacaaac caatacaatc atagatgtcc aaataagcac accacgccca    420
gtcaaattac ttagaggcca tactcttgtc ctcaattgta ctgctaccac tcccttgaac    480
acgagagttc aaatgacctg gagttaccct gatgaaaaaa ataagagagc ttccgtaagg    540
cgacgaattg accaaagcaa ttcccatgcc aacatattct acagtgttct tactattgac    600
aaaatgcaga acaagacaa aggactttat acttgtcgtg taaggagtgg accatcattc    660
aaatctgtta acacctcagt gcatatatat gataaagcag tccaaataag cacaccacgc    720
ccagtcaaat tacttagagg ccatactctt gtcctcaatt gtactgctac cactcccttg    780
aacacgagag ttcaaatgac ctggagttac cctgatgaaa aaataagag agcttccgta    840
aggcgacgaa ttgaccaaag caattcccat gccaacatat tctacagtgt tcttactatt    900
gacaaaatgc agaacaaaga caaggactt tatacttgtc gtgtaaggag tggaccatca    960
ttcaaatctg ttaacacctc agtgcatata tatgataaag acaaaactca cacatgccca   1020
ccgtgcccag cacctgaact cctgggggga ccgtcagtct tcctcttccc cccaaaaccc   1080
aaggacaccc tcatgatctc ccggacccct gaggtcacat gcgtggtggt ggacgtgagc   1140
cacgaagacc ctgaggtcaa gttcaactgg tacgtgacg gcgtggaggt gcataatgcc    1200
aagacaaagc cgcgggagga gcagtacaac agcacgtacc gtgtggtcag cgtcctcacc   1260
gtcctgcacc aggactggct gaatggcaag gagtacaagt gcaaggtctc caacaaagcc    1320
ctcccagccc ccatcgagaa aaccatctcc aaagccaaag gcagccccg agaaccacag    1380
gtgtacaccc tgcccccatc ccgggaggag atgaccaaga accaggtcag cctgacctgc   1440
ctggtcaaag gcttctatcc cagcgacatc gccgtggagt gggagagcaa tgggcagccg    1500
gagaacaact acaagaccac gcctcccgtg ctggactccg acggctcctt cttcctctac    1560
agcaagctca ccgtggacaa gagcaggtgg cagcagggga acgtcttctc atgctccgtg   1620
atgcacgagg ctctgcacaa ccactacacg cagaagagcc tctccctgtc tccgggtaaa   1680
```

<210> SEQ ID NO 9
<211> LENGTH: 655
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 9

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
```

```
                50                  55                  60
Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
            115                 120                 125

Ser Asp Thr Gly Arg Pro Phe Val Glu Met Tyr Ser Glu Ile Pro Glu
        130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
            195                 200                 205

Ala Thr Val Asn Gly His Leu Tyr Lys Thr Asn Tyr Leu Thr His Arg
210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
            245                 250                 255

Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
            275                 280                 285

Ala Asn Ile Phe Tyr Ser Val Leu Thr Ile Asp Lys Met Gln Asn Lys
            290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
            405                 410                 415

Asn Leu Thr Ala Thr Leu Ile Val Asn Val Lys Pro Asp Lys Thr His
            420                 425                 430

Thr Cys Pro Pro Cys Pro Ala Pro Glu Leu Leu Gly Gly Pro Ser Val
            435                 440                 445

Phe Leu Phe Pro Pro Lys Pro Lys Asp Thr Leu Met Ile Ser Arg Thr
        450                 455                 460

Pro Glu Val Thr Cys Val Val Val Asp Val Ser His Glu Asp Pro Glu
465                 470                 475                 480
```

| | | | | | | | | | | | |
|---|---|---|---|---|---|---|---|---|---|---|---|
|Val|Lys|Phe|Asn|Trp|Tyr|Val|Asp|Gly|Val|Glu|Val|His|Asn|Ala|Lys|
| | | | |485| | | |490| | | |495| | | |

Thr Lys Pro Arg Glu Glu Gln Tyr Asn Ser Thr Tyr Arg Val Val Ser
            500                 505                 510

Val Leu Thr Val Leu His Gln Asp Trp Leu Asn Gly Lys Glu Tyr Lys
            515                 520                 525

Cys Lys Val Ser Asn Lys Ala Leu Pro Ala Pro Ile Glu Lys Thr Ile
            530                 535                 540

Ser Lys Ala Lys Gly Gln Pro Arg Glu Pro Gln Val Tyr Thr Leu Pro
545                 550                 555                 560

Pro Ser Arg Glu Glu Met Thr Lys Asn Gln Val Ser Leu Thr Cys Leu
            565                 570                 575

Val Lys Gly Phe Tyr Pro Ser Asp Ile Ala Val Glu Trp Glu Ser Asn
            580                 585                 590

Gly Gln Pro Glu Asn Asn Tyr Lys Thr Thr Pro Pro Val Leu Asp Ser
            595                 600                 605

Asp Gly Ser Phe Phe Leu Tyr Ser Lys Leu Thr Val Asp Lys Ser Arg
            610                 615                 620

Trp Gln Gln Gly Asn Val Phe Ser Cys Ser Val Met His Glu Ala Leu
625                 630                 635                 640

His Asn His Tyr Thr Gln Lys Ser Leu Ser Leu Ser Pro Gly Lys
            645                 650                 655

<210> SEQ ID NO 10
<211> LENGTH: 1965
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
atggtcagct actgggacac cggggtcctg ctgtgcgcgc tgctcagctg tctgcttctc      60
acaggatcta gttcaggttc aaaattaaaa gatcctgaac tgagttttaaa aggcacccag     120 cacatcatgc aagcaggcca gacactgcat ctccaatgca gggggaagc agcccataaa       180 tggtctttgc ctgaaatggt gagtaaggaa agcgaaaggc tgagcataac taaatctgcc     240
tgtggaagaa atggcaaaca attctgcagt actttaacct tgaacacagc tcaagcaaac     300
cacactggct tctacagctg caaatatcta gctgtaccta cttcaaagaa gaaggaaaca     360
gaatctgcaa tctatatatt tattagtgat acaggtagac ttttcgtaga gatgtacagt     420
gaaatccccg aaattataca catgactgaa ggaagggagc tcgtcattcc ctgccgggtt     480
acgtcaccta acatcactgt tacttttaaaa agtttccac ttgacacttt gatccctgat     540
ggaaaacgca taatctggga cagtagaaag ggcttcatca tatcaaatgc aacgtacaaa     600
gaaatagggc ttctgacctg tgaagcaaca gtcaatgggc attttgtataa acaaactat      660 ctcacacatc gacaaaccaa tacaatcata gatgtccaaa taagcacacc acgcccagtc     720
aaattactta gaggccatac tcttgtcctc aattgtactg ctaccactcc cttgaacacg     780
agagttcaaa tgacctggag ttaccctgat gaaaaaaata gagagcttc cgtaaggcga     840 cgaattgacc aaagcaattc ccatgccaac atattctaca gtgttcttac tattgacaaa     900
atgcagaaca agacaaagg actttatact tgtcgtgtaa ggagtggacc atcattcaa      960 tctgttaaca cctcagtgca tatatatgat aaagcattca tcactgtgaa acatcgaaaa     1020

```
cagcaggtgc ttgaaaccgt agctggcaag cggtcttacc ggctctctat gaaagtgaag    1080
gcatttccct cgccggaagt tgtatggtta aagatgggt tacctgcgac tgagaaatct      1140
gctcgctatt tgactcgtgg ctactcgtta attatcaagg acgtaactga agaggatgca    1200
gggaattata caatcttgct gagcataaaa cagtcaaatg tgtttaaaaa cctcactgcc    1260
actctaattg tcaatgtgaa acccgacaaa actcacacat gcccaccgtg cccagcacct    1320
gaactcctgg ggggaccgtc agtcttcctc ttccccccaa acccaagga caccctcatg    1380 atctcccgga cccctgaggt cacatgcgtg gtggtggacg tgagccacga agaccctgag    1440
gtcaagttca actggtacgt ggacggcgtg gaggtgcata atgccaagac aaagccgcgg    1500
gaggagcagt acaacagcac gtaccgtgtg gtcagcgtcc tcaccgtcct gcaccaggac    1560
tggctgaatg gcaaggagta caagtgcaag gtctccaaca aagccctccc agcccccatc    1620
gagaaaacca tctccaaagc caagggcag ccccgagaac acaggtgta caccctgccc    1680 ccatcccggg aggagatgac caagaaccag gtcagcctga cctgcctggt caaaggcttc    1740
tatcccagcg acatcgccgt ggagtgggag agcaatgggc agccggagaa caactacaag    1800
accacgcctc ccgtgctgga ctccgacggc tccttcttcc tctacagcaa gctcaccgtg    1860
gacaagagca ggtggcagca ggggaacgtc ttctcatgct ccgtgatgca cgaggctctg    1920
cacaaccact acacgcagaa gagcctctcc ctgtctccgg gtaaa                    1965
```

<210> SEQ ID NO 11
<211> LENGTH: 556
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 11

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ile Phe Ile Ser Asp Thr
            20                  25                  30

Gly Arg Pro Phe Val Glu Met Tyr Ser Glu Ile Pro Glu Ile Ile His
        35                  40                  45

Met Thr Glu Gly Arg Glu Leu Val Ile Pro Cys Arg Val Thr Ser Pro
    50                  55                  60

Asn Ile Thr Val Thr Leu Lys Lys Phe Pro Leu Asp Thr Leu Ile Pro
65                  70                  75                  80

Asp Gly Lys Arg Ile Ile Trp Asp Ser Arg Lys Gly Phe Ile Ile Ser
                85                  90                  95

Asn Ala Thr Tyr Lys Glu Ile Gly Leu Leu Thr Cys Glu Ala Thr Val
            100                 105                 110

Asn Gly His Leu Tyr Lys Thr Asn Tyr Leu Thr His Arg Gln Thr Asn
        115                 120                 125

Thr Ile Ile Asp Val Gln Ile Ser Thr Pro Arg Pro Val Lys Leu Leu
    130                 135                 140

Arg Gly His Thr Leu Val Leu Asn Cys Thr Ala Thr Thr Pro Leu Asn
145                 150                 155                 160

Thr Arg Val Gln Met Thr Trp Ser Tyr Pro Asp Glu Lys Asn Lys Arg
                165                 170                 175

Ala Ser Val Arg Arg Arg Ile Asp Gln Ser Asn Ser His Ala Asn Ile
            180                 185                 190
```

```
Phe Tyr Ser Val Leu Thr Ile Asp Lys Met Gln Asn Lys Asp Lys Gly
            195                 200                 205

Leu Tyr Thr Cys Arg Val Arg Ser Gly Pro Ser Phe Lys Ser Val Asn
        210                 215                 220

Thr Ser Val His Ile Tyr Asp Lys Ala Phe Ile Thr Val Lys His Arg
225                 230                 235                 240

Lys Gln Gln Val Leu Glu Thr Val Ala Gly Lys Arg Ser Tyr Arg Leu
                245                 250                 255

Ser Met Lys Val Lys Ala Phe Pro Pro Glu Val Val Trp Leu Lys
        260                 265                 270

Asp Gly Leu Pro Ala Thr Glu Lys Ser Ala Arg Tyr Leu Thr Arg Gly
            275                 280                 285

Tyr Ser Leu Ile Ile Lys Asp Val Thr Glu Glu Asp Ala Gly Asn Tyr
        290                 295                 300

Thr Ile Leu Leu Ser Ile Lys Gln Ser Asn Val Phe Lys Asn Leu Thr
305                 310                 315                 320

Ala Thr Leu Ile Val Asn Val Lys Pro Asp Lys Thr His Thr Cys Pro
                325                 330                 335

Pro Cys Pro Ala Pro Glu Leu Leu Gly Gly Pro Ser Val Phe Leu Phe
            340                 345                 350

Pro Pro Lys Pro Lys Asp Thr Leu Met Ile Ser Arg Thr Pro Glu Val
        355                 360                 365

Thr Cys Val Val Val Asp Val Ser His Glu Asp Pro Glu Val Lys Phe
    370                 375                 380

Asn Trp Tyr Val Asp Gly Val Glu Val His Asn Ala Lys Thr Lys Pro
385                 390                 395                 400

Arg Glu Glu Gln Tyr Asn Ser Thr Tyr Arg Val Val Ser Val Leu Thr
                405                 410                 415

Val Leu His Gln Asp Trp Leu Asn Gly Lys Glu Tyr Lys Cys Lys Val
            420                 425                 430

Ser Asn Lys Ala Leu Pro Ala Pro Ile Glu Lys Thr Ile Ser Lys Ala
        435                 440                 445

Lys Gly Gln Pro Arg Glu Pro Gln Val Tyr Thr Leu Pro Pro Ser Arg
450                 455                 460

Glu Glu Met Thr Lys Asn Gln Val Ser Leu Thr Cys Leu Val Lys Gly
465                 470                 475                 480

Phe Tyr Pro Ser Asp Ile Ala Val Glu Trp Glu Ser Asn Gly Gln Pro
                485                 490                 495

Glu Asn Asn Tyr Lys Thr Thr Pro Pro Val Leu Asp Ser Asp Gly Ser
            500                 505                 510

Phe Phe Leu Tyr Ser Lys Leu Thr Val Asp Lys Ser Arg Trp Gln Gln
        515                 520                 525

Gly Asn Val Phe Ser Cys Ser Val Met His Glu Ala Leu His Asn His
    530                 535                 540

Tyr Thr Gln Lys Ser Leu Ser Leu Ser Pro Gly Lys
545                 550                 555

<210> SEQ ID NO 12
<211> LENGTH: 1668
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
```

-continued

```
atggtcagct actgggacac cggggtcctg ctgtgcgcgc tgctcagctg tctgcttctc        60
acaggatcta gttcaggtat atttattagt gatacaggta gacctttcgt agagatgtac       120
agtgaaatcc ccgaaattat acacatgact gaaggaaggg agctcgtcat tccctgccgg       180
gttacgtcac ctaacatcac tgttacttta aaaaagtttc cacttgacac tttgatccct       240
gatggaaaac gcataatctg ggacagtaga aagggcttca tcatatcaaa tgcaacgtac       300
aaagaaatag gcttctgac ctgtgaagca acagtcaatg gcatttgta aagacaaac         360
tatctcacac atcgacaaac caatacaatc atagatgtcc aaataagcac accacgccca       420
gtcaaattac ttagaggcca tactcttgtc ctcaattgta ctgctaccac tcccttgaac       480
acgagagttc aaatgacctg gagttaccct gatgaaaaaa ataagagagc ttccgtaagg       540
cgacgaattg accaaagcaa ttcccatgcc aacatattct acagtgttct tactattgac       600
aaaatgcaga caaagacaa aggactttat acttgtcgtg taaggagtgg accatcattc        660
aaatctgtta cacctcagt gcatatatat gataaagcat tcatcactgt gaaacatcga        720
aaacagcagg tgcttgaaac cgtagctggc aagcggtctt accggctctc tatgaaagtg       780
aaggcatttc cctcgccgga agttgtatgg ttaaaagatg ggttacctgc gactgagaaa       840
tctgctcgct atttgactcg tggctactcg ttaattatca aggacgtaac tgaagaggat       900
gcagggaatt atacaatctt gctgagcata aacagtcaa atgtgtttaa aaacctcact        960
gccactctaa ttgtcaatgt gaaacccgac aaaactcaca catgcccacc gtgcccagca      1020
cctgaactcc tggggggacc gtcagtcttc ctcttccccc caaaacccaa ggacaccctc      1080
atgatctccc ggacccctga ggtcacatgc gtggtggtgg acgtgagcca cgaagaccct      1140
gaggtcaagt tcaactggta cgtggacggc gtggaggtgc ataatgccaa gacaaagccg      1200
cgggaggagc agtacaacag cacgtaccgt gtggtcagcg tcctcaccgt cctgcaccag      1260
gactggctga atggcaagga gtacaagtgc aaggtctcca acaaagccct cccagccccc      1320
atcgagaaaa ccatctccaa agccaaaggg cagccccgag aaccacaggt gtacaccctg      1380
cccccatccc gggaggagat gaccaagaac caggtcagcc tgacctgcct ggtcaaaggc      1440
ttctatccca gcgacatcgc cgtggagtgg gagagcaatg ggcagccgga gaacaactac      1500
aagaccacgc ctcccgtgct ggactccgac ggctccttct tcctctacag caagctcacc      1560
gtggacaaga gcaggtggca gcaggggaac gtcttctcat gctccgtgat gcacgaggct      1620
ctgcacaacc actacacgca gaagagcctc tccctgtctc cgggtaaa                  1668
```

<210> SEQ ID NO 13
<211> LENGTH: 456
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ile Phe Ile Ser Asp Thr
            20                  25                  30

Gly Arg Pro Phe Val Glu Met Tyr Ser Glu Ile Pro Glu Ile Ile His
        35                  40                  45

Met Thr Glu Gly Arg Glu Leu Val Ile Pro Cys Arg Val Thr Ser Pro
    50                  55                  60
```

-continued

```
Asn Ile Thr Val Thr Leu Lys Lys Phe Pro Leu Asp Thr Leu Ile Pro
 65                  70                  75                  80

Asp Gly Lys Arg Ile Ile Trp Asp Ser Arg Lys Gly Phe Ile Ile Ser
             85                  90                  95

Asn Ala Thr Tyr Lys Glu Ile Gly Leu Leu Thr Cys Glu Ala Thr Val
            100                 105                 110

Asn Gly His Leu Tyr Lys Thr Asn Tyr Leu Thr His Arg Gln Thr Asn
            115                 120                 125

Thr Ile Ile Asp Val Phe Ile Thr Val Lys His Arg Lys Gln Gln Val
        130                 135                 140

Leu Glu Thr Val Ala Gly Lys Arg Ser Tyr Arg Leu Ser Met Lys Val
145                 150                 155                 160

Lys Ala Phe Pro Ser Pro Glu Val Val Trp Leu Lys Asp Gly Leu Pro
                165                 170                 175

Ala Thr Glu Lys Ser Ala Arg Tyr Leu Thr Arg Gly Tyr Ser Leu Ile
            180                 185                 190

Ile Lys Asp Val Thr Glu Glu Asp Ala Gly Asn Tyr Thr Ile Leu Leu
        195                 200                 205

Ser Ile Lys Gln Ser Asn Val Phe Lys Asn Leu Thr Ala Thr Leu Ile
210                 215                 220

Val Asn Val Lys Pro Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
450                 455
```

<210> SEQ ID NO 14
<211> LENGTH: 1368

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

```
atggtcagct actgggacac cggggtcctg ctgtgcgcgc tgctcagctg tctgcttctc      60
acaggatcta gttcaggtat atttattagt gatacaggta gacctttcgt agagatgtac     120
agtgaaatcc ccgaaattat acacatgact gaaggaaggg agctcgtcat tccctgccgg     180
gttacgtcac ctaacatcac tgttacttta aaaaagtttc cacttgacac tttgatccct     240
gatggaaaac gcataatctg ggacagtaga aagggcttca tcatatcaaa tgcaacgtac     300
aaagaaatag gcttctgac ctgtgaagca cagtcaatg gcatttgta taagacaaac        360
tatctcacac atcgacaaac caatacaatc atagatgtct tcatcactgt gaaacatcga     420
aaacagcagg tgcttgaaac cgtagctggc aagcggtctt accggctctc tatgaaagtg     480
aaggcatttc cctcgccgga agttgtatgg ttaaaagatg ggttacctgc gactgagaaa     540
tctgctcgct atttgactcg tggctactcg ttaattatca aggacgtaac tgaagaggat     600
gcagggaatt atacaatctt gctgagcata aacagtcaa atgtgtttaa aaacctcact     660
gccactctaa ttgtcaatgt gaaacccgac aaaactcaca catgcccacc gtgcccagca     720
cctgaactcc tggggggacc gtcagtcttc ctcttccccc caaaacccaa ggacaccctc     780
atgatctccc ggacccctga ggtcacatgc gtggtggtgg acgtgagcca cgaagaccct     840
gaggtcaagt tcaactggta cgtggacggc gtggaggtgc ataatgccaa gacaaagccg     900
cgggaggagc agtacaacag cacgtaccgt gtggtcagcg tcctcaccgt cctgcaccag     960
gactggctga atggcaagga gtacaagtgc aaggtctcca acaaagccct cccagccccc    1020
atcgagaaaa ccatctccaa agccaaaggg cagccccgag aaccacaggt gtacaccctg    1080
cccccatccc gggaggagat gaccaagaac caggtcagcc tgacctgcct ggtcaaaggc    1140
ttctatccca gcgacatcgc cgtggagtgg gagagcaatg ggcagccgga gaacaactac    1200
aagaccacgc ctcccgtgct ggactccgac ggctccttct tcctctacag caagctcacc    1260
gtggacaaga gcaggtggca gcaggggaac gtcttctcat gctccgtgat gcacgaggct    1320
ctgcacaacc actacacgca gaagagcctc tccctgtctc cgggtaaa              1368
```